(12) United States Patent
Mantri et al.

(10) Patent No.: US 12,178,498 B2
(45) Date of Patent: Dec. 31, 2024

(54) SURGICAL PROBE WITH INDEPENDENT ENERGY SOURCES

(71) Applicant: PROCEPT BioRobotics Corporation, Redwood City, CA (US)

(72) Inventors: Surag Mantri, East Palo Alto, CA (US); Kevin Patrick Staid, Lowell, MA (US); James Luis Badia, Redwood City, CA (US); Friedrich Ho, Mountain View, CA (US); Scott D. Taylor, San Martin, CA (US); Peter Bentley, Reno, NV (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 0 days.

(21) Appl. No.: 18/000,786

(22) PCT Filed: Apr. 20, 2022

(86) PCT No.: PCT/US2022/025617
§ 371 (c)(1),
(2) Date: Dec. 5, 2022

(87) PCT Pub. No.: WO2022/226103
PCT Pub. Date: Oct. 27, 2022

(65) Prior Publication Data
US 2023/0210586 A1  Jul. 6, 2023

Related U.S. Application Data

(60) Provisional application No. 63/201,250, filed on Apr. 20, 2021.

(51) Int. Cl.
*A61B 18/14* (2006.01)
*A61B 34/30* (2016.01)

(52) U.S. Cl.
CPC .......... *A61B 18/1482* (2013.01); *A61B 34/30* (2016.02); *A61B 2217/005* (2013.01); *A61B 2217/007* (2013.01)

(58) Field of Classification Search
CPC ................ A61B 18/1482; A61B 34/30; A61B 2217/005; A61B 2217/007
(Continued)

(56) References Cited

U.S. PATENT DOCUMENTS 4,389,071 A   6/1983  Johnson, Jr.
4,561,798 A  12/1985  Elcrin
(Continued)

FOREIGN PATENT DOCUMENTS

CN   101394877   3/2009
CN   101711132   5/2010
(Continued)

OTHER PUBLICATIONS

Jakopec et al., Acrobot: a "hands-on" robot for total knee replacement surgery, 2002, IEEE, p. 116-120 (Year: 2002).
(Continued)

*Primary Examiner* — Aaron F Roane
(74) *Attorney, Agent, or Firm* — FisherBroyles, LLP; John K. Shimmick

(57) ABSTRACT

An energy source is offset from an elongate probe axis with an extension. The amount of offset of the energy source can be controlled by varying an amount of offset of the extension. The energy source rotated and translated at the offset distance to resect tissue. In some embodiments, the probe is configured to receive a second treatment probe comprising a second energy source, in which the second energy source is rotated and translated relative to the first treatment probe, which can improve positional accuracy and stability. The energy source and the extension can be coupled to a linkage
(Continued)

to offset the energy source, and to translate and rotate the energy source with varying amounts of offset. The linkage can be coupled to a processor and one or more of the energy source moved in accordance with a treatment profile.

18 Claims, 22 Drawing Sheets

(58) Field of Classification Search
USPC .......................................................... 606/1
See application file for complete search history.

(56) References Cited

U.S. PATENT DOCUMENTS

| | | | |
|---|---|---|---|
| 4,932,956 A | 6/1990 | Reddy | |
| 5,527,330 A * | 6/1996 | Tovey | A61B 17/32037 606/167 |
| 6,039,695 A | 3/2000 | Sakamoto | |
| 6,331,181 B1 | 12/2001 | Tierney | |
| 6,338,714 B1 | 1/2002 | Krause | |
| 6,375,635 B1 | 4/2002 | Moutafis | |
| 6,511,493 B1 | 1/2003 | Moutafis | |
| 7,021,173 B2 | 4/2006 | Stoianovici | |
| 7,115,100 B2 * | 10/2006 | McRury | A61B 17/3203 600/564 |
| 7,462,187 B2 * | 12/2008 | Johnston | A61B 17/1688 604/533 |
| 7,882,841 B2 | 2/2011 | Aljuri | |
| 8,062,246 B2 | 11/2011 | Moutafis | |
| 8,152,816 B2 | 4/2012 | Tuma | |
| 8,229,188 B2 | 7/2012 | Rusko | |
| 8,398,541 B2 | 3/2013 | Dimaio | |
| 8,660,635 B2 | 2/2014 | Simon | |
| 8,814,921 B2 | 8/2014 | Aljuri | |
| 8,827,948 B2 | 9/2014 | Romo | |
| 8,961,533 B2 | 2/2015 | Stahler | |
| 9,072,452 B2 | 7/2015 | Vayser | |
| 9,144,461 B2 | 9/2015 | Kruecker | |
| 9,238,122 B2 * | 1/2016 | Malhi | A61B 17/32037 |
| 9,277,969 B2 | 3/2016 | Brannan | |
| 9,314,306 B2 | 4/2016 | Yu | |
| 9,364,251 B2 | 6/2016 | Aljuri | |
| 9,610,131 B2 | 4/2017 | Stoianovici | |
| 9,737,371 B2 | 8/2017 | Romo | |
| 9,867,635 B2 | 1/2018 | Alvarez | |
| 9,877,788 B2 | 1/2018 | Stoianovici | |
| 10,130,427 B2 | 11/2018 | Tanner | |
| 10,226,298 B2 | 3/2019 | Ourselin | |
| 10,231,867 B2 | 3/2019 | Alvarez | |
| 10,307,214 B2 | 6/2019 | Lathrop | |
| 10,423,757 B2 | 9/2019 | Kruecker | |
| 10,441,371 B2 | 10/2019 | Hendrick | |
| 10,448,956 B2 | 10/2019 | Gordon | |
| 10,555,780 B2 | 2/2020 | Tanner | |
| 10,555,785 B2 | 2/2020 | Yeung | |
| 10,646,295 B2 | 5/2020 | Stoianovici | |
| 10,779,897 B2 | 9/2020 | Rockrohr | |
| 11,071,601 B2 | 7/2021 | Staid | |
| 11,096,753 B1 | 8/2021 | Mantri | |
| 11,172,955 B2 * | 11/2021 | Dayton | A61B 17/320016 |
| 11,278,451 B2 | 3/2022 | Andrews | |
| 11,357,586 B2 | 6/2022 | Huang | |
| 11,589,913 B2 * | 2/2023 | Witte | A61G 13/1295 |
| 11,590,319 B2 | 2/2023 | Debuys | |
| 2002/0121577 A1 | 9/2002 | Metelski | |
| 2004/0024311 A1 | 2/2004 | Quaid | |
| 2004/0034282 A1 | 2/2004 | Quaid | |
| 2004/0230211 A1 | 11/2004 | Moutafis | |
| 2005/0261692 A1 | 11/2005 | Carrison | |
| 2006/0118495 A1 | 6/2006 | Kondratalv | |
| 2006/0142657 A1 | 6/2006 | Quaid | |
| 2006/0205996 A1 | 9/2006 | Presthus | |
| 2008/0009747 A1 | 1/2008 | Saadat | |
| 2008/0027420 A1 | 1/2008 | Wang | |
| 2009/0306692 A1 | 12/2009 | Barrington | |
| 2010/0010524 A1 | 1/2010 | Barrington | |
| 2010/0036245 A1 | 2/2010 | Yu | |
| 2011/0184391 A1 | 7/2011 | Aljuri | |
| 2012/0035462 A1 | 2/2012 | Maurer, Jr. | |
| 2012/0071894 A1 | 3/2012 | Tanner | |
| 2012/0095498 A1 | 4/2012 | Stefanchik | |
| 2013/0218186 A1 | 8/2013 | Dubois | |
| 2013/0239392 A1 | 9/2013 | Solomon | |
| 2014/0039314 A1 | 2/2014 | Stoianovici | |
| 2014/0094968 A1 | 4/2014 | Taylor | |
| 2014/0142438 A1 | 5/2014 | Ludwin | |
| 2014/0194896 A1 | 7/2014 | Frimer | |
| 2014/0309649 A1 | 10/2014 | Alvarez | |
| 2015/0025539 A1 | 1/2015 | Alvarez | |
| 2015/0080907 A1 | 3/2015 | Herrell | |
| 2015/0088107 A1 | 3/2015 | Aljuri | |
| 2015/0173726 A1 | 6/2015 | Lohmeier | |
| 2015/0366546 A1 | 12/2015 | Kamen | |
| 2016/0067450 A1 | 3/2016 | Kowshik | |
| 2016/0262827 A1 | 9/2016 | Ross | |
| 2017/0014269 A1 | 1/2017 | Draheim | |
| 2017/0020253 A1 | 1/2017 | Drozdowicz | |
| 2017/0189127 A1 | 7/2017 | Weir | |
| 2017/0202537 A1 | 7/2017 | Ippolito | |
| 2017/0245878 A1 | 8/2017 | Aljuri | |
| 2017/0245949 A1 | 8/2017 | Randle | |
| 2017/0273797 A1 | 9/2017 | Gordon | |
| 2018/0014891 A1 | 1/2018 | Krebs | |
| 2018/0021960 A1 | 1/2018 | Grant | |
| 2018/0028261 A1 | 2/2018 | Chen | |
| 2018/0185018 A1 * | 7/2018 | Piskun | A61B 1/3132 |
| 2018/0263647 A1 | 9/2018 | Aljuri | |
| 2018/0263685 A1 | 9/2018 | Onik | |
| 2018/0318011 A1 | 11/2018 | Leibinger | |
| 2018/0353253 A1 | 12/2018 | Bowling | |
| 2019/0015166 A1 | 1/2019 | Mahoney | |
| 2019/0021753 A1 | 1/2019 | Jinno | |
| 2019/0076674 A1 | 3/2019 | Ergün | |
| 2019/0105023 A1 | 4/2019 | Aljuri | |
| 2019/0105117 A1 | 4/2019 | Brisson | |
| 2019/0142396 A1 | 5/2019 | Stoianovici | |
| 2019/0201214 A1 | 7/2019 | Miller | |
| 2019/0202066 A1 | 7/2019 | Maret | |
| 2019/0231450 A1 | 8/2019 | Waterbury | |
| 2019/0262057 A1 | 8/2019 | Grant | |
| 2019/0321119 A1 | 10/2019 | Yeung | |
| 2019/0336238 A1 | 11/2019 | Yu | |
| 2020/0008874 A1 | 1/2020 | Barbagli | |
| 2020/0020249 A1 | 1/2020 | Jarc | |
| 2020/0138454 A1 | 5/2020 | Patel | |
| 2020/0237423 A1 * | 7/2020 | Witte | A61G 13/1235 |
| 2020/0261297 A1 | 8/2020 | Strydom | |
| 2020/0360097 A1 | 11/2020 | Dimaio | |
| 2020/0360100 A1 | 11/2020 | Mantri | |
| 2020/0405403 A1 | 12/2020 | Shelton, IV | |
| 2021/0030496 A1 | 2/2021 | Devengenzo | |
| 2021/0137612 A1 | 5/2021 | Staid | |
| 2021/0378766 A1 | 12/2021 | Staid | |
| 2021/0401521 A1 | 12/2021 | Mantri | |
| 2021/0401522 A1 | 12/2021 | Mantri | |
| 2022/0273166 A1 | 9/2022 | Nord | |
| 2024/0285346 A1 | 8/2024 | Shi | |
| 2024/0299003 A1 | 9/2024 | Shi | |

FOREIGN PATENT DOCUMENTS

| | | | |
|---|---|---|---|
| CN | 102905633 | 1/2013 | |
| CN | 105764436 A | 7/2016 | |
| CN | 111449694 | 7/2020 | |
| EP | 1486900 | 12/2004 | |
| NL | 1019547 | 5/2003 | |
| WO | WO 01/50966 | * 7/2001 | A61B 17/22 |
| WO | 2004004914 | 1/2004 | |
| WO | 2008083407 A1 | 7/2008 | |
| WO | 2008098253 | 8/2008 | |
| WO | 2009111736 A1 | 9/2009 | |
| WO | 2011097505 A1 | 8/2011 | |
| WO | 2013053614 | 4/2013 | |

(56) References Cited

FOREIGN PATENT DOCUMENTS

| | | |
|---|---|---|
| WO | 2013130895 A1 | 9/2013 |
| WO | 2014127242 | 8/2014 |
| WO | 2014165703 A1 | 10/2014 |
| WO | 2015035249 A2 | 3/2015 |
| WO | 2015200538 A1 | 12/2015 |
| WO | 2016004071 A1 | 1/2016 |
| WO | 2016037132 A1 | 3/2016 |
| WO | 2016037137 A1 | 3/2016 |
| WO | 2016054256 | 4/2016 |
| WO | 2017161331 A1 | 9/2017 |
| WO | 20170192603 | 9/2017 |
| WO | 2018013848 | 1/2018 |
| WO | 2019032986 | 2/2019 |
| WO | 2019137665 | 7/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021096741 | 5/2021 |
| WO | 2021130229 | 7/2021 |
| WO | 2021262565 | 12/2021 |
| WO | 2021263276 | 12/2021 |
| WO | 2022011177 | 1/2022 |
| WO | 2022226103 | 10/2022 |
| WO | 2023066148 | 4/2023 |
| WO | 2023072146 | 5/2023 |
| WO | 2023083352 | 5/2023 |
| WO | 2023088305 | 5/2023 |

OTHER PUBLICATIONS

Non-Final Office Action for U.S. Appl. No. 16/940,085, 14 pages (Jun. 23, 2023).

Notice of Allowance for U.S. Appl. No. 17/304,572, 9 pages (Jun. 5, 2023).

Sen et al., A cooperatively controlled robot for ultrasound monitoring of radiation therapy, 2013, IEEE, p. 3071-3076 (Year: 2013).

Chirstoforou et al., Manipulator for magnetic resonance imaging guided interventions: design, prototype and feasibility, 2006, IEEE p. 3838-3843 (Year: 2006).

Christoforou et al., Robotic Arm for Magnetic Resonance Imaging Guided Interventions, 2006, IEEE, p. 1-6 (Year: 2006).

Dwyer et al., A miniaturised robotic probe for real-time intraoperative fusion of ultrasound and endomicroscopy, 2015, EEE, p. 1196-1201 (Year: 2015).

International Search Report and Written Opinion for PCT/US2022/025617, 33 pages (Jul. 14, 2022).

Lim et al. "Robotic Transrectal Ultrasound-Guided Prostate Biopsy." IEEE Trans BME. Jan. 7, 2019. 11 pages. (Year: 2019).

Marmol et al., ArthroSLAM: Multi-Sensor Robust Visual Localization for Minimally Invasive Orthopedic Surgery, 2018, IEEE, p. 3882-3889 (Year: 2018).

Rosa et al., Laparoscopic optical biopsies: In vivo robotized mosaicing with probe-based confocal endomicroscopy, 2011, IEEE, p. 1339-1345 (Year: 2011).

Stoianovici et al. "MRI-Safe Robot for Endorectal Prostate Biopsy." IEEE/ASME Trans Mechatronics, vol. 19, No. Aug. 4, 2014. pp. 1289-1299. (Year: 2014).

Xiao et al., Ultrasound Guided Robotic System for Transperineal Biopsy of the Prostate, 2006, IEEE, p. 1315-1320 (Year: 2006).

Caponero, M.A., et al., "Fabrication and calibration of three temperature probes for monitoring the effects of thermal cancer ablation," 2017, IEEE, pp. 1-5 (2017).

* cited by examiner

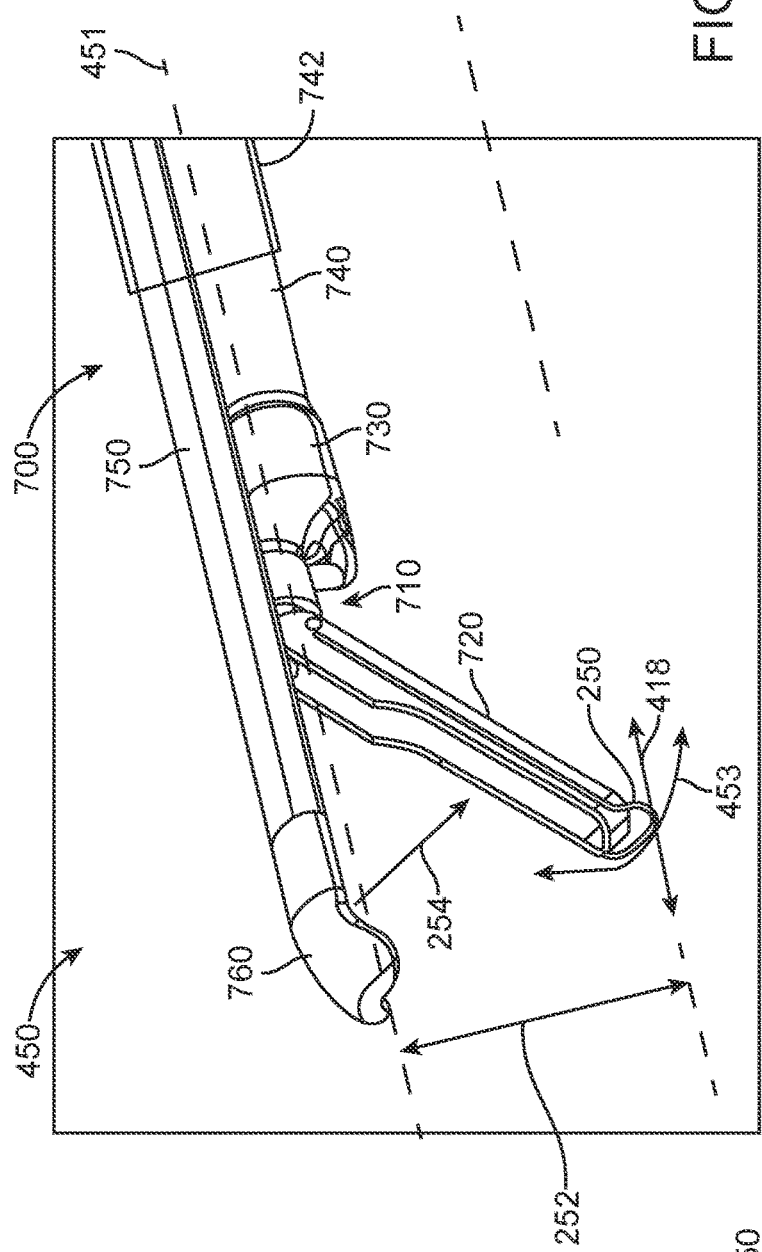
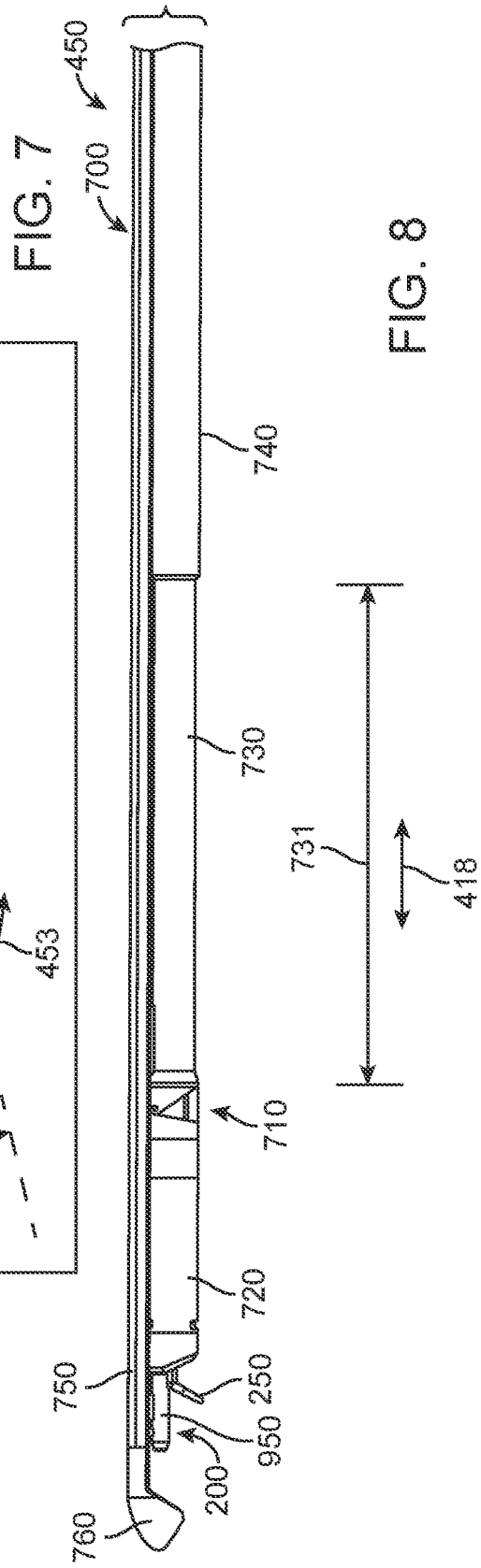
FIG. 7
FIG. 8

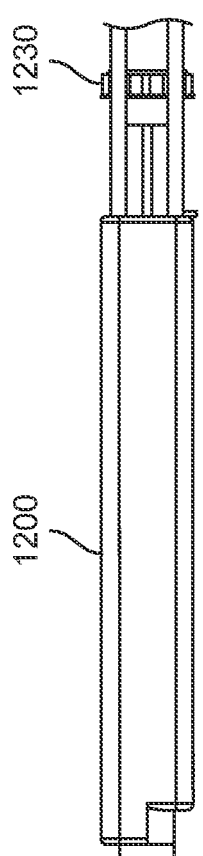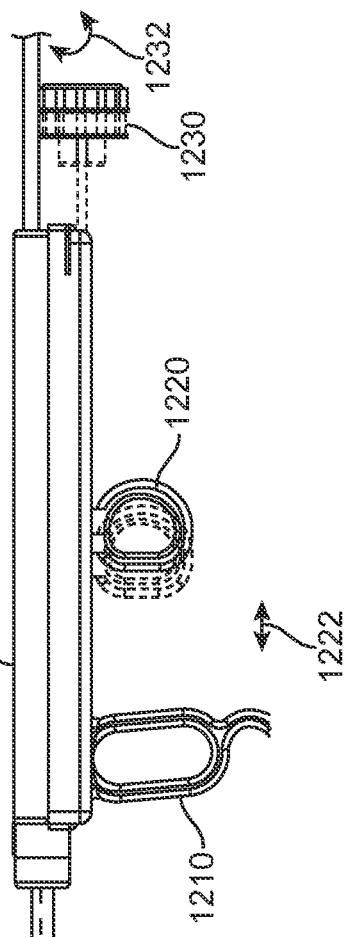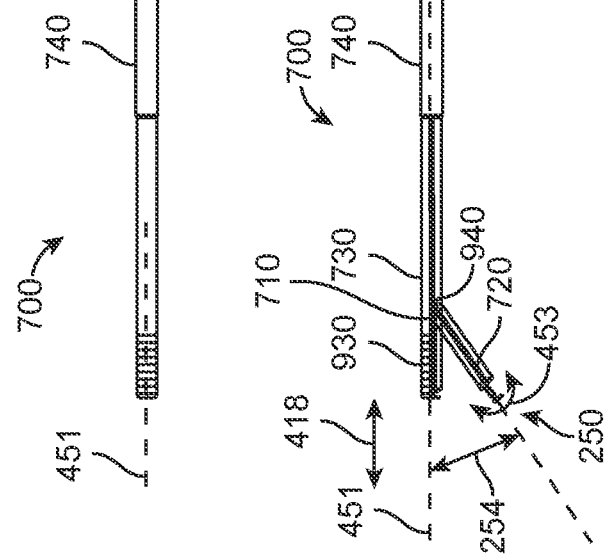
FIG. 12A
FIG. 12B

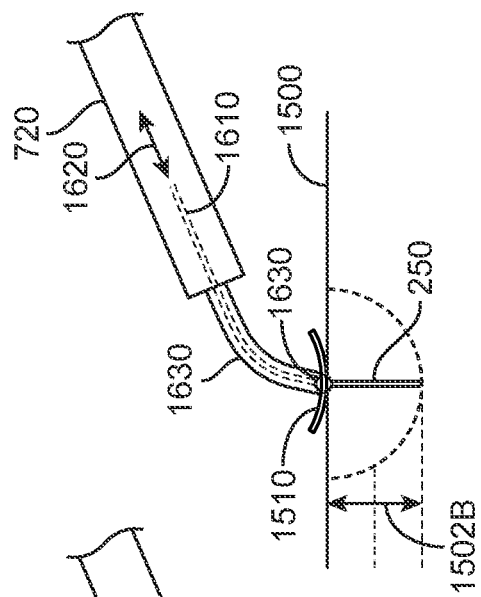
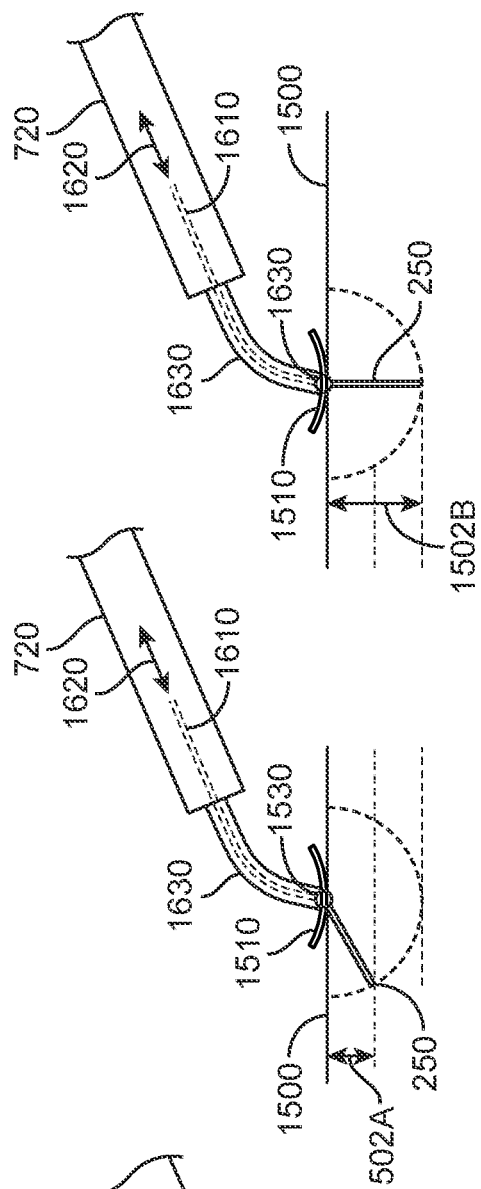
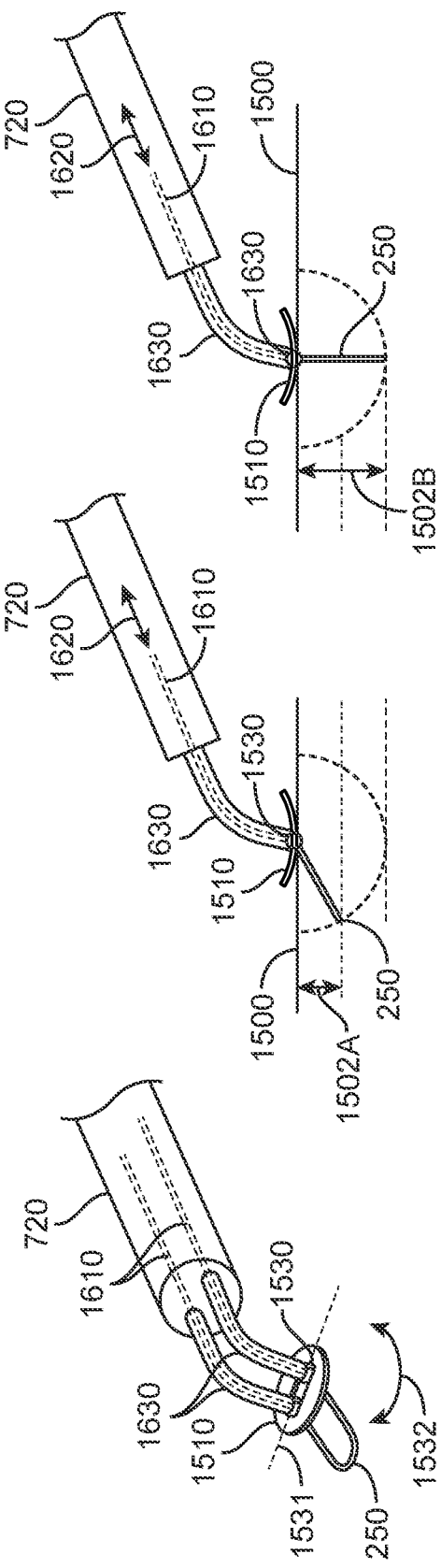
FIG. 16A  FIG. 16B  FIG. 16C
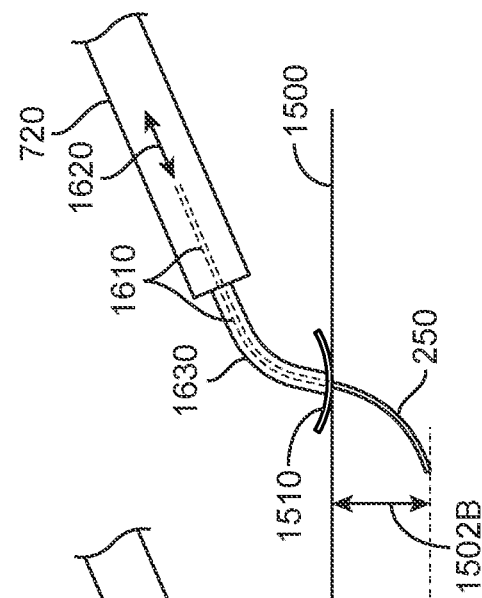
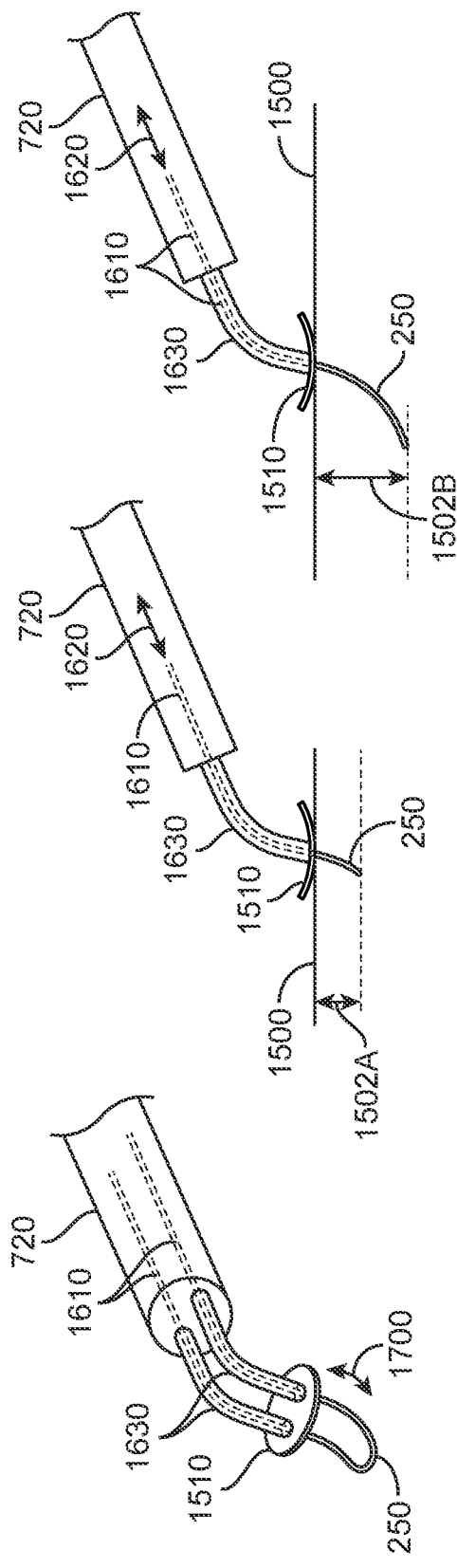
FIG. 17A  FIG. 17B  FIG. 17C

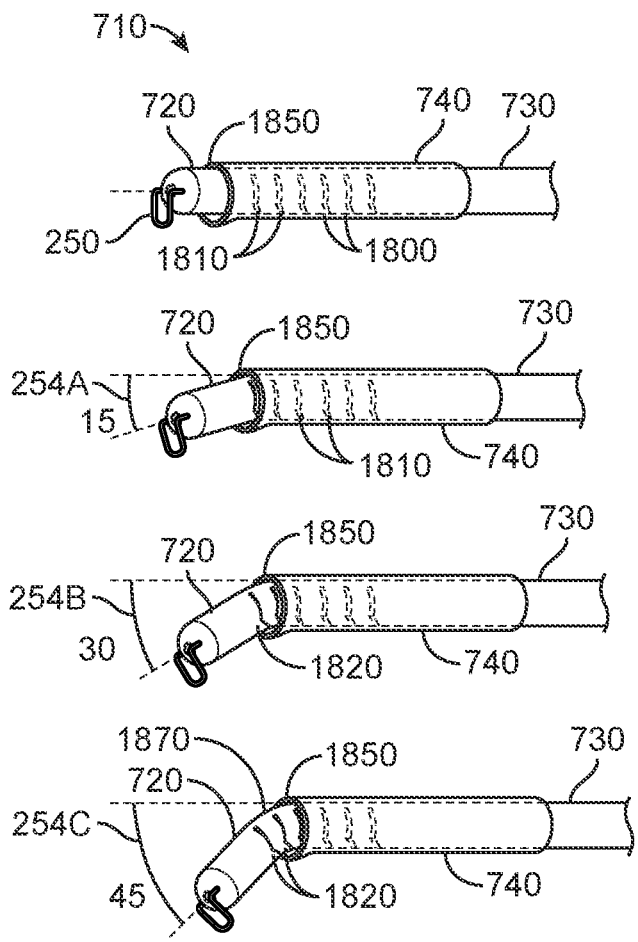
FIG. 18A
FIG. 18B
FIG. 18C
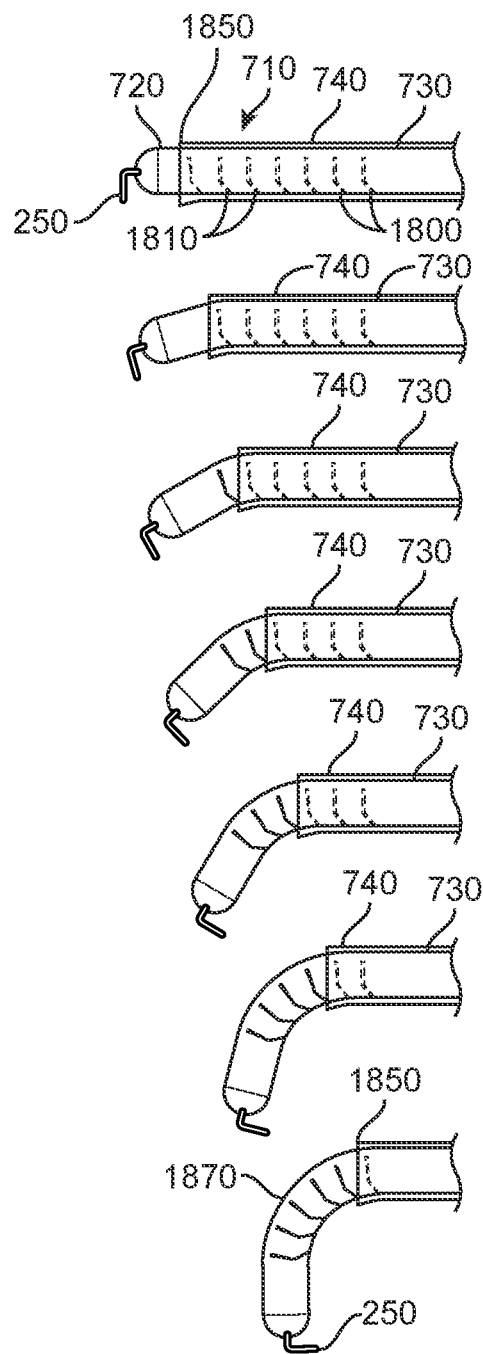
FIG. 18D

SURGICAL PROBE WITH INDEPENDENT ENERGY SOURCES

CROSS REFERENCE

This application is a 371 national phase of PCT/US2022/025617, filed Apr. 20, 2022, published as WO 2022/226103 on Oct. 27, 2022, and claims the benefit under 35 U.S.C. § 119 (e) of U.S. Provisional Patent Application No. 63/201,250, filed Apr. 20, 2021, which is incorporated, in its entirety, by this reference.

BACKGROUND

Prior approaches to tissue resection with an energy source can be less than ideal in at least some respects. Work in relation to the present disclosure suggests that the prior approaches can cut tissue with less accuracy and can be somewhat more invasive than would be ideal in at least some instances. At least some of the prior approaches may position an energy source with less accuracy than would be ideal, which can lead to less than ideal tissue resection. Although robotics approaches can provide positioning with computer control, at least some of the prior robotics systems may not position a treatment element as accurately as would be ideal. Also, other factors such as tissue variability and movement can make the prior approaches less than ideal in at least some instances. Although treatments with more than one energy source have been proposed, the prior approaches may provide less than ideal coordination and positioning with more than one treatment probe in at least some instances.

SUMMARY

The presently disclosed probes, systems and methods provide improved placement of energy sources. In some embodiments, an energy source is offset from an elongate probe axis with an extension. The amount of offset of the energy source can be controlled by varying an amount of offset of the extension. The energy source can be offset by a distance, and the energy source rotated and translated at the offset distance to resect tissue. In some embodiments, the probe is configured to receive a second treatment probe comprising a second energy source, in which the second energy source is rotated and translated relative to the first treatment probe, which can improve positional accuracy and stability. In some embodiments, the energy source and the extension are coupled to a linkage to offset the energy source, and to translate and rotate the energy source with varying amounts of offset. In some embodiments, the first and second energy sources are configured to move independently.

In some embodiments, the linkage is coupled to a processor and one or more of the energy sources moved in accordance with a treatment profile. In some embodiments, the probe is configured to engage a plurality of drive elements of a robotic arm to move the one or more energy sources. In some embodiments, the robotic arm comprises five or more drive elements, and the probe is configured to offset the energy source, rotate the energy source, translate the energy source, rotate the second energy source, and translate the second energy source with coupling to the five or more elements of the robotic arm.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 7 shows a probe comprising an energy source with variable offset from an elongate axis of the probe, in accordance with some embodiments;

FIG. 8 shows a probe as in FIG. 7 in a compact configuration with the energy source positioned toward an elongate axis of the probe, in accordance with some embodiments;

FIGS. 12A and 12B show top and side views, respectively, of a probe comprising a variable offset energy source configured for manual use, in accordance with some embodiments;

FIGS. 16A to 16C show an energy source coupled to a surface follower with a pivot near a surface of the tissue follower, in accordance with some embodiments;

FIGS. 17A to 17C show an energy source coupled to a surface follower with a variable extension depth of the energy source from the follower to the tissue, in accordance with some embodiments;

FIG. 18A shows deflection of a bendable link to deflect the energy source with interlocking structures to provide rotational stability, in accordance with some embodiments;

FIG. 18B shows a cross-sectional view of the probe as in FIG. 18A, in accordance with some embodiments;

FIG. 18C shows a bottom view of the probe of FIGS. 18A to 18B, in accordance with some embodiments;

FIG. 18D shows deflection of the probe of FIGS. 18A to 18C with a deflection angle greater than 45 degrees from an elongate axis of the probe, in accordance with some embodiments;

DETAILED DESCRIPTION

Figure 1:
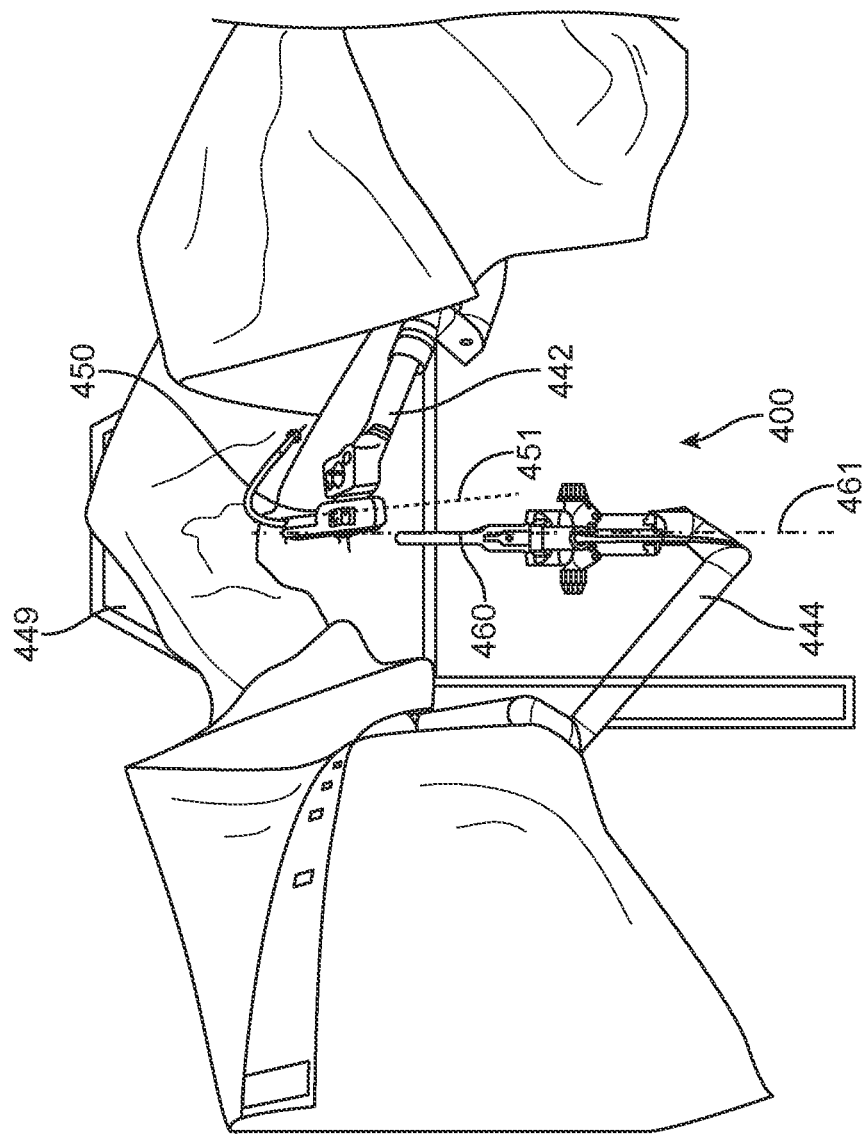
FIG. 1 shows a front view of a system for performing tissue resection in a patient, in accordance with some embodiments of the present disclosure.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for use with many probes and diagnostic and surgical procedures. Although reference is made to a probe comprising an energy source for prostate surgery, the present disclosure is well suited for use with many types of probes inserted into many types of tissues, cavities and lumens, such as vascular lumens, nasal lumens and cavities, urethral lumens, gastric lumens, airways, esophageal lumens, trans esophageal, intestinal lumens, anal lumens, vaginal lumens, trans abdominal, abdominal cavities, kidney surgery, ureter surgery, kidney stones, prostate surgery, tumor surgery, cancer surgery, brain surgery, heart surgery, eye surgery, conjunctival surgery, liver surgery, gall bladder surgery, bladder surgery, spinal surgery, orthopedic surgery arthroscopic surgery, liposuction, colonoscopy, intubation, minimally invasive incisions, minimally invasive surgery, and others.

The presently disclosed systems and methods are well suited for combination with prior probes such as imaging probes and treatment probes. Examples of such probes include laser treatment probes, water jet probes, RF treatment probes, radiation therapy probes, ultrasound treatment probes, phaco emulsification probes, imaging probes, endoscopic probes, resectoscope probes, ultrasound imaging probes, A-scan ultrasound probes, B-scan ultrasound probes, Doppler ultrasound probes, transrectal ultrasound probes, sagittal plane ultrasound imaging probes, transverse plane ultrasound imaging probes, and transverse and sagittal plane ultrasound imaging probes, for example.

The presently disclosed systems, methods and apparatuses are well suited for combination with many prior surgical procedures, such as water jet enucleation of the prostate, transurethral resection of the prostate (TURP), holmium laser enucleation of the prostate (HOLEP), and with surgical robotics systems and automated surgical procedures. The following patent applications describe examples of systems, methods, probes and procedures suitable for incorporation in accordance with the present disclosure: PCT/US2013/028441, filed Feb. 28, 2013, entitled "AUTOMATED IMAGE-GUIDED TISSUE RESECTION AND TREATMENT, published as WO 2013/130895; PCT/US2014/054412, filed Sep. 5, 2014, entitled "AUTOMATED IMAGE-GUIDED TISSUE RESECTION AND TREATMENT", published as WO 2015/035249; PCT/US2020/021756, filed Mar. 9, 2020, entitled "ROBOTIC ARMS AND METHODS FOR TISSUE RESECTION AND IMAGING", published as WO/2020/181290; PCT/US2020/058884, filed on Nov. 4, 2020, entitled "SURGICAL PROBES FOR TISSUE RESECTION WITH ROBOTIC ARMS", published as WO/2021/096741; PCT/US2021/070760, filed on Jun. 23, 2021, entitled "INTEGRATION OF ROBOTIC ARMS WITH SURGICAL PROBES", published as WO/2021/263276; and PCT/US2021/038175, filed on Jun. 21, 2021, entitled "SYSTEMS AND METHODS FOR DEFINING AND MODIFYING RANGE OF MOTION OF PROBE USED IN PATIENT TREATMENT", published as WO/2021/262565; the entire disclosures of which are incorporated herein by reference.

In some embodiments, improved positional accuracy is provided for placement of an energy source. The energy source may comprise any suitable energy source, such as an electrode, a loop electrode, laser source, mechanical sheer, ultrasound probe, cavitating ultrasound probe, a water jet, e.g. a fixed pressure water jet, plasma, steam, a morcellator, a trans urethral needle, photo ablation, water jet evacuation. The energy source can be combined with other treatments and compounds, such as photochemical treatment agents.

The probe comprising the energy source can be configured in many ways and may comprise a force sensor to detect tissue resistance and to adjust one or more of the energy source deflection angle or an amount of energy in response to the measured tissue resistance.

FIG. 1 shows an exemplary embodiment of a system 400 for performing treatment of a patient. The system 400 may comprise a treatment probe 450 as described herein and an imaging probe 460 as described herein. The treatment probe 450 may be coupled to a first arm 442, and the imaging probe 460 coupled to a second am 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
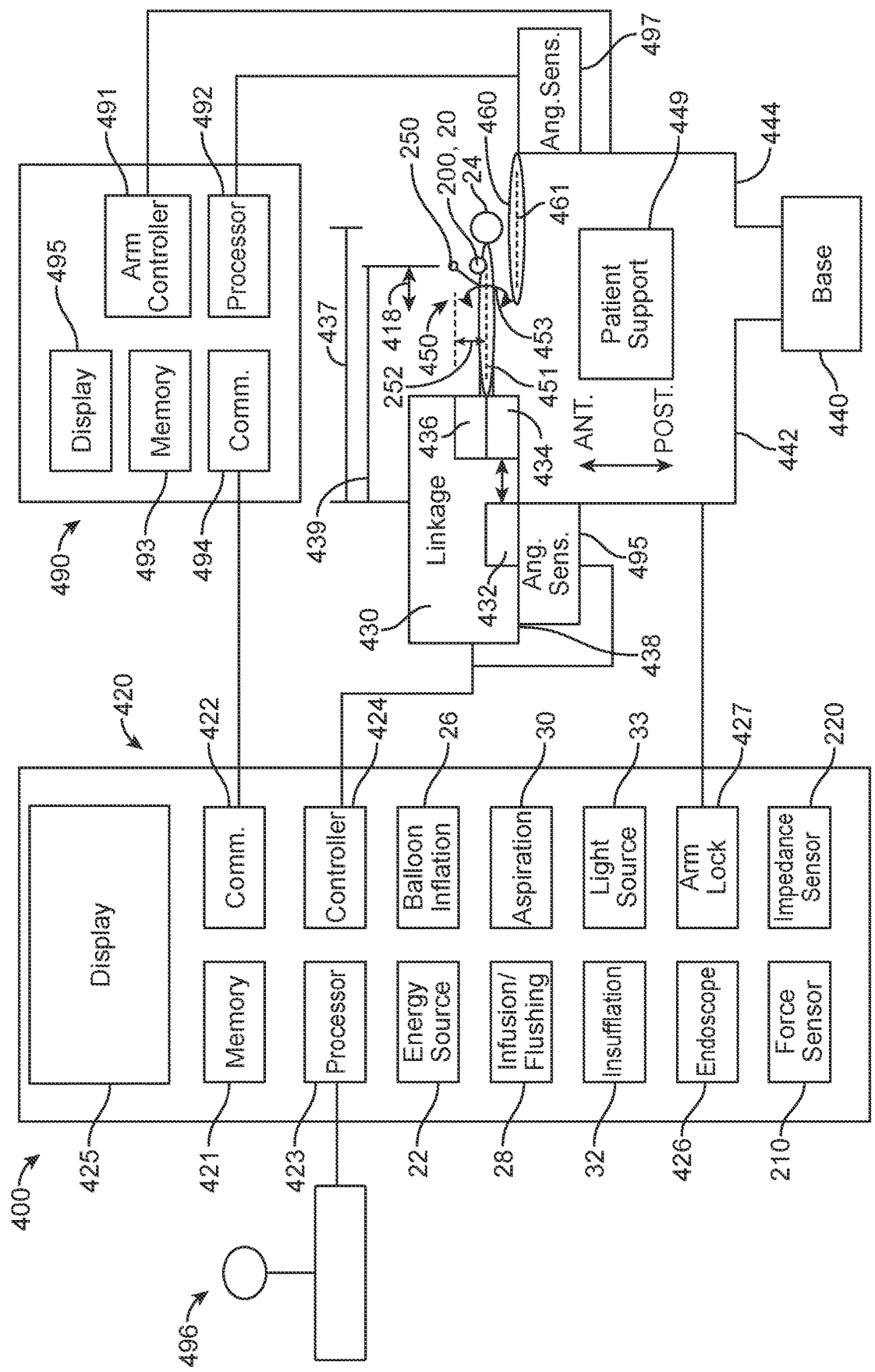
FIG. 2 schematically illustrates a system for performing tissue resection in a patient, in accordance with some embodiments of the present disclosure.

FIG. 2 schematically illustrates embodiments of the system 400 for performing tissue resection in a patient. The system 400 may comprise a treatment probe 450 as described herein and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image data of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

In some embodiments, the console 420 comprises impedance sensor circuitry 220 coupled to the energy source to measure impedance of tissue treated with energy from the energy source. In some embodiments, the energy source comprises an electrode and the electrode comprises an impedance sensor. In some embodiments, the processor is configured with instructions to adjust an amount of energy from the energy source in response to an amount of impedance. In some embodiments, the processor is configured with instructions to adjust an amount of deflection of the extension and offset of the energy source from the elongate axis in response to impedance.

In some embodiments, the console 420 comprises force sensor circuitry 210 coupled to a force sensor on the treatment probe. The force sensor can be coupled to the extension to measure tissue resistance related to deflection of the extension, for example. In some embodiments, the force sensor is coupled to the link to measure tissue resistance related to movement of the energy source away from the elongate axis. In some embodiments, the force sensor is coupled to the energy source to measure tissue resistance related to a positioning distance of the energy source from the elongate axis. In some embodiments, the force sensor is configured to measure tissue resistance related to an amount of energy delivery from the energy source.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. In some embodiments, the probe comprises a first energy source 250 that can be offset from the elongate axis 451 of the probe with an offset distance 252 to treat tissue, for example with deflection of an extension as described herein. The processor can be configured with instructions to perform 3D volumetric resection of the tissue with rotation, translation and offset of the energy source 250 in response to computer control. The probe 450 may comprise a second energy source as described herein such as a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed at a substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the second energy source such as high-pressure nozzle 200 in the energy delivery region 20 at a desired axial position along an elongate axis 451 of treatment probe 450. Additional actuators and linkages can be provided and operatively coupled to the processor to offset, rotate, and translate the first energy source 250 as described herein.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust with translation 418 of the probe in response to computer control to set a target location along the elongate axis 451 of the treatment probe. In some embodiments, the first portion of the linkage remains fixed, while the second portion 434 adjusts the position of the energy delivery region 20 along the axis 451. The third portion 436 of the linkage adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, one or more of the treatment probe or the imaging probe may be coupled to a robotic, computer-controllable arm. For example, referring to system 400 shown in FIG. 2, one or both of the first arm 442 coupled to the treatment probe 450 as described herein and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figure 3B:
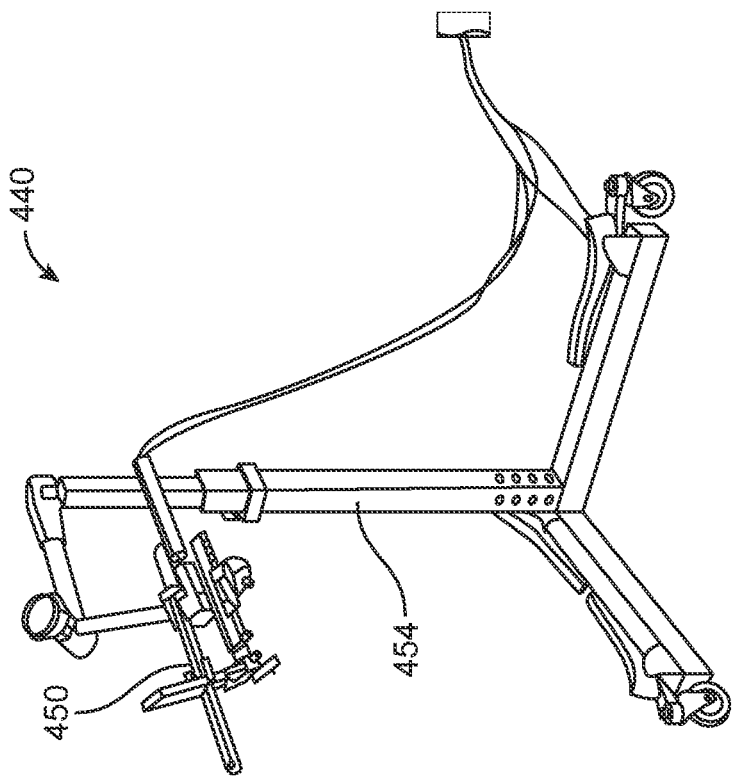
FIGS. 3A and 3B show perspective views of a common base or mount for supporting one or more robotic arms, in accordance with some embodiments of the present disclosure.
Figure 3A:
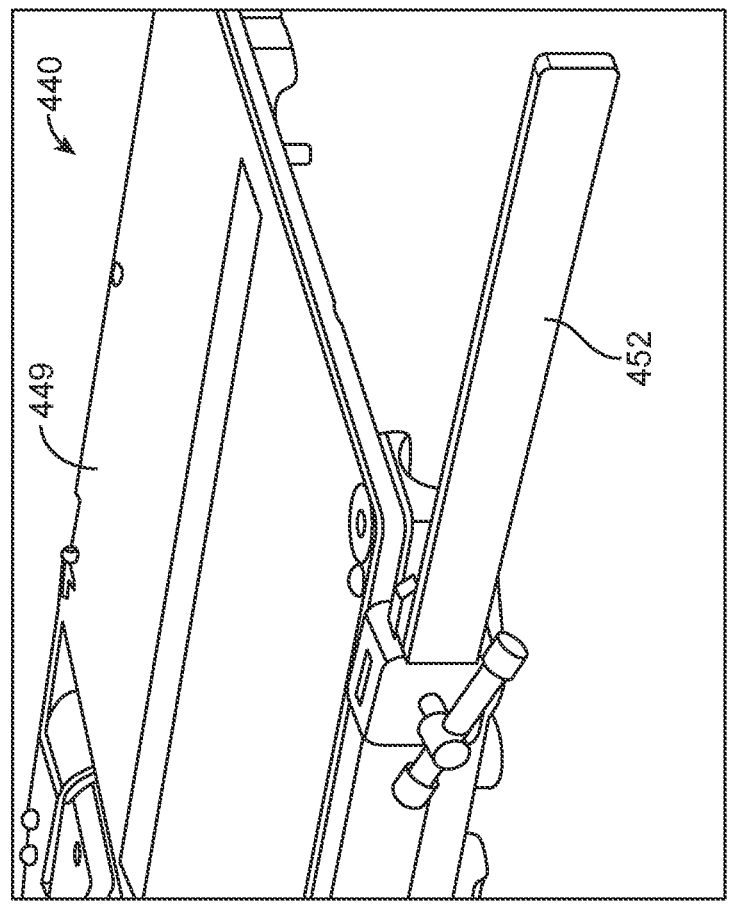

FIGS. 3A and 3B show exemplary embodiments of a common base or mount 440 for supporting one or more robotic arms of an image-guided treatment system as disclosed herein, and the treatment system may comprise probe 450 as described herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
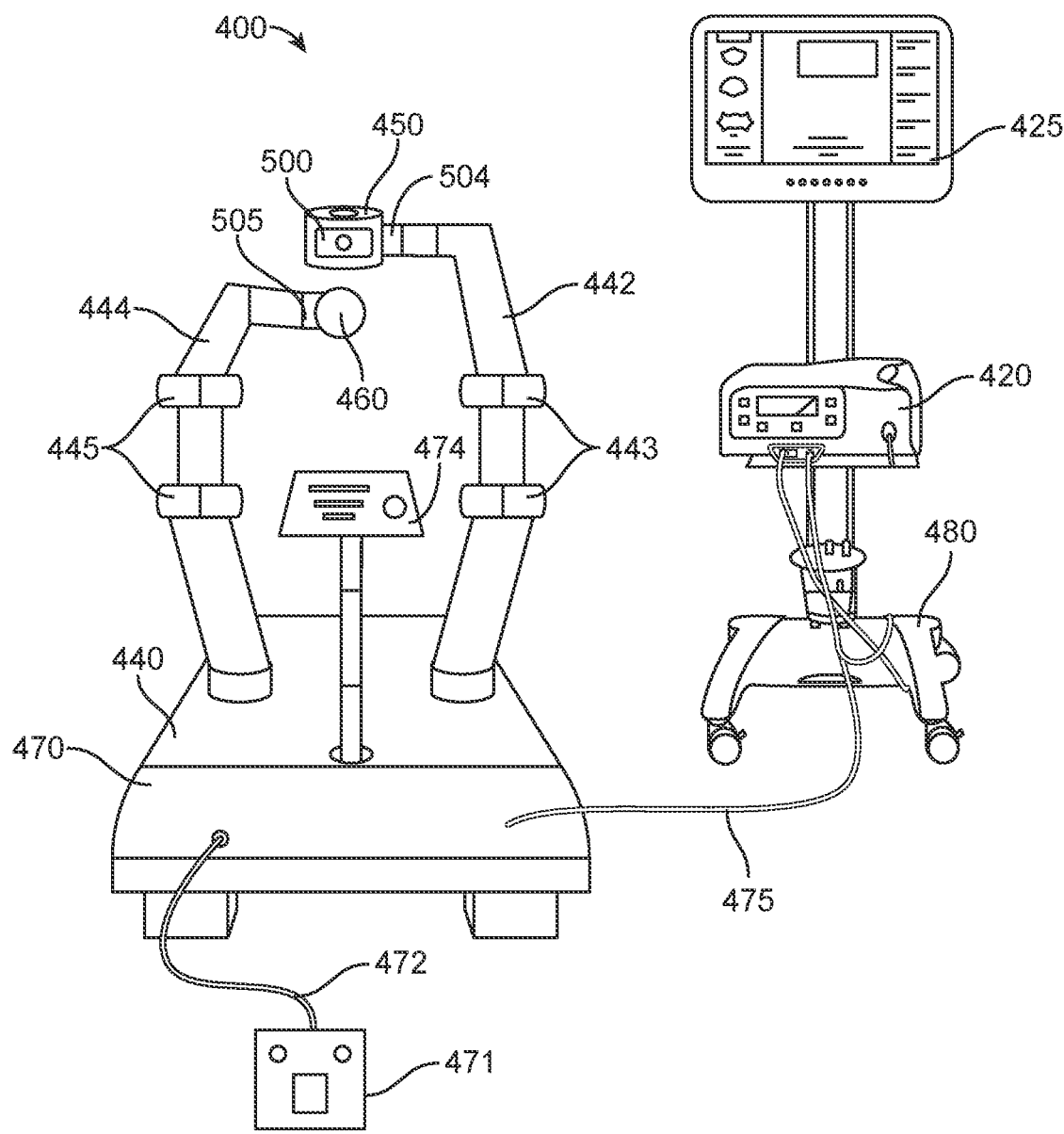
FIGS. 4A and 4B illustrate a perspective and side view, respectively, of a system for performing tissue resection in a patient that comprises a mobile base, in accordance with some embodiments of the present disclosure.
Figure 4B:
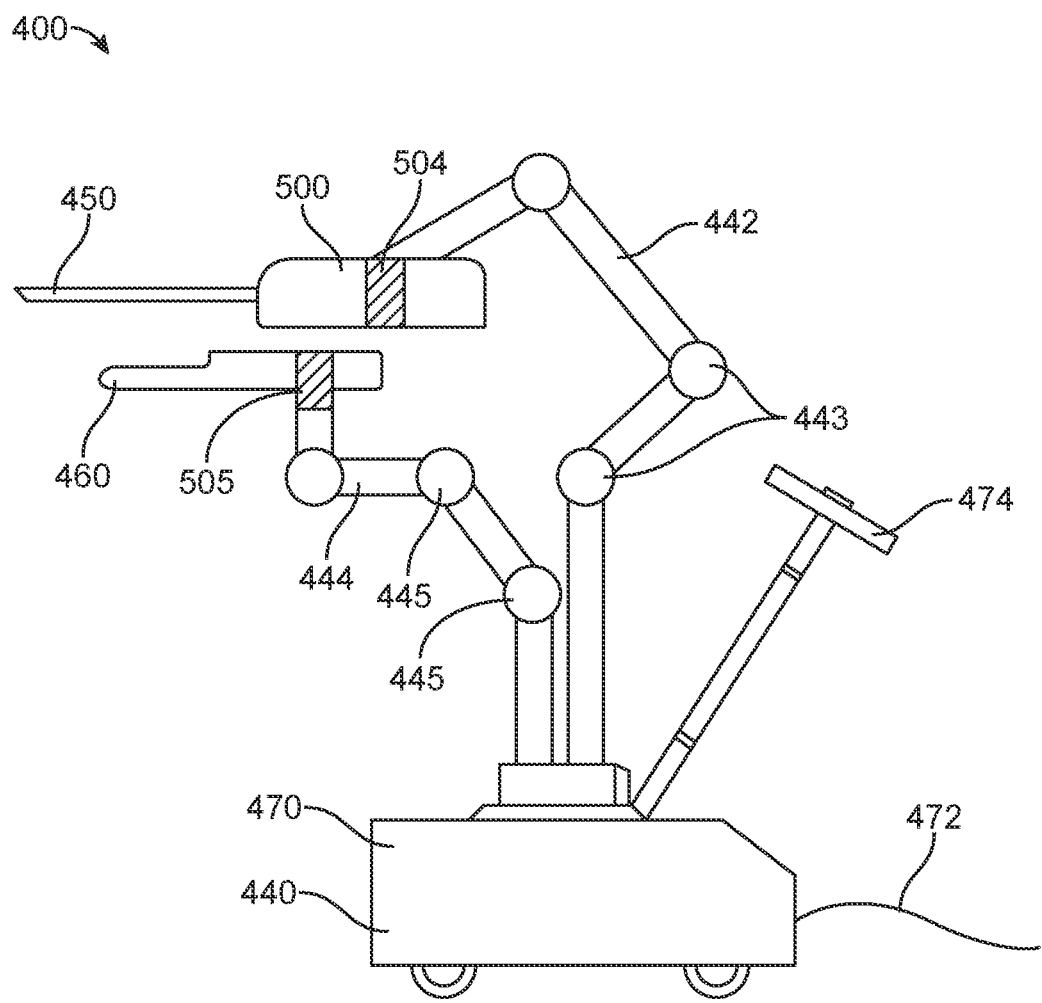

FIGS. 4A and 4B illustrate embodiments of a treatment system 400 as described herein comprising a mobile base 470. FIG. 4A is a front view and FIG. 4B is a side view of the treatment system 400. The treatment system 400 may comprise a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 444 may comprise a second arm coupling structure 505 to couple to the imaging probe 460. The treatment probe 450 may be coupled to the distal end of the first robotic arm 442 via an attachment device 500, which may comprise a linkage configured to affect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each joint 443 or 445 may be operably coupled with a computer-controllable actuator, such as a stepper motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a processor and a memory having stored thereon computer-executable instructions for execution by the processor, to control various modules or functionalities of the treatment console, such as an energy source, infusion/flushing control, aspiration control, and other components as described herein with reference to FIG. 2. The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or more computing devices to control operation of the one or more robotic arms. For example, the mobile base may comprise processors and a memory having stored thereon computer executable instructions for execution by the one or more processors. The memory may have stored thereon instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

Figure 5A:
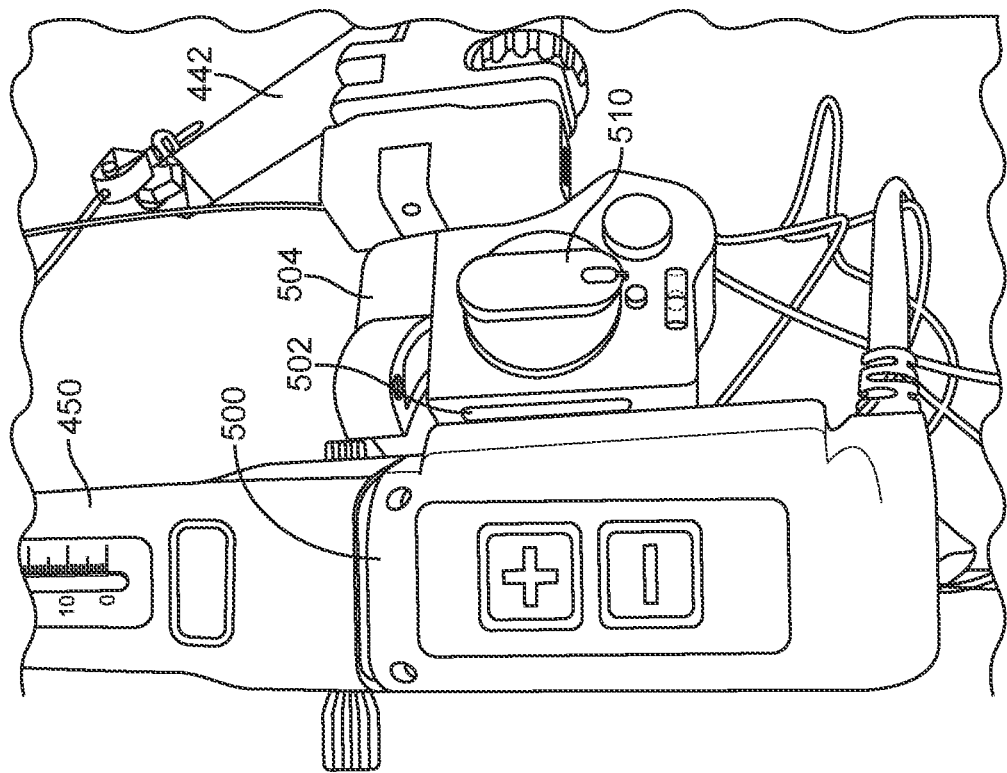
FIGS. 5A and 5B show top views of a coupling between a treatment probe and a first robotic arm, with FIG. 5A showing the treatment probe and the first robotic arm uncoupled and FIG. 5B showing the treatment probe and the first robotic arm coupled, in accordance with some embodiments of the present disclosure.
Figure 5B:
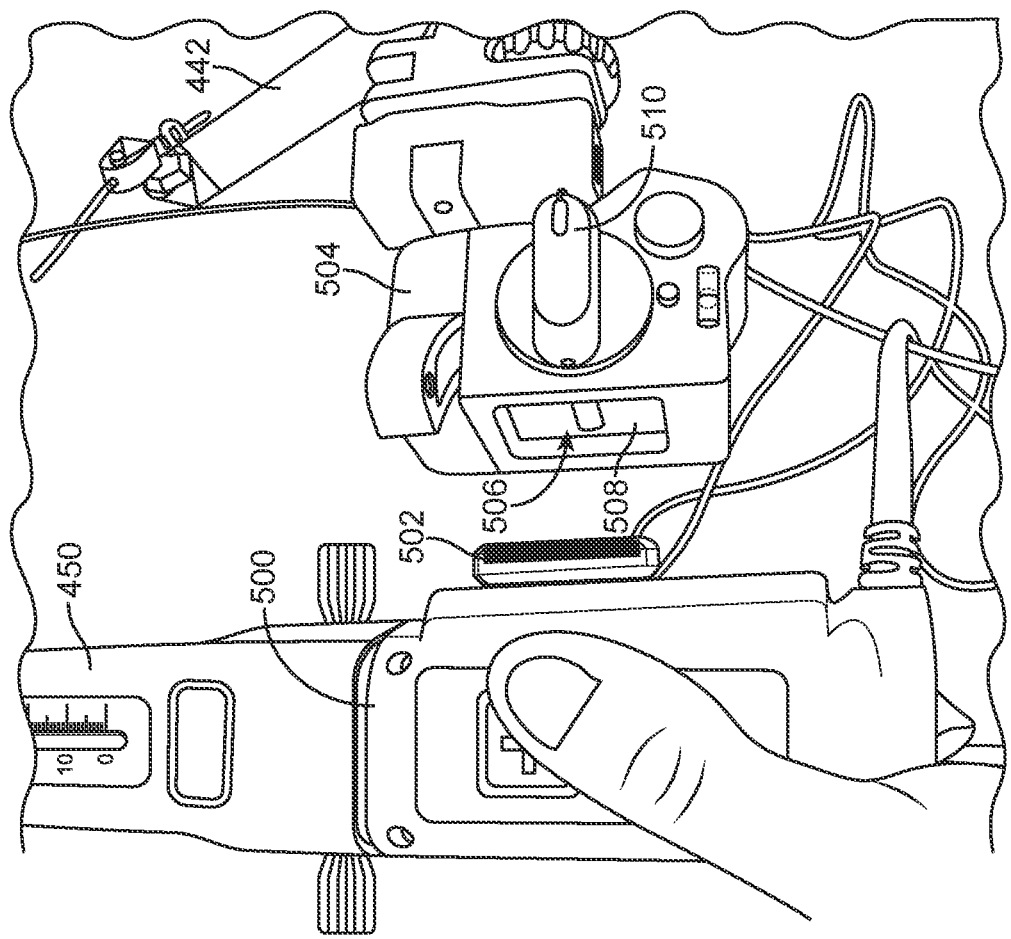

FIGS. 5A and 5B show an exemplary coupling between a treatment probe 450 as described herein and a first robotic arm 442. FIG. 5A shows the treatment probe uncoupled from the robotic arm. FIG. 5B shows the treatment probe coupled to the robotic arm. As shown, the treatment probe 450 may be coupled to the robotic arm 442 with an attachment device 500 which may comprise a reusable motor pack. The treatment probe 450 may be removably coupled to the attachment device 500. The attachment device may further comprise a connector 502 configured to couple to the robotic arm and lock the attachment device in place. The robotic arm 442 may comprise a coupling structure 504 disposed at the distal end of the arm, configured to lockingly receive the connector 502 of the attachment device 500. Once the treatment probe and the robotic arm are coupled together, movement of the treatment probe may be controlled by moving the robotic arm (e.g., by articulating one or more joints of the robotic arm under computer control).

In some embodiments, the treatment probe is coupled to the robotic arm via a quick release mechanism, such that the coupling between the probe and the robotic arm is capable of a quick disconnect in order to prevent injury to the patient in case the robotic arm loses position or otherwise fails to operate correctly. The treatment probe and the robotic arm may be coupled to one another in many ways such as mechanically (e.g., a broom clip) and/or magnetically. For example, in the embodiment shown in FIGS. 5A and 5B, the coupling structure 504 may comprise a slot 506 having a magnet 508 disposed therein, and the connector 502 may comprise a ferromagnetic fixture configured to fit within the slot 506 to engage the magnet 508. The coupling structure 504 may further comprise a latching mechanism 510 to selectively engage or disengage the connector 502 with the magnet 508. For example, as shown in FIGS. 5A and 5B, the latching mechanism 510 may comprise a rotatable knob that can be rotated to affect engagement of the magnet 508 of the coupling structure 504 with the connector 502 of the attachment device 500. The latching mechanism may be automatically or manually engaged or disengaged by a user to couple or de-couple, respectively, the attachment device 500, and hence the treatment probe 450 coupled thereto, to the robotic arm 442. In some embodiments, the coupling structure 504 may be operably coupled with the one or more computing devices configured to control the robotic arm, and the one or more computing devices may comprise instructions to release the coupling of the coupling structure to the probe when an error is detected in the operation of the robotic arm.

In some embodiments, the first robotic arm 442 may be configured to automatically locate the treatment probe 450 in response to sensor location data from one or more of the attachment device 500 or coupling structure 504. The first robotic arm 442 may be operated in a "seek" mode, for example, to locate the attachment device 500. In some embodiments, the probe comprises one or more fiducial targets and the robotic arm comprises corresponding sensors of sufficient resolution and positioning to identify the relative position of the probe in 3D space. In some embodiments, the processor is configured with instructions to seek the treatment probe or imaging probe with the mounting structures on the robotic arm while the user holds the probe steady, for example when the probe has been positioned in the patient.

The sensors on the robotic arm such as the first robotic arm 442 and sensors on the probe such as the treatment probe can be arranged in many ways, for example as described in PCT/US2020/021756, filed Mar. 9, 2020, entitled "ROBOTIC ARMS AND METHODS FOR TISSUE RESECTION AND IMAGING", published as WO/2020/181290, which has been previously incorporated herein by reference.

The processor can be coupled to the sensors near the end of the robotic arm or on the probe to dynamically update the relative location during the movement of the robot arm while seeking to engage the probe on the arm. The sensors on the robotic arm may comprise a plurality of sensors comprising one or more of capacitive, capacitive displacement, doppler, inductive, magnetic, optical, radar, sonar, ultrasonic or Hall effect sensors, in order to determine relative distances between the robotic arm and the probe. In some embodiments the probe comprises a plurality of targets and the sensors are configured to generate signals in response to distances from the plurality of targets. Alternatively or in combination, the sensors can be located on the probe and the targets on the robotic arm. In some embodiments, the sensors comprise close contact mechanical sensors to confirm docking of the probe on the robotic arm or in proximity to the arm, for example to sense the position of the probe in relation to the robotic arm when the probe and arm are within a few millimeters of docking with each other. The close contact mechanical sensors may comprise one or more of micro-motion switches, whisker touch sensors, or a pin-in-hole contact switch. In some embodiments, the probe and robotic arm comprise an integrated locking mechanism to provide a non-movement locking engagement at the final position of contact. The integrated locking mechanism may comprise one or more of magnetics, electromagnetics, a latching, screw such as a multi turn latching screw or quarter turn locking screw, a vacuum, or other mechanical means of reversible attachment as will be understood by one of ordinary skill in the art.

In some embodiments, a plurality of sensors is used, such as one or more sensors for near, one or more sensors for intermediate separation distances and one or more sensors for far separation distances between the probe and the robotic arm. A coarse location sensor can be used to determine the approximate location of the probe, e.g. a beacon. One or more sensors can be used for fine location positioning of the probe in relation to the robotic arm, e.g. proximity sensors. In some embodiments, one or more markers on the probe are used with a camera and machine vision detection of the one or more markers.

In some embodiments, coarse location sensors may be provided which may be an infrared (IR) beacon which enables the coarse positional spatial location for homing detection of the robotic arm to the probe. In some cases, a homing beacon, such as an IR beacon, allows for homing across larger distances as compared to a sensor that may rely on visual recognition of fiducials.

In some embodiments, a docking detection sensor confirms that the robotic arm has engaged or is in close proximity with a probe. As an example, a Hall effect sensor can be used in conjunction with a permanent magnet to affect the sensors output. In some embodiments, a Hall effect sensor is noise immune, non-contact, and has a consistent detection range. Any of a number of different types of Hall sensors may be utilized, and in many cases, the sensor functions as a simple switch and linear range measurement and detection in which the overall output voltage is set by the supply voltage and varies in proportion to the strength of the magnetic field. This results in a distance measurement between the sensor and a locating magnet and may be used to measure the distance between the robotic arm and the probe and aid in docking. The sensor and beacon may be located within respective housings of the robotic arm and probe.

In some embodiments, positional sensing of the robotic arm is performed by an inertial measurement unit (IMU), which may include up to 9-axis detection. In some cases, a 6-axis IMU can be used for motion detection, vibration detection, positional orientation information, redundancy and backup of the primary encoder signals that may be located in the joints of the robotic arms. The IMUs may perform a dual function of seeking a probe for docking with the robotic arm as well as force detection and motion compensation as described herein. The described sensors can be used in combination with any robotic arms or probes described herein.

According to some embodiments, the procedure for docking a robotic arm with a probe may comprise an IR beacon to provide coarse positional and spatial location for homing detection, fiducials on either the arm or the probe and an optical sensor to view the fiducials which can be used to allow fine alignment of positional location in the XY plane, and a Hall effect sensor to detect Z direction proximity for docking. An IR beacon allows for larger distance seek for the home position of the robotic arm relative to the probe. The fiducials and optical sensor may allow for rapid, low-latency detection of the 2D location and 2D orientation of the probe by the robotic arm. A user interface, which may be located on the robotic arm, on the probe, or on a robotic arm control unit, may indicate distance, position, docked status or other information. In some embodiments, the user interface includes one or more visual cues, such as LED indicators, to indicate the relative position and/or docking status of the arm and probe.

While the coupling mechanism shown in FIGS. 5A and 5B is described in the context of coupling the treatment probe to the first robotic arm, a substantially similar mechanism may also be used for coupling the imaging probe to the second robotic arm 444. For example, the coupling structure of the second robotic arm 444 may comprise a similar coupling mechanism for engaging an attachment device connected to the imaging probe.

Figure 6A:
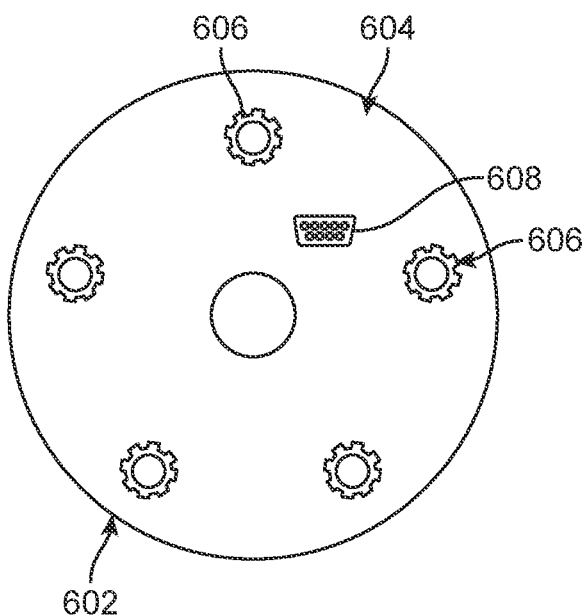
FIG. 6A shows drive elements of a robotic arm to couple to a surgical probe, in accordance with embodiments of the present disclosure.
Figure 6B:
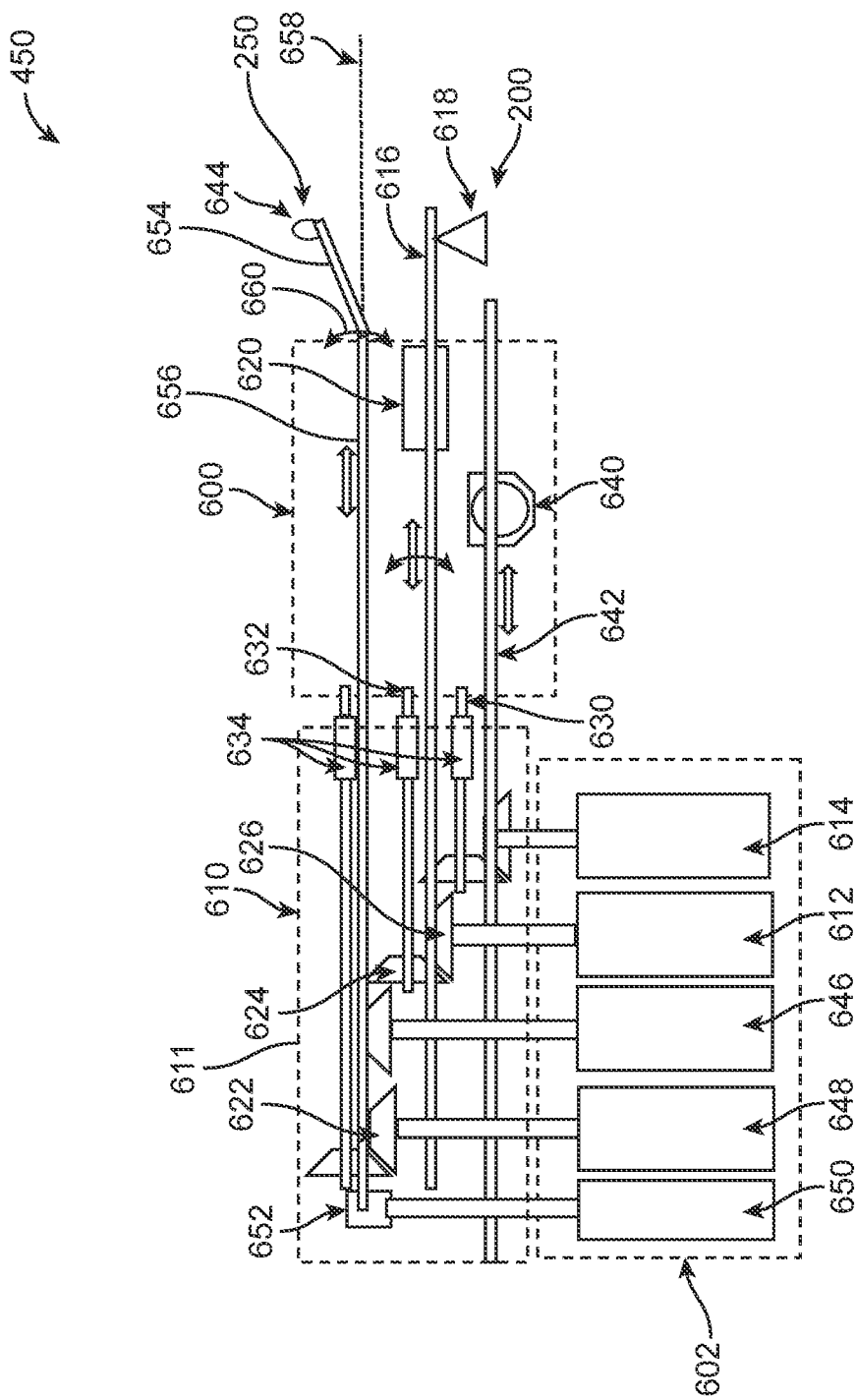
FIG. 6B shows coupling of a robotic arm to a treatment probe, in accordance with some embodiments.

FIGS. 6A and 6B show exemplary couplings between a handpiece 600 and an instrument device manipulator 602. Throughout this description of various embodiments, the handpiece 600 may comprise any of a variety of instruments, such as, for example imaging probes, treatment probes, surgical tools, catheters, energy delivery systems, implants, visualization systems, and other instruments that may be desirable to be used during the diagnosis or treatment of a patient. Also, while reference is made to handpiece 600 coupled to the transmission, the surgical probe coupled to the transmission may comprise any suitable probe as described herein. As used throughout this description, reference to an instrument device manipulator 602 may refer to a robotic arm. The instrument device manipulator 602 may have one or more motors associated therewith, which may be carried internally or externally to the instrument device manipulator 602. In some embodiments, an instrument device manipulator 602 may carry one, two, three, four, five, six, seven, eight, or more motors. One or more of the motors may have an output shaft that is turned rotationally by the motor. One or more of the motors of the instrument device manipulator 602 may comprise a linkage (e.g., gear) on the output shaft of the motor. The linkage may comprise a pinion gear, a bevel gear, a spur gear, a helicoid gear, a worm drive gear, a planetary gearset, or some other type of linkage. The linkage may be coupled to another linkage, a chain, a belt, or some other type of transmission 610 linkage associated with the transmission 610 to transfer the rotational motion of the motor into motion of one or more parts of the handpiece 600. In some cases, the rotational motion of the motor is transferred to rotational motion of a component of the handpiece 600, while in some cases, the rotational output of the motor is transferred to linear motion of a component of the handpiece 600. The following figures provide exemplary systems for coupling an instrument device manipulator 602 to one or more instruments, such as a handpiece 600, a probe, a scope, or other instrument.

FIG. 6A shows an exemplary end 604 of an instrument device manipulator 602, having five linkages 606 and an electrical port 608. While the illustrated embodiment shows five linkages 606, it should be appreciated that the instrument device manipulator 602 may have any suitable number of linkages 606, such as two, three, four, five, six, seven, eight, nine, or more. While the linkages 606 are shown as gears, any type or combination of suitable linkages 606 may be used. Examples of linkages for rotational motion include, but are not limited to, round shafts with flats, round shafts with keyway slots, square or rectangular shafts, spline couplings, pentagonal shafts, hexagonal shafts, and the like. Linkages 606 may also provide translational motion. The electrical port 608 may provide electrical power and communication to the handpiece 600, such as for allowing signals to pass between the handpiece 600 and a computing device that may implement a treatment plan and control the actuation of the instruments of the handpiece 600. In some embodiments, the hand piece comprises one or more of a force sensor, force sensor circuitry, or impedance measurement circuitry coupled to an electrode, and the electrical port 608 is configured to receive and transmit one or more of impedance signals or force measurement signals.

In some embodiments, each of the plurality of linkages 606 comprises an output of the instrument device manipulator 602, which output comprises an engagement structure to couple to a corresponding engagement structure of the input to the transmission as described herein. In some embodiments, the engagement structure and the corresponding engagement structure comprise rotatable engagement structures, such as one or more of a pinion gear, a bevel gear, a spur gear, a helicoid gear, a worm drive gear, a gear of a planetary gearset, a shaped shaft, round shafts with flats, round shafts with keyway slots, square or rectangular shafts, spline couplings, pentagonal shafts, hexagonal shafts, and corresponding structures as described herein.

FIG. 6B shows an exemplary coupling between a handpiece 600 and an instrument device manipulator 602. The handpiece 600 may comprise a treatment probe 450 to deliver energy from a first energy source 250 and a second energy source 200 as described herein. In some embodiments, the handpiece 600 and treatment probe 450 are configured to receive a second treatment probe comprising a second energy source as described herein. A transmission 610 couples the handpiece 600 to the instrument device manipulator 602 and transfers the output from one or more motors 612, 614, etc., associated with the instrument device manipulator 602 to the handpiece 600. In some embodiments, the transmission 610 is configured to be decoupled from the instrument device manipulator 602 and the probe, e.g. handpiece 600, in a free-standing configuration of the transmission 610 with the housing 611 at least partially enclosing the transmission. The transmission 610 may include speed reduction or speed multiplication to couple efficiently between one or more motors 612 of the instrument device manipulator 602 and the R-drive, Z-drive, or both of the handpiece 600 or one or more implements carried by the handpiece, such as, without limitation, an imaging device, a cutting tool such as a water jet, an electrode such as an RF electrode, or other energy delivery device. In some cases, a transmission 610 can be configured to couple several configurations of handpiece 600 to an instrument device manipulator 602. For instance, a transmission 610 can be configured to receive the output from one or more motors 612 associated with the instrument device manipulator 602 and transfer the motion to any of a variety of handpieces 600. In this way, a handpiece 600 does not need to be manufactured to couple with a specific instrument device manipulator 602, but rather, because the transmission 610 can be configured to couple with both, the handpiece 600 and its associated instruments can be manufactured without regard to the instrument device manipulator 602 that it may ultimately be coupled to.

With any of the numerous embodiments disclosed herein, the transmission 610 may be at least partially enclosed, e.g. encased, in a housing 611 that covers the internal components of the transmission 610. The housing 611 may comprise any suitable housing, such as a plastic housing that encases the transmission internal workings and is shown in dotted line throughout the figures. In some cases, an output from the instrument device manipulator 602 passes through the housing to couple to an input of the transmission 610. The output of the instrument device manipulator comprises an engagement structure to couple to a corresponding engagement structure of the input of the transmission, which engagement structures may comprise any suitable shape as described herein and generally comprise rotatable structures. Similarly, an output from the transmission 610 may extend through the housing in order to couple with the handpiece 600, in which the output of the transmission and the input of the handpiece comprise corresponding engagement structures to couple the handpiece to the transmission as described herein.

Similarly, an input of the instrument device manipulator 602 may extend through the housing in order to couple with the instrument device manipulator 602, e.g. with a corresponding engagement structure. Likewise, an input from the handpiece 600 may extend through the housing 611 in order to mechanically couple to the transmission 610, e.g. with a corresponding engagement structure.

In any event, one or more of an output or an input may pass through the housing 611 in order to effectuate coupling between the instrument device manipulator 602, the transmission 610, and/or the handpiece 600. In some cases, the instrument device manipulator 602 comprises one or more outputs which may extend through the housing. The transmission may include one or more inputs that extend through the housing and/or one or more outputs that may extend through the housing. Similarly, the handpiece 600 may comprise one or more inputs that extend through the housing of the transmission 610.

The handpiece 600 may comprise any suitable treatment probe 616, such as a waterjet 618 for example, an RF electrode 644, or other treatment probe and is coupled to the instrument device manipulator 602 with an attachment device which may comprise a reusable transmission 610. A reusable transmission 610 may offer advantages as mechanical and electrical precision can be built into the device with a minimal impact on the cost of a single procedure. The handpiece 600 may be removably coupled to the transmission 610 and the transmission 610 may be removably coupled to the instrument device manipulator 602. Removable couplings promote interchangeability of similar devices and give the surgeon the ability to quickly and easily change between instruments of different types in response to medical imperatives. The handpiece 600 may comprise a position encoder 620 that is configured to send a signal associated with the position of the one or more treatment probes 616, 644. The signal may correspond to the rotation angle, position, orientation, translation, or a combination of the treatment probes 616, 644. Additional encoders 620 may be provided to send signals associated with the position or orientation of other instruments, such as an imaging probe, endoscope, catheter, laser, microwave, and others. Similarly, one or more encoders may be provided in conjunction with the instrument device manipulator 602 to determine the position and orientation of the instrument device manipulator 602.

The transmission 610 may comprise a connector configured to couple the instrument device manipulator 602 to lock the transmission 610 in place to the instrument device manipulator 602. The instrument device manipulator 602 may comprise a coupling structure disposed at the distal end of the arm, configured to rigidly receive the connector of the transmission 610. Similarly, an additional coupling structure may be provided between the transmission 610 and the handpiece 600. Once the handpiece 600 and the instrument device manipulator 602 are coupled together by the transmission 610, movement of the handpiece 600 may be controlled by moving the instrument device manipulator 602 (e.g., by articulating one or more joints of the instrument device manipulator 602 under computer control, or under manual control, or actuating one or more motors of the instrument device manipulator 602).

In some embodiments, the handpiece 600 is coupled to the transmission 610 by a quick release mechanism, such that the coupling between the handpiece 600 and the transmission 610 is capable of a quick disconnect in order to prevent injury to the patient in case the instrument device manipulator 602 loses position or otherwise fails to operate correctly. The quick release mechanism may also facilitate changing handpiece 600s and instruments quickly, even during a procedure where it is desirable to attach alternative instruments to the instrument device manipulator 602 by way of the transmission 610.

Similarly, the transmission 610 may be coupled to the instrument device manipulator 602 through a similar mechanism, which may provide for a quick release. The coupling of the handpiece 600 to the transmission 610 and the transmission 610 to the instrument device manipulator 602 may be carried out by a similar connecting structure or may be different structures. For instance, the handpiece 600 may couple to the transmission 610 by a magnetic coupling while the transmission 610 may couple to the instrument device manipulator 602 by a mechanical locking structure. Other coupling structures may include a slot having a magnet disposed therein and a cooperating ferromagnetic fixture can be configured to fit in the slot. The couplings may be provided by a latching mechanism to selectively engage or disengage the cooperating coupling member. Further, the coupling structure may comprise a rotating knob, a lever, a cooperating boss and pocket, a hook, a latch, a pin, or some other suitable type of connector to releasably secure the handpiece 600 to the transmission 610 and the transmission 610 to the instrument device manipulator 602.

As illustrated, the instrument device manipulator 602 may have two motors 612, three motors, four motors, five motors or more. The right-angle transmission linkages 622 shown in FIG. 6B may be preferable geometrically in some cases pertaining to the arrangement of the linkages of the arm which supports the instrument device manipulator 602. A first motor 612 has an output shaft carrying a linkage, such a bevel gear, a worm gear, a helicoid gear or some other configuration. The first motor 612 is coupled to a cooperating linkage of the transmission 610. The transmission 610, in turn, is coupled to an instrument, such as a waterjet 618, and provides for rotational motion of the instrument. In some embodiments, the instrument comprises a distal end and a proximal end, and a lumen extending between the distal end and the proximal end. The distal end may carry an energy source such as a nozzle, and the proximal end may be coupled to a source of high-pressure fluid. In some cases, the instrument is maintained substantially straight as it is carried by the transmission 610. In some cases, the instrument fits within a groove formed on the outside of the transmission 610 to facilitate quick insertion and removal of the instrument with the transmission 610. The instrument may be retained by a retaining structure carried by the transmission 610, such as a clip, a lever, or some other suitable structure.

A second motor 614 of the instrument device manipulator 602 has an output shaft that carries a linkage, which may be a bevel gear 622, a worm drive, a helicoid gear, or some other suitable gear. The second motor 614 is coupled to a cooperating gear of the transmission 610. The transmission 610 is, in turn, coupled to an instrument, such as the waterjet 618, and is used to provide translational linear motion of the instrument. In some instances, the transmission 610 comprises a step-up transmission 610, in which the rotational output of the transmission 610 is faster than the rotational input of the transmission 610. This may be accomplished, for example, by a driven gear 624 having a smaller pitch circle than a driving gear 626. In some embodiments, the driven gear 624 has a smaller number of gear teeth compared to the driving gear 626. Alternatively, the transmission 610 may be step-down transmission 610, in which a driven gear 624 has a larger pitch circle than a meshed driving gear 626. In such cases, the driven gear 624 may have more teeth than the driving gear 626 which causes it to rotate slower than the driving gear 626.

In some embodiments, the first motor 612 and the second motor 614 of the instrument device manipulator 602 are coupled to a single input of the transmission 610. For example, two or more motors of the instrument device manipulator 602 may be coupled together within the transmission 610 to combine their power into a single output shaft. Additionally, the transmission 610 may take the two or more motors and through gearing or other leveraging mechanics, cause the output shaft to step down the input from the two or more motors to result in greater combined torque, or step up the input from the two or more motors to result in greater speed. A step-down transmission 610 may be useful where torque is preferred to speed, such as for applying a clamping force. A step-up transmission 610 may be useful where speed is preferred over torque, such as for ultrasonic motion, burr cutting, friction heating, or other suitable high-speed process.

The transmission 610 may comprise a right-angle transmission 610 wherein the output shafts of the instrument device manipulator 602 motors is orthogonal (or substantially orthogonal) to the input shafts of the handpiece 600. For expediency in describing the various configurations, the handpiece 600 has a longitudinal axis and the treatment probe 616 (e.g., water jet) runs parallel to the longitudinal axis of the handpiece 600, which is also referred to as the Z-direction. An X-Y plane is orthogonal to the Z-direction. In some embodiments, the water jet is translated in the Z-direction by the second motor, also referred to as a Z-drive 630, and is rotated about its longitudinal axis by a rotational motor ("R-drive") 632. The treatment probe 616 translates longitudinally and/or oscillates rotationally under instructions by a computing device. The computing device sends signals to the instrument device manipulator 602 to actuate one or more motors 612 that are coupled to the instruments of the handpiece 600 by linkages. The handpiece 600 has one or more encoders 620 that send signals back to the computing device, such as location, position, orientation, translation, or some other signal indicative of a parameter of the handpiece 600, or one or more instruments of the handpiece 600.

The handpiece 600 may couple to the transmission 610 in such a way as to mechanically couple the R-drive 632 and the Z-drive 630 with the instruments of the handpiece 600. For example, the transmission 610 may include a coupler 634, such as a hex-shaft coupler, that receives a corresponding shaped structure of the handpiece 600, such that when the handpiece 600 is coupled to the transmission 610, the instruments of the handpiece 600 are in driving engagement with the transmission 610. Other couplers are contemplated, and include, without limitation, round couplers with flats, round couplers with keyway slots, square or rectangular couplers, spline couplers, pentagonal couplers, and the like. Accordingly, the motors of the instrument device manipulator 602 are coupled to the transmission 610, which transfers the motion of the instrument device manipulator 602 motors to the instruments of the handpiece 600. Once coupled, activation of the instrument device manipulator 602 motors results in R-drive or Z-drive motion of the instruments of the handpiece 600.

In some embodiments, an input from the instrument device manipulator 602 may provide for articulation of one or more instrument of the handpiece 600. For example, an instrument, such as a probe, scope, or other device, may be flexible, have segments, joints, or have other ways of allowing articulation of the instrument. An input from the instrument device manipulator 602 may be used to articulate the instrument, such as, for example, by manipulating a wire, such as by tensioning, twisting, compressing, or some other applied force. Instruments of the handpiece 600 may be rotated, translated, articulated, or a combination of movements in response to applied forces from the instrument device manipulator 602.

As an example, the handpiece 600 may carry an energy source as described herein such as an energy delivery electrode, which in some cases may be an RF electrode 644. A third motor 646 of the instrument device manipulator 602 may be coupled to the RF electrode 644 through the transmission to linearly translate the RF electrode 644. A fourth motor 648 may be coupled to the RF electrode 644 and configured to provide rotation of the RF electrode 644. A fifth motor 650 may be coupled to the RF electrode 644 through the transmission and may be used to pivot the RF electrode 644 in a direction away from the longitudinal axis of the RF electrode. In other words, at least a portion of the RF electrode 644 may pivot, articulate, hinge, and/or bend such that the distal end of the RF electrode 644 is not coaxial with a proximal length of the shaft. Such an articulation allows the distal tip of the RF electrode 644 to be moved in closer proximity to tissue that is spaced apart from the longitudinal axis of the RF electrode 644 in order to resect tissue with one or more of rotation and translation of the electrode as described herein.

According to some embodiments, the RF electrode 644 is mounted to an extension 654 that is pivotally coupled to a shaft 656 at pivot 660. In some cases, the shaft 656 is driven by one or more motors 646, 648 to allow the shaft to translate linearly and/or rotate about the axis 658 of the shaft. The extension 654 may be coupled to the shaft 656 through any suitable connection (e.g., pivot 660) that allows the extension 654 to move away from the shaft axis 658. The extension 654 may be moved by any suitable actuator, such as a motor, a pull wire, a thermal input, a gear, a shaft, or any other such suitable actuator mechanism.

The fifth motor 650 may be coupled to the RF electrode 644 through any suitable coupling 652, and may include one or more gears, a wheel, a driver, a push and/or pull wire, or other such structure that can be configured to articulate at least a portion of the RF electrode 644. The RF electrode 644 may be coupled to a suitable source of energy such as for providing an RF signal to the RF electrode. The source of energy may be delivered through the transmission 610, by the handpiece 600, or through some other electrical connection.

The RF electrode 644 may be coupled to an RF generator, such as by a wire extending along or within the shaft 656. Current may be delivered to the RF electrode 644 and passed through the tissue before returning to the RF generator. The current delivered by the RF electrode 644 rapidly decreases with the fourth power of distance from the RF current source, and thus the delivered power is absorbed into a very small volume of tissue to be treated. According to some embodiments, the RF electrode 644 may be translated, rotated, and/or pivoted away from the axis of the shaft 656 in order to move the RF electrode 644 into close proximity to tissue to be treated.

In some embodiments, the shaft 656 carries a microwave ablation apparatus, which may include a power distribution system, an interstitial applicator that may be coupled to a microwave generator. A microwave ablation system may be structured and operated similarly to the RF electrode 644 as described herein.

An electrical system interface device 636 may be carried by the transmission 610 and can transmit, condition, or interpret electrical signals between the instrument device manipulator 602 and the handpiece 600. The electrical system interface device 636 may include one or more electrical connectors to electrically couple the handpiece 600 and the instrument device manipulator 602 when the handpiece 600 is coupled to the instrument device manipulator 602 by the transmission 610. The electrical system interface device 636 may send electrical power and/or commands to the handpiece 600, such as from a computing system, and may send signals from the handpiece 600 to the instrument device manipulator 602, such as signals associated with force, imaging, volume, position, direction, orientation, temperature, or some other parameter. It may also provide signal processing between the handpiece 600 and the instrument device manipulator 602, as well as signals passing to and from system 400. In some embodiments, the handpiece 600 comprises one or more encoders 620 for sending a signal associated with a parameter of the handpiece 600 to the computing system. It may also send electrical energy to one or more of the probes such as for energizing lights, RF emitters, thermal ablation devices, or other devices that require electrical power for efficient operation.

An imaging device, such as a cystoscope 642, ultrasound probe, or other type of imaging device, may be carried by the handpiece 600, and may be manually positioned by a manual position control device 640, or may be under control of one or more motors for positioning such as translation and/or rotation.

FIGS. 7 to 11 show different views and configurations of a treatment probe.

Figure 9:
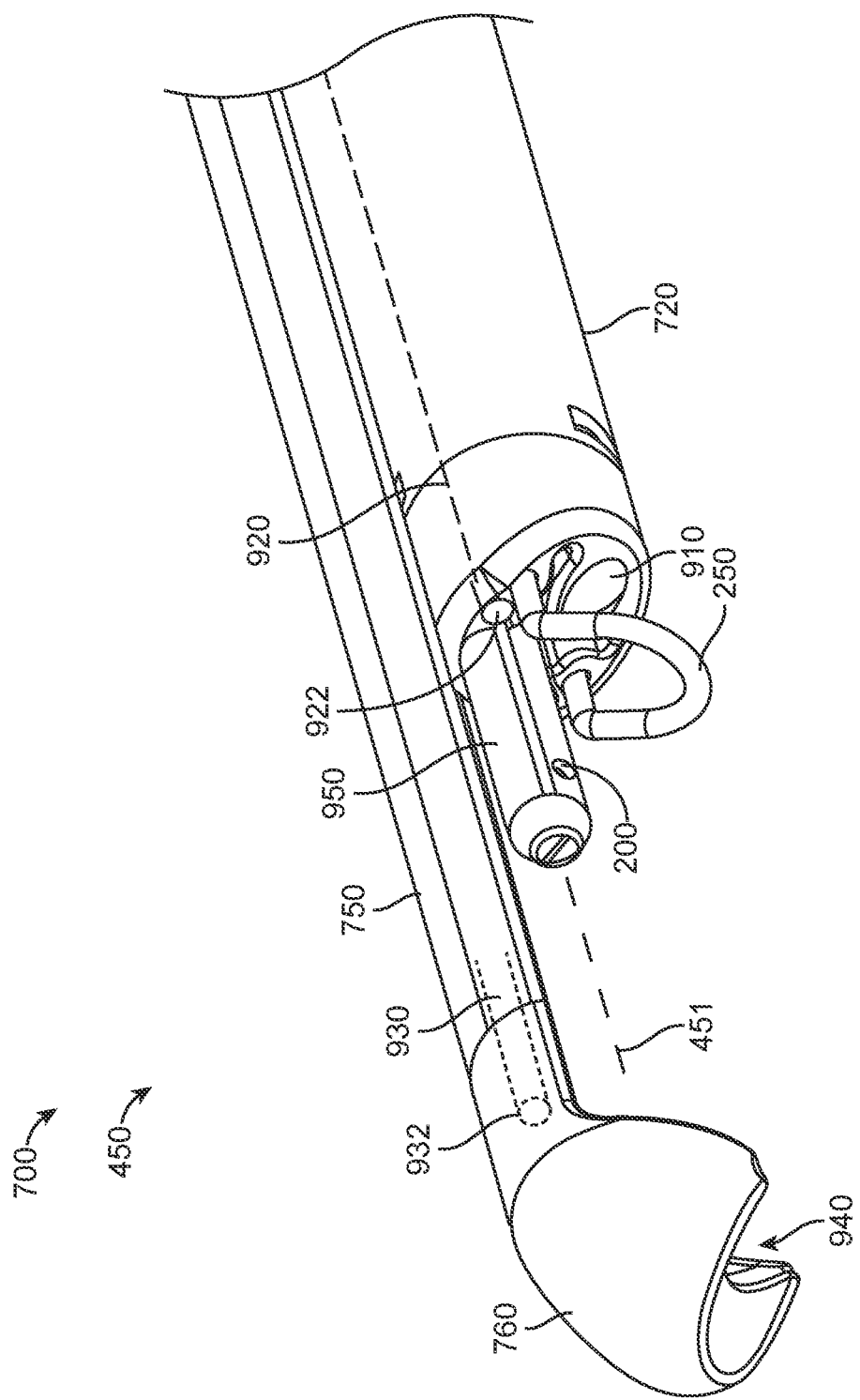
FIG. 9 shows an isometric view of the probe as in FIGS. 8 and 9 in the compact configuration, in accordance with some embodiments.

FIG. 7 shows a probe comprising an energy source with variable offset from an elongate axis of the probe. FIG. 8 shows a probe as in FIG. 7 in a compact configuration with the energy source positioned toward an elongate axis of the probe. FIG. 9 shows perspective view of the probe as in FIGS. 7 and 8 in the compact configuration. FIG. 9 shows additional components of the probe as in FIGS. 7 and 8, in which the probe comprises a digital endoscope, and active irrigation ports. The probe can be coupled to computer-controlled actuators to provide automated 3D tissue rejection, or manual actuators, or both, for example. In some embodiments, the movement may comprise automated treatment in response to images shown on a display, and sequential treatment with an energy source as described herein, such as a water jet, and an electrode to cauterize tissue.

FIGS. 7 to 9 show a treatment probe 700 and configurations of the treatment probe to treat tissue with a deflectable energy source. The treatment probe 700 may comprise one or more components of treatment probe 450 and can be coupled to robotics systems or a handle as described herein. The energy source 250 is configured to move away from an elongate axis 451 of the probe 700 to provide an offset 252 from axis 451. The probe 700 comprises a link 710 coupled to an extension 720. The extension 720 is coupled to energy source 250 as described herein. In some embodiments, a shaft 730 is coupled to link 710, and shaft 730 is configured to rotate and translate to rotate and translate extension 720 and energy source 250. In some embodiments, shaft 730 is located within a sheath 740 that allows rotational and translational movement of shaft 730 within sheath 740. The shaft 730 may comprise a single or component shaft or a shaft comprising a plurality of shafts to provide additional movements of the energy source as described herein. In some embodiments, probe 700 comprises a spine 750 to add stiffness, for example. In some embodiments, the spine 750 extends to a rounded distal tip, or to an anchor as described herein. In some embodiments, spine 750, shaft 730 and sheath 740 are located within a second sheath 742.

In some embodiments, the link 710 is coupled to one or more linkages to provide an offset 252 to energy source 250 from axis 251. The offset 252 can be provided in many ways such as with a deflection 254 of extension 720, or translation of extension 720, in order to move the energy source 250 away from axis 451 and back toward axis 451. The energy source 250 can be moved with translation 418 or rotation 453 and combinations thereof. The extension 720 and energy source 250 can be rotated and translated with corresponding rotational and translational movement of shaft 730.

In some embodiments, probe 700 is configured with a narrow profile configuration as shown in FIG. 8 for insertion into tissue. Once inserted, the extension 720 can be moved to offset energy source 250 from elongate axis 451, such that probe 450 comprises a wide profile configuration. In some embodiments, the shaft 730 is configured to move with translation 418 over a working distance 731 dimensioned to allow resection of target tissue over a suitable distance. In some embodiments, the working distance is within a range from about 0.5 cm to about 10 cm. The offset 252 and rotation 453 can be similarly dimensioned to allow tissue resection over the suitable distance and provide volumetric tissue removal. In some embodiments, the extension is configured to deflect to move the energy source toward and away from the elongate axis with an offset distance from the axis of no more than 5 cm. In some embodiments, the sheath comprises a cross-sectional diameter within a range from 3 mm to 12 mm and optionally within a range from 4 mm to 10 mm.

While the probe 700 can be configured in many ways, in some embodiments, the link 710 is configured to deflect the energy source 250 from a first position near the elongate axis 451 as shown in FIG. 8 toward a second position away from the elongate axis 451 as shown in FIG. 7, in which the first position, the second position and the link substantially define a plane extending through the sheath 742. In some embodiments, the plane extends through the drive shaft 730 coupled to the energy source 250 to one or more of offset, rotate or translate the energy source relative to the shaft. In some embodiments, the elongate axis 451 of the probe extends along the drive shaft 730 to rotate the energy source about an axis of the drive shaft, which can provide improved positional accuracy of the energy source. In some embodiments, an axis of rotation of the energy source about the elongate axis 451 of the probe is coaxial with an axis of rotation of the drive shaft. In some embodiments, the drive shaft 730 comprises a tube and an axis of rotation of the energy source about the elongate axis 451 of the probe extends along an interior of the tube.

The presently disclosed probe is well suited for use with surgical robotics and hand manipulated systems to provide improved placement of the energy source in relation to the elongate probe with the components described herein. In some embodiments, the energy source can be offset from the elongate axis 451 of the probe with a positional accuracy tolerance of 1 mm or less, and optionally with a positional accuracy tolerance of 0.25 mm or less. In some embodiments, the energy source can be rotated around the elongate axis of the probe with a rotational accuracy tolerance of 1 degree or less, and optionally with a rotational accuracy tolerance of 0.5 degrees or less. In some embodiments, the energy source can be translated with respect to the elongate axis of the probe with a translational accuracy tolerance of 1 mm or less, and optionally with a translation accuracy tolerance of 0.25 mm or less. The positional accuracy, the rotational accuracy and the translational accuracy are related to movements of the probe near the proximal end, such as movement provided by motors near the proximal end of the probe. In some embodiments the positional accuracy, the rotational accuracy and the translational accuracy each corresponds to a limited deviation from a corresponding proximal movement such as a rotation or a translation provided by a linkage as described herein.

The components of probe 700 can be configured in many ways to provide suitable amounts of stiffness, in accordance with some embodiments. Work in relation to the present disclosure suggests that adding stiffness to one or more components of the probe can provide improved rotational stability and resistance to torsional forces. The stiffness of the one or more probe components may comprise one or more of a bending stiffness or a torsional stiffness, for example. The stiffness may comprise a combined stiffness of the probe, or one or more components of the probe, such as the tubular drive shafts as described herein. In some embodiments, the torsional stiffness of the probe or the one or more elements of the probe is within a range from 10 Nm/radian to 125 Nm/radian. Alternatively or in combination, the bending stiffness of the probe or the one or more components of the probe is within a range from 200 to 2000 N/m. The stiffness of the individual components of the probe can be calculated by one of ordinary skill in the art of mechanical engineer with equations or with computational methods such as finite element analysis, and combinations thereof.

In some embodiments, torsional stiffness can be determined with the following equation:

$$\text{Torsional stiffness} = \frac{G\pi(D^4 - d^4)}{32L}, \text{ where}$$

-continued $G$ = shear modulus of elasticity, $D$ = outside diameter, $d$ = inside diameter, $L$ = Length, Gpa = Giga Pascals, N = Newtons, m = meters, and mm = millimeters.

While the material may comprise any suitable material such as a metal, steel, stainless steel or plastic, in some embodiments, the shaft comprises stainless steel, such as 304 stainless steel comprising a shear modulus of elasticity of 200 Gpa, for example. The dimensions of the one or more components may comprise any suitable dimensions corresponding to dimensions of the probe as described herein, such as L=300 mm, D=8 mm, and d=7 mm, which provides a torsional stiffness of approximately 110 Nm/radian for example. In another example, the dimensions of the one or more probe elements have dimensions of D=6 mm, d=5.8 mm, which provides a torsional stiffness of 11 Nm/radian. Although reference is made to a component with a length of 300 mm, the length may comprise any suitable length, for example within a range from about 100 mm to about 400 mm. The stiffness within the above ranges may comprise a stiffness of the probe between the energy source and a proximal linkage component coupled to a motor, such as a gear for example as described herein with reference to FIG. 6B.

In some embodiments, bending stiffness can be determined with the following equations:

$$\text{Bending Stiffness} = \frac{3EI}{L^3},$$

$$\text{For a hollow tube } I = \frac{\pi(D^4 - d^4)}{64},$$

and

Wherein E=Modulus of Elasticity and I=second moment of area.

A person of ordinary skill in the art can determine the bending stiffness for the hollow tube with similar dimension and parameters to those described above, in which the bending stiffness is within a range from about 200 N/m to 2000 N/m. The combined stiffness of the probe can be determined from the stiffness of the components as described herein, for example.

In some embodiments, the sheath 742 comprises stiffness to add rigidity and stabilize the energy source 250 with movement of the elongate shaft 730 and movement of the energy source relative to the sheath. In some embodiments, the spine 750 is coupled to the sheath to add stiffness to the probe. In some embodiments, the spine 750 extends distally beyond the energy source 250. The spine may comprise a tube comprising one or more of a fluid supply channel or a fluid removal channel coupled to one or more openings 932 distal to the energy source to provide a fluid or remove material generated by the energy source. In some embodiments, the spine comprises first side comprising a concave surface facing toward the energy source and spaced apart from the energy source and a second side comprising a convex surface facing away from the energy source to engage tissue. In some embodiments, the spine extends beyond a distal end of the sheath and the one or more openings are located distally beyond the distal end of the sheath. The spine may extend to a distal tip 760, in which the distal tip comprises a rounded end for insertion of the probe and a recess 940 in the tip to allow fluid to pass around the tip when the tip engages a wall of a lumen.

Although reference is made to a stiff sheath, in some embodiments the sheath comprises a flexible sheath.

The treatment probe 700 can be configured to receive another energy source as shown in FIG. 9. In some embodiments, a first energy source 250 is configured to deflect away from an elongate axis of the probe and a second energy source 200 is configured to direct energy outward, for example to emit energy radially outward away from axis 451, or along axis 451, e.g. with an end fire configuration.

The treatment probe 700 can be configured in many ways. In some embodiments, the treatment probe may comprise a stiff spine 750 to maintain placement of the probe, although the spine 750 may be flexible. In some embodiments, the probe 700 comprises one or more joints to move the energy source away from elongate axis 451 of the probe, e.g. with articulation from one or more joints.

The probe 700 may comprise a fluid supply channel 920 coupled to one or more openings 922 and a fluid removal channel 930 coupled to one or more openings. The probe 700 may comprise one or more openings 932 to remove, e.g. aspirate, tissue products such as tissue resection products, and one or more openings 922 to supply fluid to the energy delivery region. The openings may remain substantially fixed while the energy source 250 moves. In some embodiments, the link 710 comprises an articulating joint coupled to the energy source 250 with extension 720. In some embodiments, energy source 250 comprises a loop electrode. Articulation of the joint can provide displacement of the energy source with a controlled deflection angle, which can provide improved accuracy of tissue, treatment, resection, and cautery.

In some embodiments, the rotation of extension 720 relative to the pivot at link 710, and the translation and rotation of shaft 730 about the elongate axis 451 can provide three-dimensional (3D) volumetric resection of tissue with the probe.

FIGS. 8 and 9 show the treatment probe 700 of FIG. 7, in which a second treatment probe 950 comprising a second energy source 200, e.g. a water jet, has been placed in the treatment probe 700. In some embodiments, the second treatment probe 950 is placed in treatment probe 700 after one or more components of treatment probe 700 has been placed in the patient. In some embodiments, the first energy source (e.g. laser or electrode) is configured to rotate, translate, and offset, e.g. pivot, and the second energy source is configured to translate and rotate, such that the energy sources are controlled with 5 or more degrees of freedom, e.g. from motors on an end of a robotic arm as described herein.

Figure 10:
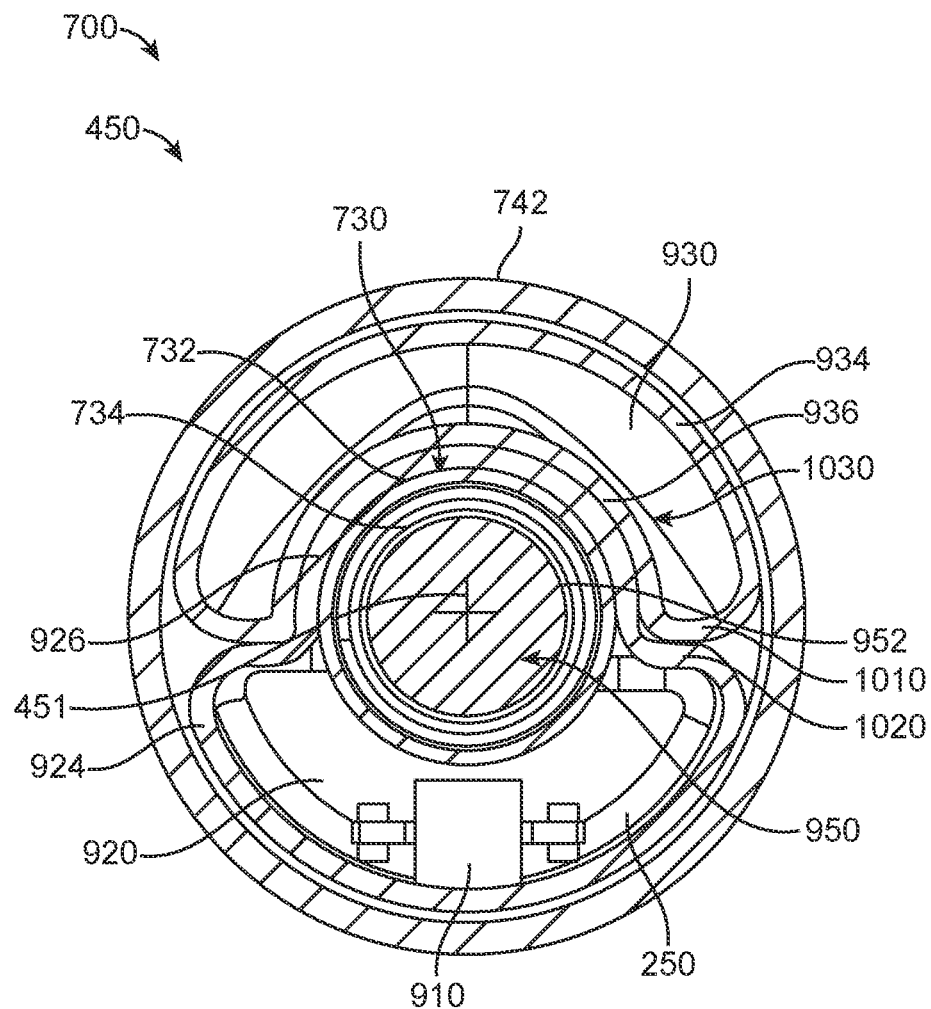
FIG. 10 shows a cross-sectional view of the probe of FIGS. 7 to 9, in accordance with some embodiments.
Figure 11:
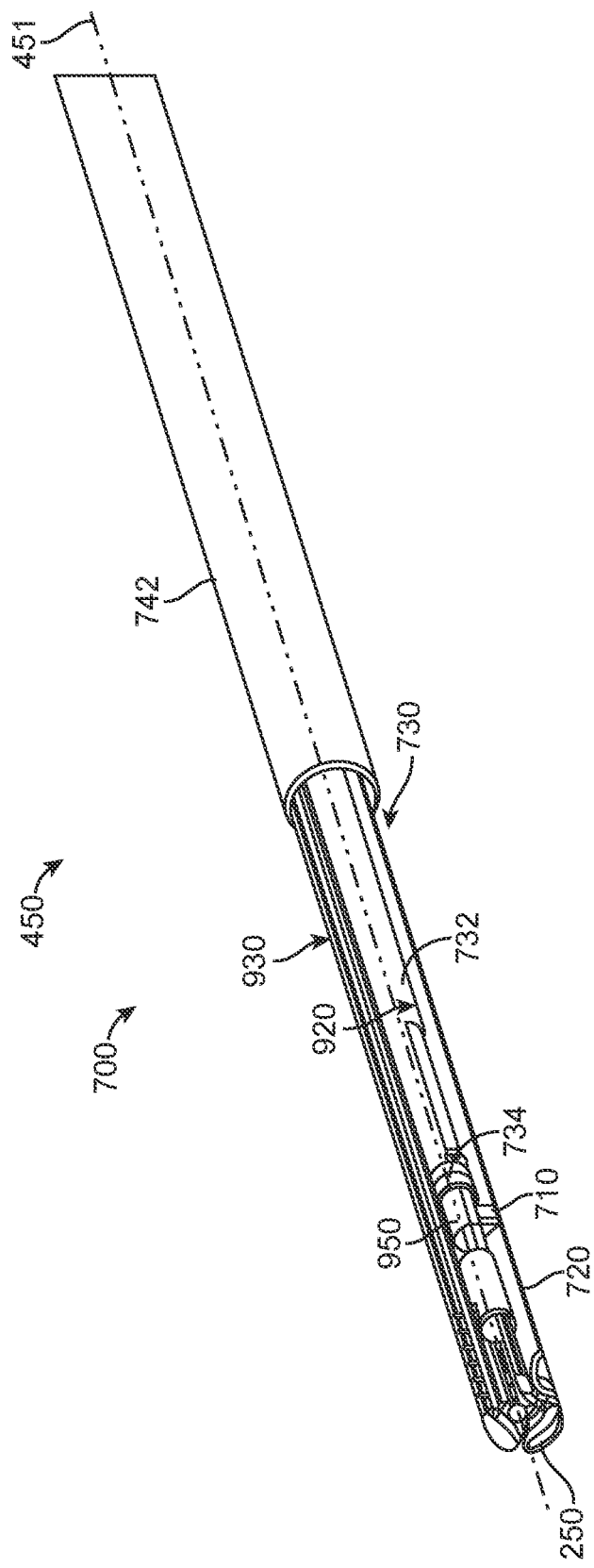
FIG. 11 shows internal drive structures of the probe of FIGS. 7 to 10, in accordance with some embodiments.

FIGS. 10 and 11 show internal and external structures of the probe as in FIGS. 7 to 9. FIG. 10 shows a cross-sectional view of the probe of FIGS. 7 to 9. FIG. 11 shows a perspective view of internal drive structures of the probe of FIGS. 7 to 10. In some embodiments, the probe comprises an outer sheath 742 of suitable diameter, such as a 24 French ("FR") sheath. In some embodiments, fluid removal channel 930, e.g. an aspiration channel, and a fluid supply channel 920, e.g. an irrigation channel, are located within the sheath 742 and extend at least partially around components of shaft 730. In some embodiments, shaft 730 comprises an articulation drive tube 732 for energy source offset and a rotation and translation drive tube 734, e.g. an RF loop drive tube. One or more of the articulation drive tube 732 or the rotation and translation drive tube 734 can be sized and shaped to receive the second treatment probe 950 as described herein, e.g. the water jet probe. The endoscope 910 may comprise a CMOS camera sensor, one or more lenses, and LED light source. While the endoscope 910 can be located in the probe at any suitable location, in some embodiments, the endoscope 910 is located near the end of the drive tubes and fixed with respect to the sheath to view the energy source and extension 720 while extension 720 moves the energy source. Alternatively, the endoscope 910 can be located on extension 720 to place the endoscope in closer proximity to tissue being treated with the energy source, for example.

The diameter of the outer sheath can be sized with any suitable units, such as the diameter in millimeters ("mm") or with the French scale, for example. The French scale size can be readily converted to the diameter in mm, which is approximately ⅓ of the French size. Accordingly, a 24 FR sheath will have a diameter of approximately 8 mm, as will be known to one of ordinary skill in the art.

In some embodiments, the fluid supply channel 920 and the fluid removal channel 930 are located within the sheath 742 to provide improved engagement and rotational stability. In some embodiments, the fluid supply channel 920 comprises one or more of an insufflation channel or an irrigation channel, and the fluid removal channel 930 comprises one or more of a drainage channel or an aspiration channel.

In some embodiments, the fluid supply channel 920 and the fluid removal channel 930 are sized and shaped to engage each other within the sheath 742 with one or more of the fluid supply channel 920 or the fluid removal channel 930 sized and shaped to receive the elongate shaft 730 coupled to the energy source 250 to allow rotation and translation of the energy source 250. In some embodiments, the fluid supply channel 920 is sized and shaped to receive the elongate shaft 730 to provide fluid supply to a surgical site along the fluid supply channel with the elongate shaft 730 placed within the fluid supply channel 920. In some embodiments, the removal channel 930 is sized and shaped to receive the elongate shaft 730 to remove fluid from a surgical site along the fluid removal channel 930 with the elongate shaft 730 placed within the fluid removal channel.

Figure 13A:
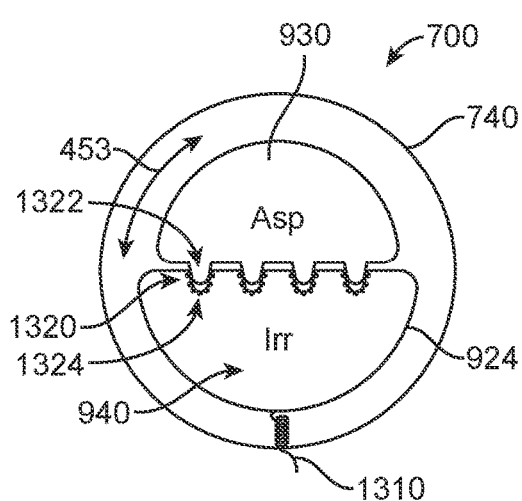
FIGS. 13A to 13C show cross-sectional views of probes comprising asymmetric internal structures to provide rotational stability, in accordance with some embodiments.

The fluid supply channel 920 and the fluid removal channel 930 may comprise tubes configured to engage each other to provide rotational stability. In some embodiments, the fluid supply channel 920 comprises a first tube 924 and the fluid removal channel 930 comprises a second tube 934 and the first tube and the second tube are sized and shaped to engage each other to provide rotational stability while the shaft 730 rotates and translates. In some embodiments, a resilient structure 1310 (as shown in FIG. 13A) is coupled to the sheath 742, the first tube 924, and the second tube 934 to urge the first tube and the second tube toward each other and provide rotational stability. In some embodiments, the first tube 924 comprises a first portion 926 and the second tube 934 comprises a second portion 936 sized and shaped to engage the first portion with a nested configuration. In other words, the first tube 924 may comprise a first portion 926 with a first surface profile and the second tube 934 may comprise a second portion 936 with a second surface profile sized and shaped to engage the first surface profile. In some embodiments, the first surface profile and the second surface profile comprise a curved protrusion and a curved recess to engage each other along an axially extending length of the curved protrusion and the curved recess to provide translational stability. In some embodiments, the first portion 926 and the second portion 936 comprise a plurality of engagement structures 1010, 1020, sized and shaped to engage each other to provide rotational stability. In some embodiments, first portion 926 and the second portion 936 comprise a plurality of interlocking engagement structures 1320 comprising a plurality of protrusions 1322 and a plurality of recesses 1324 sized and shaped to fit together in an interlocking configuration (as shown in FIG. 13A). In some embodiments, the plurality of interlocking engagement structures extends axially along the first tube and the second tube to provide torsional stability to the elongate shaft. In some embodiments, the first tube 924 comprises an outer portion having a third surface profile sized and shaped to engage an interior of the sheath 742 and the second tube 934 comprises an outer portion having a fourth surface profile sized and shaped to engage the interior of the sheath 742. While the sheath can be configured in many ways, in some embodiments the interior of the sheath comprises a circular profile and the third surface profile comprises a circular profile and the fourth surface profile comprises a circular profile.

The shaft 730 can be configured in many ways to offset, rotate and translate the energy source 250. In some embodiments, the elongate shaft 730 comprises a first elongate drive tube 732 to offset the energy source 250 from the elongate axis 451, for example to deflect the extension 720 away from the elongate axis 451. In some embodiments, the elongate shaft 730 comprises a second elongate drive tube 734 to rotate and translate the energy source 250 with the energy source offset from the elongate axis 451, for example with the extension 720 deflected away from the elongate axis.

The first elongate drive tube 732 and the second elongate drive tube 734 can be configured in many ways to move the energy source 250. In some embodiments, the first elongate drive tube 732 and the second elongate drive tube 734 are configured to rotate and translate together to move the energy source 250 with rotation and translation with the energy source offset from axis 451, for example with the extension deflected from the elongate axis. Alternatively or in combination, the first elongate drive tube 732 and the second elongate drive tube 734 are configured to rotate and translate independently to move the energy source 250 with rotation and translation. In some embodiments, the first elongate drive tube 732 and the second elongate drive tube 734 are arranged in a side-by-side configuration (not shown). In some embodiments, the first elongate drive tube 732 and the second elongate drive tube 734 are arranged with one drive tube over the other drive tube. The first elongate drive tube and the second elongate drive tube can be arranged in a coaxial configuration, for example.

In some embodiments, the drive tubes are sized to receive a second probe 950 comprising the second energy source. The first drive tube 732 and the second drive tube 734 are sized to receive the second probe 950 comprising a third drive tube 952 coupled to the second energy source to rotate and translate the second energy source relative to one or more of the first drive tube 732, the second drive tube 734, or the sheath 742.

The first energy 250 source may comprise any suitable energy source, and may comprise one or more of an electrode, a loop electrode, a monopolar electrode, a bipolar electrode, a radiofrequency source, a microwave source, a plasma source, a heat source, a laser source, a mechanical energy source, a mechanical sheer source, a vibrational energy source, an ultrasound energy source, cavitating ultrasound source, a water jet, a fixed pressure water jet, a variable pressure water jet, a water jet evacuation source, a steam source, a morcellator, photo-ablation energy source, an ionizing radiation energy source, a radioisotope, an ionized plasma source, or a cryogenic energy source for example.

Although reference is made to second energy source comprising a nozzle 200, the second energy source may comprise any suitable energy source as described herein, and may comprise one or more of an electrode, a loop electrode, a monopolar electrode, a bipolar electrode, a radiofrequency source, a microwave source, a plasma source, a heat source, a laser source, a mechanical energy source, a mechanical sheer source, a vibrational energy source, an ultrasound energy source, cavitating ultrasound source, a water jet, a fixed pressure water jet, a variable pressure water jet, a water jet evacuation source, a steam source, a morcellator, photo-ablation energy source, an ionizing radiation energy source, a radioisotope, an ionized plasma source, or a cryogenic energy source for example.

In some embodiments, the second energy source 250 comprises the water jet as described herein. In some embodiments, the third elongate drive tube 952 is coupled to a nozzle to generate the water jet. In some embodiments, the third elongate drive tube 952 extends proximally from the nozzle within the first drive tube and the second drive tube to rotate and translate the water jet relative to the first drive tube and the second drive tube.

The endoscope 910 can be configured in any suitable manner. In some embodiments, the digital endoscope comprises a lens and sensor array. Alternatively, the endoscope may comprise a lens and an optical fiber bundle, for example. In some embodiments, the digital endoscope 910 is supported with the extension and the lens and the sensor array move away from the elongate axis with movement of the energy source away from the elongate axis.

FIGS. 12A and 12B show top and side views, respectively, of the probe 700 comprising a variable offset energy source 250 configured for manual use with a handle 1200. In some embodiments the probe comprises manual controls for pivoting of the energy source in response to movement of the manual controls as described herein. The elongate shaft 730 extends proximally toward a handle 1200 to control a rotation angle of the energy source about the elongate axis. In some embodiments, the shaft 730 is coupled to the handle to rotate the energy source with rotation of the handle. The shaft 730 may comprise a linkage extending proximally toward the handle to control an offset distance of the energy source from the elongate axis 451. In some embodiments, the linkage comprises a knob 1230 to control the deflection 254 and corresponding offset distance with rotational movement 1232 of the knob. The handle 1200 may comprise a slider 1220 to move the energy source with translation 418 along the elongate axis 451 with corresponding proximal and distal movement of slider 1220. Alternatively, the linkage can be configured to control the offset distance with slider 1220 and rotational movement 1232 of knob 1230.

In some embodiments, a stiff sheath 742 extends from the handle 1200 to an opening proximal of the link 710 to add rigidity. The shaft 730 can be configured to move within the stiff sheath to translate the energy source 250. A linkage comprising shaft 730 extends between the link and the handle to offset the energy source from the elongate axis with rotation of a knob. In some embodiments, the handle 1200, the shaft 730, and the stiff sheath 742 are configured to move together to rotate the energy source 250 with rotation about the elongate axis 451 with rotation 453.

While the controls of the handle can be configured in many ways, in some embodiments, a finger engagement structure 1210 is configured to engage a finger of a user, and the slider 1220 comprises a thumb engagement structure to engage thumb of a user. The thumb engagement structure is coupled to the shaft to translate the energy source with translation of the thumb engagement structure relative to the shaft.

The extension 720 may comprise a fluid supply channel 920 or a fluid removal channel 930 that extends to one or more openings supported with the extension. In some embodiments, the one or more openings are configured to move with the energy source 250 toward and away from the elongate axis 451 with deflection and straightening of the 710 link.

Although reference has been made to manual articulation, the movement of the energy source can be performed with one or more linkages under computer control, for example combined with a handpiece, as described herein.

Figure 13B:
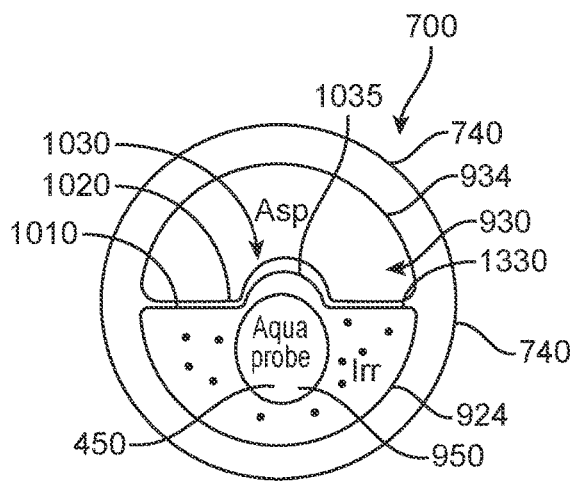
Figure 13C:
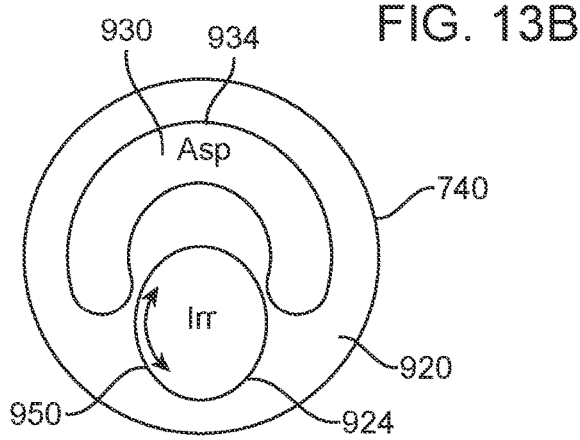

FIGS. 13A to 13C show cross-sectional views of probes comprising asymmetric internal structures to provide rotational stability.

FIG. 13A shows a probe 700 comprising a sheath 740, a fluid supply channel 920 and a fluid removal channel 930. The fluid supply channel 920 comprises a tube 924 and the fluid removal channel 930 comprises a tube 934, in which tube 924 and tube 934 are configured to engage each other. The tubes may comprise interlocking structures 1320 comprising a plurality of protrusions 1322 and a plurality of recesses 1324 to engage each other in an interlocking configuration. In some embodiments, a compressive element 1310, such as a spring is configured to urge the tubes and interlocking structures towards each other to add stability. The interlocking structures may extend along the probe to add rotational and translational stability.

FIG. 13B shows a probe 700 comprising a sheath 740, a fluid supply channel 920 and a fluid removal channel 930. The fluid supply channel 920 comprises a tube 924 and the fluid removal channel 930 comprises a tube 934, in which tube 924 and tube 934 are configured to engage each other. One or more of the tubes is configured to receive a treatment probe as described herein. The tube 924 comprises an engagement structure 1010 configured to engage a corresponding engagement structure 1020 on tube 934 to provide rotational stability. The tubes may comprise additional engagement structures such as a recess 1030 on tube 934 shaped to engage a protrusion 1035 on tube 924 to provide translational stability when the tubes engage each other. The engagement surfaces of the tubes may comprise additional structures such as surface roughening to provide friction between the probes.

FIG. 13C shows a probe 700 comprising a sheath 740, a fluid supply channel 920 and a fluid removal channel 930. The fluid supply channel 920 comprises a tube 924 and the fluid removal channel 930 comprises a tube 934, in which tube 924 and tube 934 are configured to engage each other. One or more of the tubes is configured to receive a treatment probe as described herein.

In some embodiments, one or more elements comprise a non-symmetric shape to enables elements of the assembly to contribute to the torque transmission capability. In some embodiments, the axially extending elements comprise engagement structures, such as interlocking structures. In some embodiments, the structures can be actuated via one or more of a screw function or pull/push function. In some embodiments, the probe elements are configured to interact at one or more of proximal locations, distal locations, or along the assembly, for example.

In some embodiments, the components comprise mating shape between pieces such as single or multiple mating bulges or ramps, and/or 3-D interlocking features preventing system expansion, in which movement between them causes locking.

In some embodiments, the working elements comprise sufficient rigidity to faithfully execute movement with decreased hysteresis.

In some embodiments, one or more components comprise a cylindrical geometry, e.g. an annular geometry, to engage a cylindrical wall of another component and utilize available wall thickness.

In some embodiments, the outer shaft of the surgical probe 700 provides rigidity from bending to assure accurate movement and positioning within the surgical space. The outer shaft can also protect the inner elements from bending while allowing them to perform their function of rotation, translation, e.g. pistoning, and actuation of offset.

In some embodiments, the components of the probe comprise a reversibly interlocking structure which causes the individual elements to bind with each other to create a round torque cylinder with inner elements bound together within a sheath. In some embodiments, the cross-sectional profile of the probe elements enhances torque transmission of the inner assembly due to their engagement with each other. They are examples of several of many different geometric interlocking configurations that may be used in accordance with the present disclosure.

Although 2-dimensional cross-sectional views are shown, in some embodiments the probe elements comprise a 3-dimensional geometric interlocking feature such that the relative axial movement of elements can be reduced.

Figure 14A:
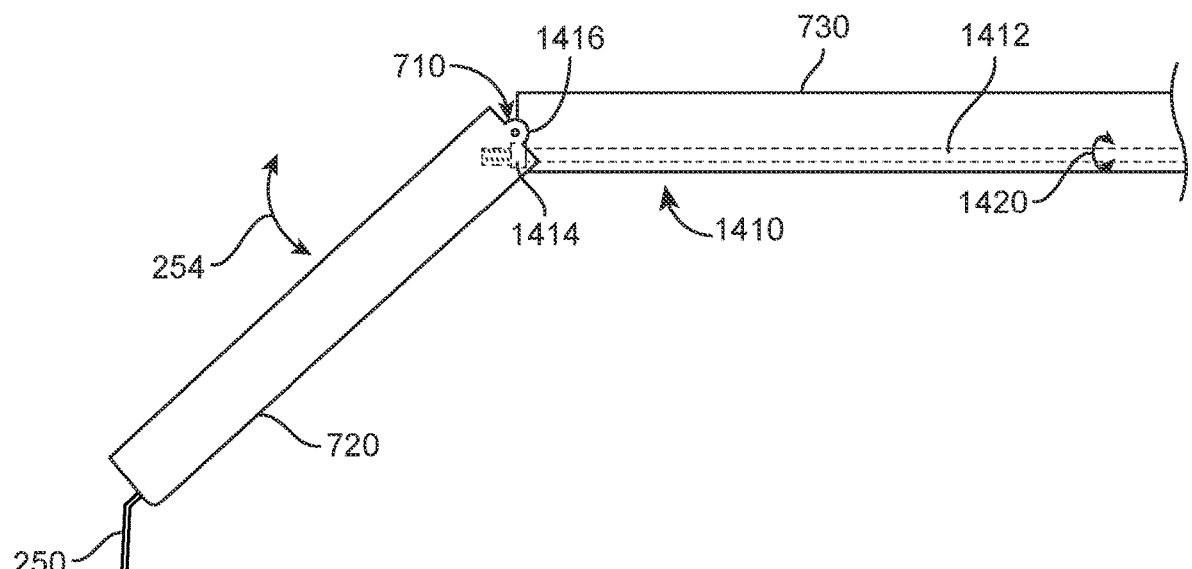
FIGS. 14A and 14B shows push pull structures to offset the energy source, in accordance with some embodiments.
Figure 14B:
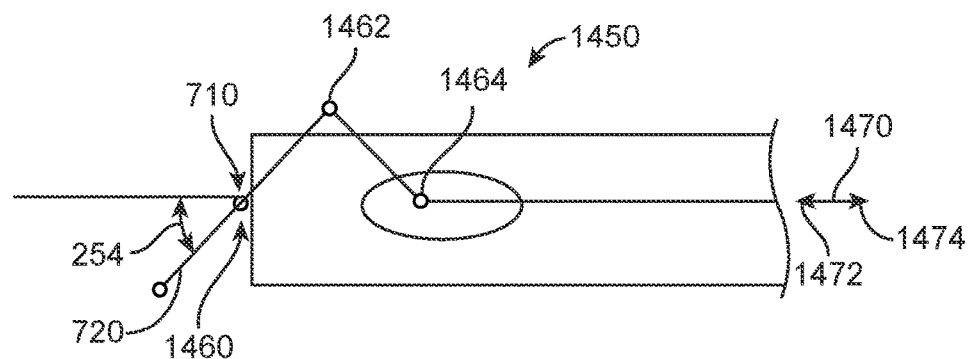

FIGS. 14A and 14B show push pull structures to offset the energy source.

In some embodiments, a tube within a tube configuration comprises a push/pull configuration causing angle bend or other action. The linkage can be configured in many ways and may comprise one or more of a pull wire or a nut drive, for example. In some embodiments, a push/pull wire assembly is configured to provide angular deflection. The linkage may comprise slots and pins as appropriate, for example.

In some embodiments, a push/pull coaxial tube drive shaft 1412 may be a threaded rod that is threadedly coupled to a proximal end of the extension 720, which rotates to deflect the extension 720 and displace the energy source 250. In some embodiments, the linkage comprises an anti-backlash feature, e.g. a spring-loaded nut with threads on both directions of actuation.

The linkage can extend proximally to couplings and controls as described herein.

FIG. 14A shows a probe comprising a rotational linkage 1410. The linkage 1410 may comprise a threaded female structure 1416, similar to a nut, and a threaded drive shaft 1412. The threaded female structure 1416 is shaped to receive a threaded rod 1412. Upon rotation 1420 of rod 1412, extension 720 is moved toward or away from the elongate axis, depending on the direction of rotation. The link 710 is coupled to the threaded structures to pivot extension 720 about link 710 and provide deflection 254.

FIG. 14B shows a probe comprising a push pull linkage 1450 to move the energy source with deflection 254 of the extension as described herein. The link 710 may comprise a pin 1460, for example. The linkage may comprise additional pins 1462, 1464, coupled to additional extensions that extend proximally from the extension 720. Translational movement 1470 moves the energy source toward and away from the elongate axis. In some embodiments, distal movement 1472 deflects extension 720 away from the elongate probe axis and proximal movement 1474 moves the extension 720 toward the elongate axis.

FIGS. 15A to 15D show surface followers to position the energy source in relation to a depth from a tissue surface profile.

Although these illustrations show an electrocautery wire as the energy source, any suitable energy source could be employed as described herein. In some embodiments, the surface follower is configured to slide along the surface of the tissue while the energy source extends into the tissue to one or more of a single set depth, or user adjustable depth to achieve a depth of treatment.

Figure 15A:
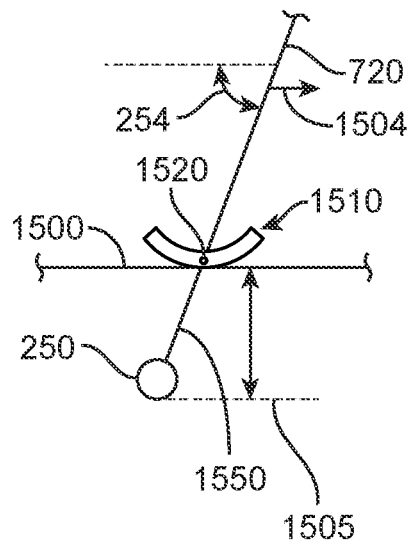
FIGS. 15A to 15D show surface followers to position the energy source in relation to a depth from a tissue surface profile, in accordance with some embodiments.
Figure 15B:
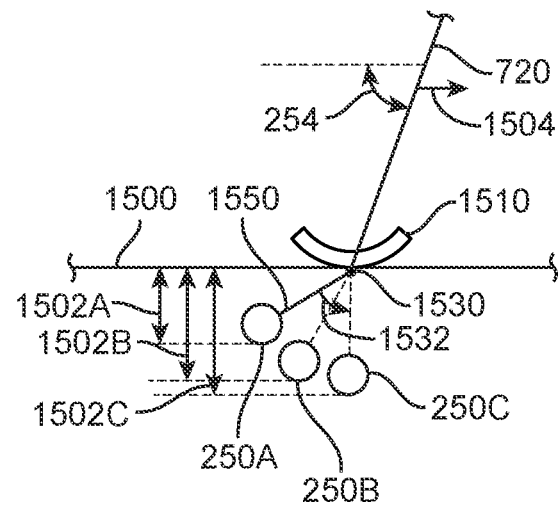

FIGS. 15A and 15B show an energy source coupling element pivoted about an axis where the angular displacement relative to the follower provides a greater resection depth.

FIG. 15A shows a follower 1510 coupled to the extension 720 and the energy source 250 to engage a tissue surface 1500 and follow the tissue surface. When the follower is moved in a direction 1504 by the extension 720 the follower allows the energy source to resect tissue at a depth from the tissue surface. An elongate member 1505 extends between the follower 1510 and the energy source to control the depth 1502 of tissue resection. The member 1505 may comprise a substantially fixed length between the follower 1510 and energy source 250. Alternatively, the member 1505 may comprise a variable length to vary the tissue resection depth from tissue surface 1500.

The follower 1510 can be configured in many ways and is typically wider than member 1505, such that the follower can slide along the tissue surface. In some embodiments, the follower 1510 comprises a support with a curved surface to slide along the tissue surface. The tissue surface may comprise any suitable surface such as an intact wall of tissue of a lumen, or a resected tissue surface where additional resection may be helpful. Work in relation to the present disclosure suggests that some types of tissue, such as water jet resected tissue, may comprise fibrous surfaces, and the follower can also be helpful in removing fibrils by smoothing the fibrils and cauterizing the fibrils beneath the follower 1510.

In some embodiments, the energy source 250 is coupled to the follower 1510 to vary one or more of a distance or an angle between the follower and the energy source to resect tissue to the depth 1502.

As shown in FIG. 15A, the follower 1510 is configured to with a pivot 1520. The angle between the follower and the elongate member 1505 corresponds to an amount of deflection of the extension from the elongate probe axis. Increasing the deflection of extension 720 increases the angle between the follower and the energy source and the corresponding resection depth from the tissue surface.

FIG. 15B shows a follower 1510 coupled to an energy source 250 with an elongate member configured to vary the depth of resection to a plurality of depths 1502A, 1502B, and 1502C. The tissue can be cut to the depths by varying one or more of the distance or the angle varies with respect to the elongate surface profile of follower 1510. The elongate surface profile of the follower is show engaging tissue 1500. The extension 720 may comprise one or more of a wire, a shaft, a lever, an extension, a rod, or a linkage extending along the extension to vary the one or more of the distance or the angle in order to vary the depth of resection from the tissue surface profile.

As shown in FIG. 15B, the follower 1510 is configured to pivot the member 1505 relative to the follower 1510 and the extension 720 to vary the distance to the plurality of distances 1502A, 1502B, 1502C.

The pivot 1530 can cause the angle 1532 of the member 1505 to vary with respect to follower 1510 and extension 720. In some embodiments, the angle between the elongate surface profile and the member 1505 increases to increase the depth to the depth 1502C and decreases to decrease the depth to the depth 1502A.

While the resection can be performed in many ways, in some embodiments the angle between the follower and the energy source is adjusted to vary the resection distance between the slider and the energy source while an amount of deflection of the extension remains substantially fixed.

Figure 15C:
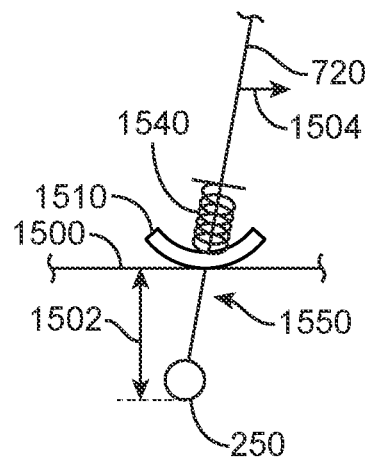

FIG. 15C shows the follower 1510 coupled to the extension 720 with a spring 1540. The follower is configured to slide along the extension 720. The spring 1540 allows the follower 1510 to provide a variable force to the tissue surface 1500. In some embodiments, the spring 1540 comprises a force limiting feature, enabling the treatment element to vary in depth based on the reaction force during execution.

Figure 15D:
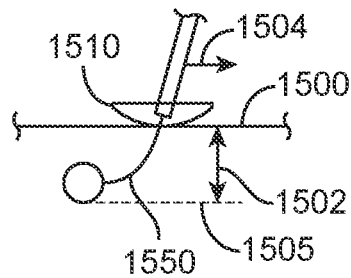

FIG. 15D shows the follower coupled to the energy source with a deflectable member 1550 such as a spring, e.g. a leaf spring. The member 1550 is configured to decrease the depth in response to tissue increased tissue resistance and to increase the depth in response to decreased tissue resistance. As shown in FIG. 15D, a preformed wire or spring element is configured to control the position of the treatment element in which the length of the spring element influences the resection depth from the follower 1510.

FIGS. 16A to 16C show an energy source 250 coupled to a surface follower 1510 with a pivot 1530 near a surface of the tissue follower. The extension 720 comprises one or more push pull extensions 1610 coupled to energy source 250. The one or more wires 1610 extend from extension 720 within one or more tubes 1630 to pivot the energy source 250 about a pivot axis 1531 along a path 1532 with respect to tissue follower 1510. Translational motion 1620 of wires 1610 within extension 720 can be used to adjust the pivot angle. The pivot angle can be adjusted to resect tissue to a first depth 1502A as shown in FIG. 16B or to a second depth 1502B as show in FIG. 16C.

FIGS. 17A to 17C show an energy source 250 coupled to a surface follower 1510 with a variable extension depth of the energy source 250 from the follower 1510 to the tissue. The variable extension depth can be controlled with one or more push pull extensions 1610, such as wires, tubes or shafts, which can be used to vary the depth. In some embodiments, retraction of the extensions 1610 between the follower and the energy source decrease the distance to first distance 1502A and advancement of the extensions 1610 increase the distance to second distance 1502B.

The link 710 can be configured in many ways to offset the energy 250 source from the elongate axis 451. In some embodiments, the link comprises one or more of a pivot, a hinge, a bendable link, a plurality of slits in a tube, or a plurality of non-planar slits in a tube, for example.

FIG. 18A shows deflection of link 710 comprising a bendable link to deflect the energy source with complimentary structures, e.g. interlocking structures, to provide rotational stability. FIG. 18B shows a cross-sectional view of the probe as in FIG. 18A. FIG. 18C shows a bottom view of the probe of FIGS. 18A to 18B. FIG. 18D shows deflection of the probe of FIGS. 18A to 18C with a deflection angle greater than 45 degrees from an elongate axis of the probe.

The bendable link can be configured in many ways and may have an internally actuated tension or distension feature to add rigidity to the distal end. In some embodiments, the slits interlocking elements which interlock in three dimensions, such as radially, and with wedge features, for example. In some embodiments, the slits are fabricated by laser cutting tubing with the laser angles to create a conical shape, in which the male cone fits into the female cone, for example. In some embodiments, the cut tubing comprises interlocking slits pieces enhance rotational stability.

In some embodiments, the angle of deflection 254 can be controlled by distance of link elements extended beyond a distal opening 1850 of sheath 740. The rotational and translation position of the link 710 can be controlled by shaft 730, for example. In some embodiments, the link 710 comprises a plurality of slits 1800 defining a plurality of gaps 1810. One or more of a plurality of distances across the plurality of gaps 1810 is configured to decrease to deflect the extension 720 and move the energy source 250 away from the elongate axis. The plurality of slits 1800 extends through a first side of the tube and only partially through a second side of the tube to allow the tube to bend along the second side with decreases of the plurality of distances along the first side. In some embodiments, the plurality of slits 1800 is configured to close at least partially along one or more of the plurality of slits to deflect the extension and move the energy source away from the axis. In some embodiments, the angle of deflection is related to the number of closed slits 1820.

The slits can be configured to provide improved stiffness and resistance to torsional deflection with appropriate structures. In some embodiments, the plurality of slits comprises non-planar slits 1860, e.g. V-shaped slits. The non-planar slits comprise corresponding opposing engagement structures to engage each other with at least partial closure of the plurality of slits.

In some embodiments, the sheath 740 comprises retention sheath over the plurality of slits to control the deflection angle of the extension by uncovering of one or more of the plurality of slits from the sheath. The angle of deflection 254 is related to a number of slits uncovered from the sheath and a distance by which one or more of the plurality of slits extends beyond a distal end 1850 of the sheath. As shown in FIGS. 18A to 18D, the angle of deflection 254 can be progressively increase with uncovering of the slits, as shown with deflections 254A, 254B and 254C, respectively.

In some embodiments, a linkage is coupled to one or more of the sheath or the plurality of slits to move one or more of the slits or the shaft and expose and cover the plurality of slits with the shaft to control the deflection angle. The linkage may comprise any suitable linkage as describe herein and may comprise one or more of a screw link, a preloaded spring, a pull wire, a gear, or a rod coupled to a proximal portion of the probe, for example.

The sheath can be configured in any suitable way to keep the gaps open when retained within sheath 740. In some embodiments, the sheath 740 comprises sufficient stiffness to move the extension and the energy source toward the elongate axis after the extension has been deflected away from the elongate axis. In some embodiments, the sheath comprises sufficient stiffness to open one or more of the plurality gaps after distances across the one or more of the plurality of gaps has decreased in order to move the energy source and the extension toward the elongate axis.

Figure 19A:
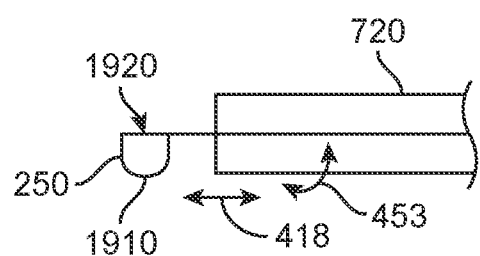
FIGS. 19A and 19B show side and top views, respectively, of a probe with an electrocautery wire a cutting surface extending at an oblique angle to a bending element, in accordance with some embodiments.
Figure 19B:
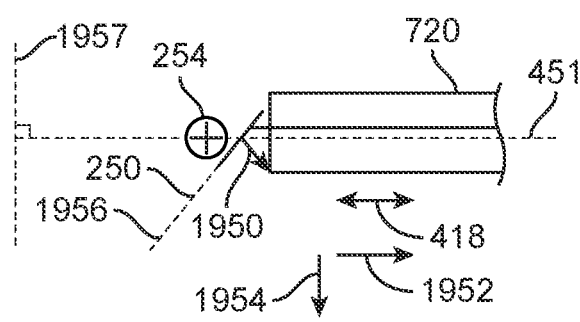

FIGS. 19A and 19B show side and top views, respectively, of a probe with an energy source such as an electrocautery wire cutting extending at an oblique angle to a bending element. In some embodiments, the cutting edge of the electrode is at an oblique angle to the shaft, e.g. 45° to allow the cutting action to occur in a direction 1950 with both a rotational movement 1954 and translational movement 1952, e.g. an axial movement. In some embodiments, this oblique angle increases a rate of tissue with axial and rotational movement, for example when a direction of movement of the electrode is substantially perpendicular to the tissue receiving region of the electrode.

As shown in FIG. 19B, the deflection 254 of the extension 720 and the electrode away from the shaft can be aligned with the elongate axis, such that the deflection 254 remains aligned with the elongate axis, which can improve rotational accuracy and decrease errors associated with eccentric movement of the energy source 250.

The energy source 250 may comprises an electrode shaped to define a region 1920 through which resected tissue can pass while the electrode resects tissue with movement of the electrode. In some embodiments, the region 1920 defined by the electrode extends in a direction 1956 oblique to the elongate axis 451 of the shaft and a plane perpendicular to the elongate axis of the shaft.

While the region 1920 can be configured in many ways, in some embodiments the region comprises an area defined by a non-linear shape of the cutting edge 1910 the electrode. The area defined by edge 1910 extends in the direction 1956 oblique to the elongate axis of the shaft and the plane 1957 perpendicular to the elongate axis 451. The non-linear shape may comprise a portion of a loop such that the portion of the loop defines the area of region 1920. In other words, the region is defined by a curved electrode and wherein the curved electrode extends in a direction oblique to the elongate axis of the shaft and the plane perpendicular to the elongate axis.

While the oblique angle can be configured in many ways, in some embodiments the direction 1956 extends at an angle to the elongate axis 451 and the plane 1957 with the angle within a range from about 15 degrees to about 75 degrees and further optionally within a range from about 30 degrees to about 60 degrees.

The oblique configuration of the electrode is well suited for processor-controlled tissue sculpting with rotational and translational movement as described herein. The processor is operatively coupled to the linkage comprising the shaft to rotate and translate the electrode with the extension deflected away from the elongate axis. The processor can be configured with instructions to offset the electrode from the elongate axis and rotate and translate the shaft to move the electrode with rotational movement 1954 and translational movement 1952 in order to pass tissue through the region 1920 defined by the non-linear shape of the cutting edge 1910 of the electrode. In some embodiments, the cutting edge 1910 of the electrode extends in the direction 1956 and the processor is configured with instructions to move the electrode transverse to the direction along which the cutting edge extends in order to promote movement of the resected tissue through the region 1920. In some embodiments, the processor is configured to decrease (e.g. limit) movement of the electrode in the direction 1956 along which the cutting edge extends.

While the probe can be configured to move the electrode in many ways, in some embodiments the direction of movement of the electrode corresponds to synchronous rotational movement 1954 and translational movement 1952 of the electrode.

Figure 20A:
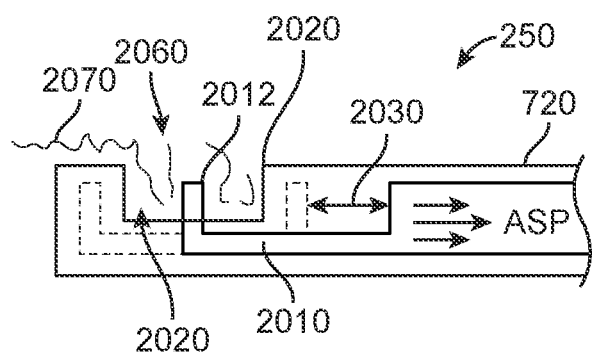
FIGS. 20A and 20B show an energy source comprising a mechanical cutting element, in accordance with some embodiments.
Figure 20B:
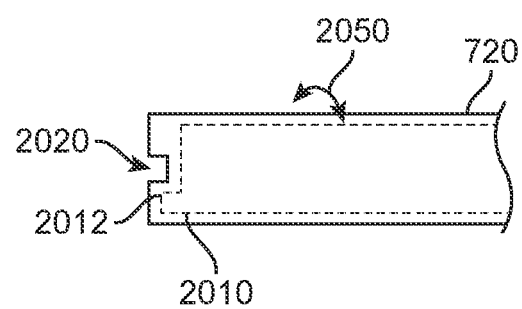

FIGS. 20A and 20B show an energy source 250 comprising a mechanical energy source such as a cutting element. In some embodiments, the energy source comprises a mechanical cutting shear to resect tissue. The cutting element comprises a moving cutting edge and a moving cutting edge 2030.

FIG. 20A shows a fixed outer tube with cutting edge 2020 on one or two surfaces (distal, proximal, or both) which interact with a reciprocating inner element 2010 comprising an edge 2012 to shear tissue. The inner element 2010 may comprise a tubular center region to remove sheared tissue. The inner element 2010 moves back and forth either in singular physician-controlled motion or by a motorized reciprocation, for example. In some embodiments, the center lumen of the assembly can be used under vacuum aspiration to remove the cut tissue, for example.

Although reference is made to movement of the inner element with a fixed outer element, the movement can be reversed.

FIG. 20B shows tissue shearing with rotational motion. An inner element 2010 comprises a cutting edge 2012. A stationary element comprises an edge 2020. The stationary element may comprise a castellated end of an outer tube. The inner element may comprise a close-fitting center tube which rotates or reciprocates 2050 to provide the tissue resection.

In some embodiments, an outer tube has a partially closed end that defines one or more openings to receive tissue, and an internal rotating cutting element shears tissue drawn into the one or more openings. An aspiration element such as a tube can be configured to draw tissue into the one or more openings to cut the tissue upon engagement with internal rotating element.

The stationary element may comprise a stabilizing structure to receive tissue and a cutting edge to engage the tissue against the stabilizing structure to resect the tissue with shearing upon engagement with the edge 2012 of the moving element. The cutting edge can be moved with one or more of translational or rotational motion to shear the tissue. The tissue stabilizing structure comprises a recess or aperture 2060 to receive tissue 2070.

In some embodiments, the mechanical energy source comprises one or more elements of a vitrector as will be known to one or ordinary skill in the art of eye surgery.

The mechanical source of energy 250 can be powered with one or more elongate structures that extend along the extension 720 to transmit energy to the energy source 250 with the extension deflected away from the axis as described herein.

FIGS. 21A to 21F show a variable offset energy source 250 comprising variable offset water jet coupled to a variable offset evacuation lumen. These embodiments show a jet lumen with the jet entering a receiving or evacuation lumen which together forms an eductor pump creating a localized vacuum able to draw loose tissue into the jet region allowing the jet power to act on the tissue cutting and ablating the tissue as it is driven down the evacuation lumen and out of the surgical space.

These configurations can provide tissue resection by drawing tissue into the water jet with entrainment. The tissue drawn in with entrainment may comprise any suitable tissue, such as naturally occurring tissue, or collagenous fibers subsequent to tissue resection with a water jet.

In some embodiments, one of the lumens comprises an electrically exposed surface to cauterize to tissue to promote hemostasis and tissue ablation.

Figure 21A:
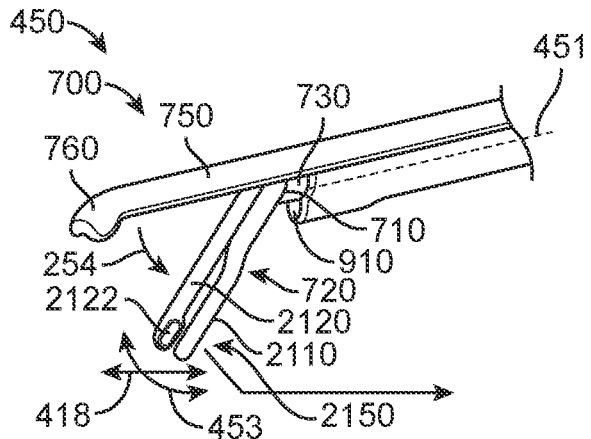
FIGS. 21A to 21F show a variable offset energy source comprising variable offset water jet and variable offset evacuation lumen, in accordance with some embodiments.
Figure 21B:
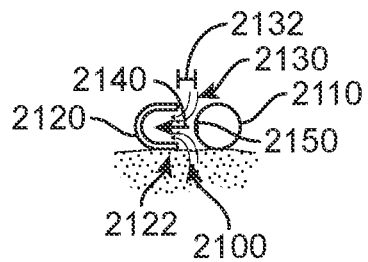

FIGS. 21A and 21B shows a probe 700 comprising a variable offset energy source 250. The probe 700 may comprise one or more components of probe 450 as described herein. The probe 700 may comprise components describe herein such as link 710, extension 720, shaft 730, spine 750 and tip 760. The link 710 can be configured to offset energy source 250 with deflection 254 of extension 720 as described herein. The extension 720 comprises a water jet supply tube 2110 coupled to a nozzle 2150 of a water jet, and a fluid removal channel 2120. The fluid removal channel 2120 extends to an opening 2122 to remove material generated with the energy source such as a water jet 2140. The water jet 2140 directed toward the opening 2122. The nozzle is coupled to jet supply tube 2110 to generate the water jet 2140. The nozzle 2150 of the water jet 2140 is oriented in a direction toward the opening 2122 to direct resected tissue toward the opening. In other words, the nozzle 2150 faces the opening 2122.

In some embodiments, the nozzle 2150 and the opening 2122 are separated by a gap 2130 defining a distance 2132 between the nozzle and the opening. The gap 2130 is sized to entrain tissue toward the water jet 2140 for resection. In some embodiments, the opening 2122, the nozzle 2150, and the gap 2130 are arranged in an eductor pump configuration to draw tissue into the gap. The distance may comprise any suitable distance and can be within a range from about 0.1 mm to about 5 mm and optionally within a range from about 0.25 mm to about 2.5 mm.

In some embodiments the extension 720 comprises the jet supply tube 2110 and the evacuation tube 2120. The evacuation tube 2120 comprising the fluid removal channel, and the jet supply tube and evacuation tube configured to move together to move the gap 2130 with deflection of the extension 703 as described herein.

In some embodiments, the jet supply tube 2110 and the evacuation tube 2120 are arranged in a side-by-side configuration. The jet supply tube and the evacuation tube can be arranged in an over under configuration, for example.

As shown in FIG. 21A, the nozzle is oriented toward the opening in a direction transverse to the elongate axis 451 and the opening 2122 is oriented in a direction transverse to the elongate axis. In some embodiments, the nozzle and the opening are oriented substantially perpendicular to the elongate axis. With these transverse configurations, the gap 2130 is placed in proximity to the tissue 2100 to facilitate removal of the tissue. Work in relation to the present configuration suggests that other configurations may be helpful, in accordance with the type of tissue removed.

In some embodiments, the water jet supply tube 2110 and the evacuation tube 2120 are arranged in a side-by-side configuration with respect to elongate axis 451, which can facilitate pivoting at link 710, for example.

Figure 21C:
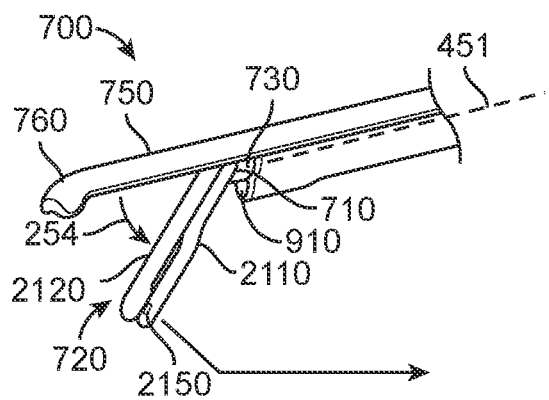
Figure 21D:
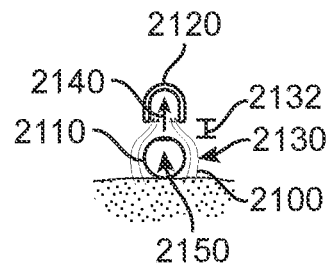

FIGS. 21C and 21D show the nozzle oriented toward the opening in a direction toward the elongate axis 451 near tip 760 of the probe 700, and the opening 2122 oriented away from the probe and the elongate axis. In some embodiments, the water jet supply tube 2110 and the evacuation tube 2120 are arranged in an over under configuration with respect to elongate axis 451, for example. The water jet supply tube 2110 can be located under evacuation tube 2120, for example.

Figure 21E:
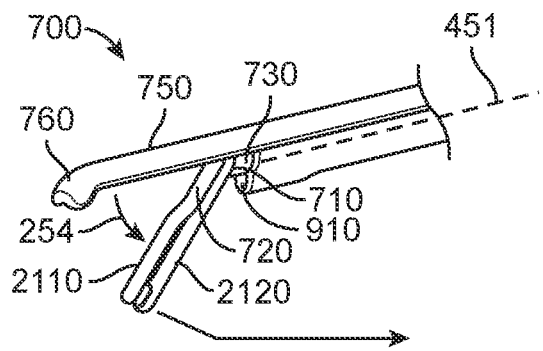
Figure 21F:
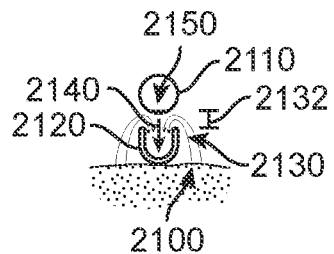

FIGS. 21E and 21F show the nozzle oriented in a direction away from the probe and elongate axis 451, and the opening 2122 oriented toward the elongate axis 451 near the tip 760. The water jet supply tube 2110 and the evacuation tube 2120 are arranged in an over under configuration with respect to elongate axis 451. The water jet supply tube 2110 is located above evacuation tube 2120.

Figures 22A, 22B:
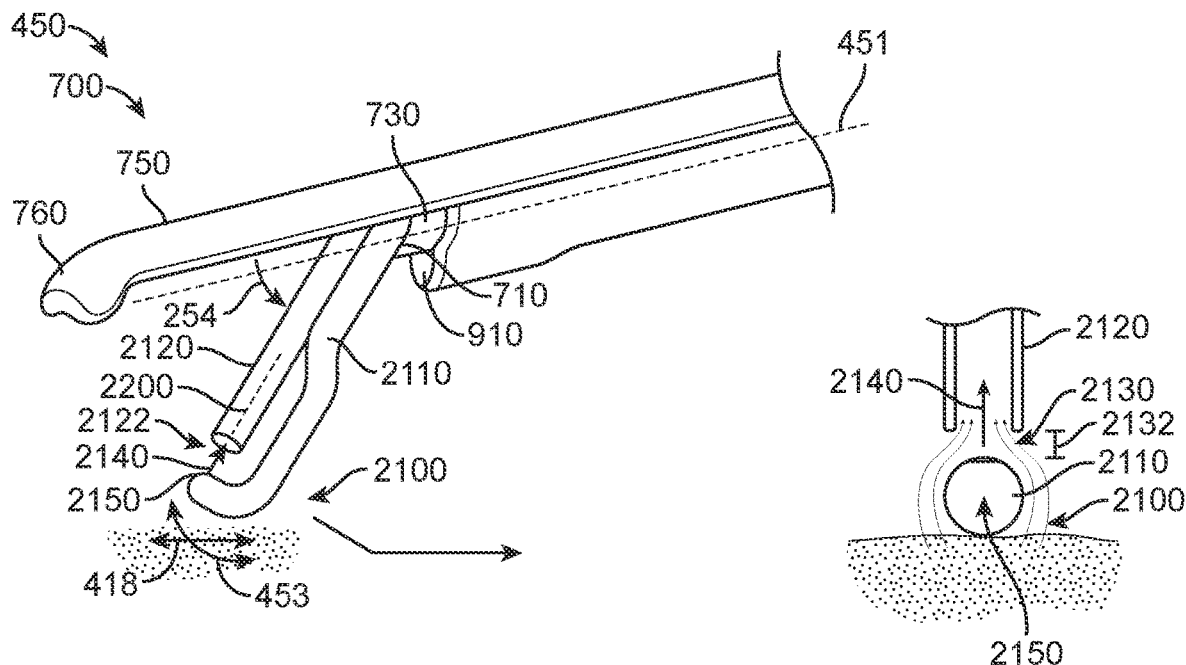
FIGS. 22A to 22C show a variable offset water jet and evacuation lumen in a retro-jet configuration, in accordance with some embodiments.
Figure 22C:
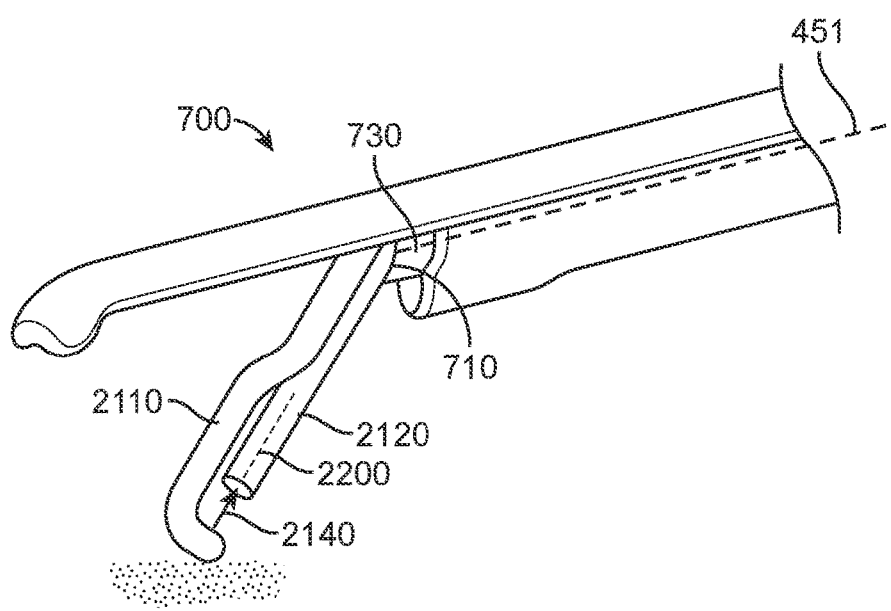

FIGS. 22A to 22C show probe 700 comprising a variable offset water jet and evacuation lumen in a retro water jet configuration. As illustrated, the probe 700 comprises components and movements similar to the probes shown in FIGS. 21E to 21F.

With these retro water jet configurations, the water jet is oriented toward link 710 and axis 451. As shown in FIG. 22A, the jet supply tube 2110 and the evacuation tube are arranged in a side-by-side configuration with respect to elongate axis 451. The water jet 2140 is oriented toward an elongate axis of elongate evacuation tube 2120, which can promote the drawing of tissue and fluid with entrainment.

FIG. 22C shows the jet supply tube 2110 and the evacuation tube arranged in an over under configuration with respect to elongate axis 451. The water jet supply tube 2110 is shown above evacuation tube 2120. The water jet 2140 is oriented toward an elongate axis of elongate evacuation tube 2120 to promote the drawing of tissue and fluid with entrainment.

Figure 23:
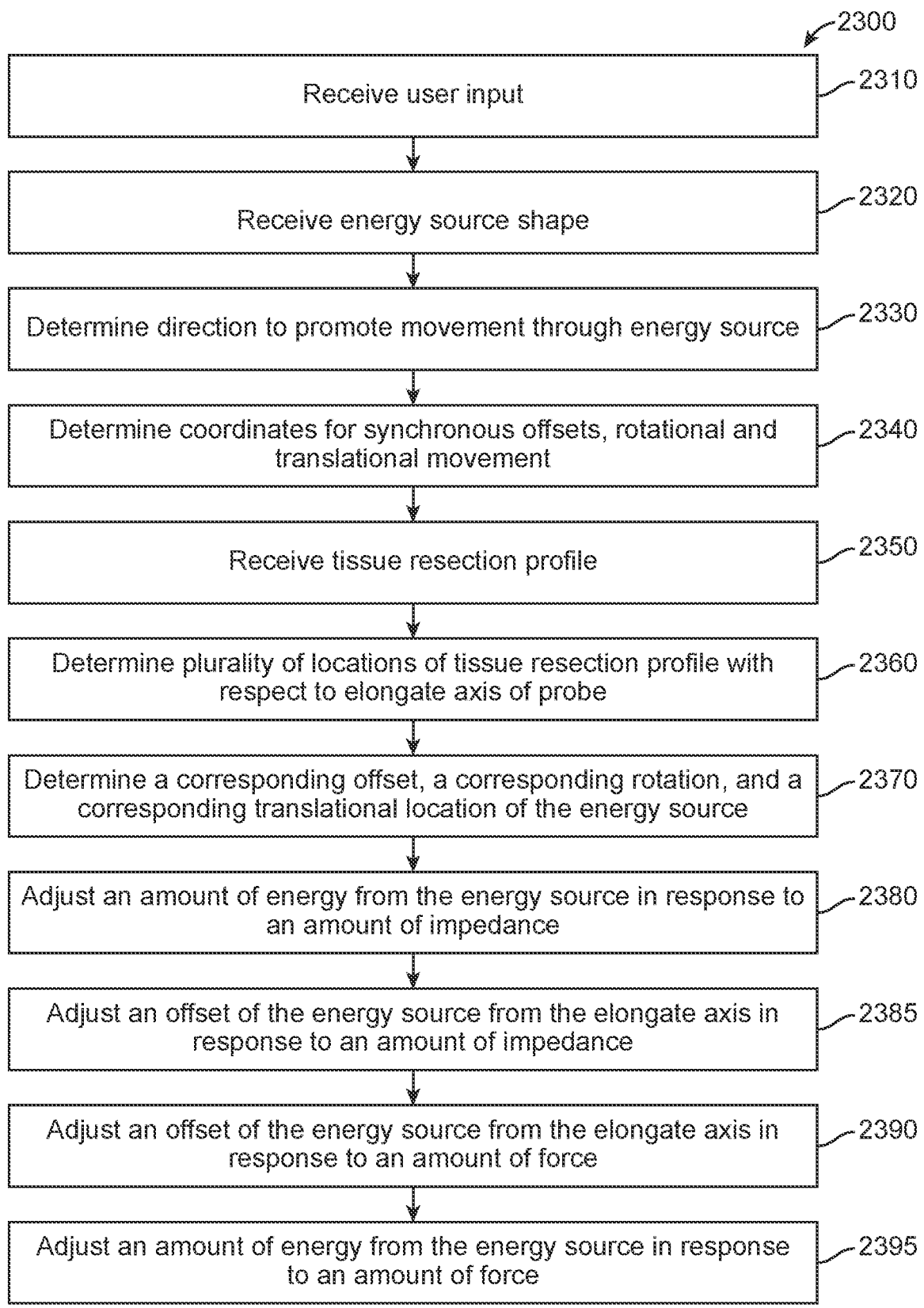
FIG. 23 shows a method of treating a patient, in accordance with some embodiments.

FIG. 23 shows a method 2300 of treating a patient.

At a step 2310, the processor receives a user input, such as a treatment profile or a movement command from a user control coupled to the linkage as described herein.

At a step 2320 the processor receives an input corresponding to shape of an energy source such as an electrode. The processor can be configured to rotate and translate the electrode with the extension deflected away from the elongate axis. In some embodiments, the processor configured with instructions to rotate and translate the elongate shaft to move the electrode and pass tissue through a region defined by the electrode.

At a step 2330, the processor determines a movement direction to promote tissue advancement through a region of the energy source such as an electrode. In some embodiments, a cutting edge of the electrode extends in a direction and the processor is configured with instructions to move the electrode transverse to the direction along which the cutting edge extends to promote movement of the resected tissue through the region. In some embodiments, the processor is configured with instructions to limit movement of the electrode in the direction along which the cutting edge extends.

At a step 2340, the processor determines a movement of the electrode corresponds to synchronous offsets, rotational and translational movement of the energy source such as an electrode. For example, the processor can be configured to simultaneously move the electrode with one or more of offset, rotation about the elongate axis, or translation along the elongate axis as described herein.

At a step 2350, the processor receives as input a tissue resection profile. In some embodiments, the processor is configured to determine a plurality of offsets of the energy source corresponding to the tissue resection profile.

The tissue resection profile may correspond to a three-dimensional tissue resection profile, and the processor configured with instructions to determine a plurality of offsets, translations and rotations of the energy source about the elongate axis to position the energy source at a plurality of locations corresponding to the three-dimensional tissue resection profile. Examples of suitable three-dimensional tissue resection profiles are described in PCT/US2014/054412, filed Sep. 5, 2014, entitled "AUTOMATED IMAGE-GUIDED TISSUE RESECTION AND TREATMENT", published as WO 2015/035249, the entire disclosure of which has been previously incorporated herein by reference.

At a step 2360, the processor determines a plurality of locations of the tissue resection profile with respect to the elongate axis of the probe.

At a step 2370, the processor determines a plurality of corresponding offsets, rotations and translations of the energy source with respect to the elongate axis. the processor determines a corresponding offset, a corresponding rotation, and a corresponding translational location of the energy source with respect to the elongate axis for each of the plurality of locations of the tissue resection profile. In some embodiments, the offset comprises a deflection of the energy source away from the elongate axis of the probe and wherein the processor is configured with instructions to determine a translation of a shaft coupled to the energy source in response to an angle of deflection of the energy source and a translational location of the three-dimensional profile with respect to the elongate axis.

At a step 2380, the processor adjusts an amount of energy from the energy source in response to an amount of impedance of the energy source.

At a step 2385, the processor adjusts an offset of the energy source from the elongate axis in response to an amount of impedance. In some embodiments, the processor is configured with instructions to adjust an amount of deflection of the extension and offset of the energy source from the elongate axis in response to an amount of impedance.

At a step 2390, the processor adjusts an offset of the energy source from the elongate axis in response to an amount of force measured with a force sensor.

At a step 2395, the processor adjusts an amount of energy from the energy source in response to an amount of force measured with a force sensor.

Although FIG. 23 shows a method of treating a patient in accordance with some embodiments, one of ordinary skill in the art will recognize many adaptations and variations. For example, the steps can be performed in any suitable order. Some of the steps can be omitted, and some of the steps can be repeated. Further, some of the steps may comprises sub-steps of other steps. Also, a computing devices such as a processor as described herein can be configured to perform one or more steps of method 2300.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A probe for treating a subject, comprising: an energy source; an elongate shaft comprising an elongate axis; an extension coupled to the elongate shaft with a link to move the energy source away from the elongate axis with movement of the extension away from the elongate axis to offset the energy source from the elongate axis.

Clause 2. The probe of clause 1, wherein the energy source comprises one or more of an electrode, a loop electrode, a monopolar electrode, a bipolar electrode, a radiofrequency source, a microwave source, a plasma source, a heat source, a laser source, a mechanical energy source, a mechanical sheer source, a vibrational energy source, an ultrasound energy source, cavitating ultrasound source, a water jet, a fixed pressure water jet, a variable pressure water jet, a water jet evacuation source, an eductor pump, a steam source, a morcellator, photo-ablation energy source, an ionizing radiation energy source, a radioisotope, an ionized plasma source, or a cryogenic energy source.

Clause 3. The probe of clause 1, further comprising a sheath, the elongate shaft located within the sheath to allow rotation and translation of the energy source relative to the sheath with the extension deflected away from the elongate axis.

Clause 4. The probe of clause 3, further comprising a fluid supply channel and a fluid removal channel within the sheath and optionally wherein the fluid supply channel comprises one or more of an insufflation channel or an irrigation channel and the fluid removal channel comprises one or more of a drainage channel or an aspiration channel.

Clause 5. The probe of clause 4, wherein the fluid supply channel and the fluid removal channel are sized and shaped to engage each other within the sheath with one or more of the fluid supply channel or the fluid removal channel sized and shaped to receive the elongate shaft coupled to the energy source to allow rotation and translation of the energy source with the energy source deflected away from the elongate axis.

Clause 6. The probe of clause 5, wherein the fluid supply channel is sized and shaped to receive the elongate shaft to provide fluid supply to a surgical site along the fluid supply channel with the elongate shaft placed within the fluid supply channel.

Clause 7. The probe of clause 5, wherein the fluid removal channel is sized and shaped to receive the elongate shaft to remove fluid from a surgical site along the fluid removal channel with the elongate shaft placed within the fluid removal channel.

Clause 8. The probe of clause 5, wherein the fluid supply channel comprises a first tube and the fluid removal channel comprises a second tube and the first tube and the second tube are sized and shaped to engage each other to provide rotational stability while the elongate shaft rotates and translates.

Clause 9. The probe of clause 8, further comprising a resilient structure coupled to the sheath, the first tube, and the second tube to urge the first tube and the second tube toward each other and provide rotational stability.

Clause 10. The probe of clause 8, wherein the first tube comprises a first portion and the second tube comprises a second portion sized and shaped to engage the first portion with a nested configuration.

Clause 11. The probe of clause 8, wherein the first tube comprises a first portion with a first surface profile and the second tube comprises a second portion with a second surface profile sized and shaped to engage the first surface profile.

Clause 12. The probe of clause 11, wherein the first surface profile and the second surface profile comprise a curved protrusion and a curved recess to engage each other along an axially extending length of the curved protrusion and the curved recess.

Clause 13. The probe of clause 11, wherein the first portion and the second portion comprise a plurality of engagement structures sized and shaped to engage each other.

Clause 14. The probe of clause 13, wherein the plurality of engagement structures comprises a plurality of protrusions and a plurality of recesses sized and shaped to fit together in an interlocking configuration.

Clause 15. The probe of clause 14, wherein the plurality of engagement structures extends axially along the first tube and the second tube to provide torsional stability to the elongate shaft.

Clause 16. The probe of clause 11, wherein the first tube comprises a third surface profile sized and shaped to engage an interior of the sheath and the second tube comprises a fourth surface profile sized and shaped to engage the interior of the sheath and optionally wherein the interior of the sheath comprises a circular profile and the third surface profile comprises a circular profile and the fourth surface profile comprises a circular profile.

Clause 17. The probe of clause 3, wherein the sheath comprises stiffness to add rigidity and stabilize the energy source with movement of the elongate shaft and movement of the energy source relative to the sheath.

Clause 18. The probe of clause 3 further comprising a spine coupled to the sheath to add stiffness to the probe.

Clause 19. The probe of clause 18, wherein the spine extends distally beyond the energy source.

Clause 20. The probe of clause 19, wherein the spine comprises a tube comprising one or more of a fluid fill channel or a fluid removal channel coupled to one or more openings distal to the energy source to provide a fluid or remove material generated by the energy source.

Clause 21. The probe of clause 20, wherein the spine comprises first side comprising a concave surface facing toward the energy source and spaced apart from the energy source and a second side comprising a convex surface facing away from the energy source to engage tissue.

Clause 22. The probe of clause 20, wherein the spine extends beyond a distal end of the sheath and the one or more openings are located distally beyond the distal end of the sheath.

Clause 23. The probe of clause 18, wherein the spine extends to a distal tip, the distal tip comprising a rounded end for insertion of the probe and a recess in the distal tip to allow fluid to pass around the distal tip when the distal tip engages a wall of a lumen.

Clause 24. The probe of clause 3, wherein the sheath comprises a flexible sheath.

Clause 25. The probe of clause 3, wherein the sheath comprises a cross-sectional diameter within a range from 3 mm to 12 mm and optionally within a range from 6 mm to 10 mm.

Clause 26. The probe of clause 3, wherein the link is configured to deflect the energy source from a first position near the elongate axis toward a second position away from the elongate axis, the first position, the second position and the link substantially defining a plane extending through the sheath.

Clause 27. The probe of clause 26, wherein the plane extends through a drive shaft coupled to the energy source to one or more of offset, rotate or translate the energy source relative to the shaft.

Clause 28. The probe of clause 27, wherein the elongate axis of the probe extends along the drive shaft to rotate the energy source about an axis of the drive shaft.

Clause 29. The probe of clause 28, wherein an axis of rotation of the energy source about the elongate axis of the probe is coaxial with an axis of rotation of the drive shaft.

Clause 30. The probe of clause 28, wherein the drive shaft comprises a tube and an axis of rotation of the energy source about the elongate axis of the probe extends along an interior of the tube.

Clause 31. The probe of clause 1 wherein the energy source is configured to advance and retract with translational movement over a distance within a range from about 0.5 cm to about 10 cm.

Clause 32. The probe of clause 1, wherein the extension is configured to deflect to move the energy source toward and away from the elongate axis with an offset distance from the elongate axis of no more than 5 cm.

Clause 33. The probe of clause 1, wherein the probe is configured to offset the energy source with an accuracy of tolerance of 1 mm or less with respect to a corresponding proximal movement of a linkage and optionally 0.25 mm or less.

Clause 34. The probe of clause 1, wherein the probe is configured to rotate the energy source with rotational accuracy tolerance of 1 degree or less with respect to a corresponding proximal movement of a linkage and optionally 0.5 degrees or less.

Clause 35. The probe of clause 1, wherein the probe is configured to translate the energy source with a translational accuracy tolerance of 1 mm or less with respect to a corresponding proximal movement of a linkage and optionally 0.25 mm or less.

Clause 36. The probe of clause 1, wherein the probe comprises a torsional stiffness within a range from about 10 Nm/radian to about 125 Nm/radian between the energy source and a proximal drive component coupled to a motor and optionally wherein the probe comprises a length within a range from 100 mm to about 400 mm.

Clause 37. The probe of clause 1, wherein one or more components of the probe comprises a torsional stiffness within a range from about 10 Nm/radian to about 125 Nm/radian and optionally wherein the one or more components comprises a length within a range from 100 mm to about 400 mm.

Clause 38. The probe of clause 1, wherein the probe comprises a bending stiffness within a range from about 200 N/m to about 2000 N/m between the energy source and a proximal drive component coupled to a motor and optionally wherein the probe comprises a length within a range from 100 mm to about 400 mm.

Clause 39. The probe of clause 1, wherein one or more components of the probe comprises a bending stiffness within a range from about 200 N/m to about 2000 N/m and optionally wherein the one or more components comprises a length within a range from 100 mm to about 400 mm.

Clause 40. The probe of clause 1, further comprising a digital endoscope comprising a lens and sensor array.

Clause 41. The probe of clause 40, wherein the digital endoscope is supported with the extension and the lens and the sensor array move away from the elongate axis with movement of the energy source away from the elongate axis.

Clause 42. The probe of clause 40, wherein a fluid supply channel or a fluid removal channel extends to one or more openings supported with the extension, the one or more openings configured to move with the energy source toward and away from the elongate axis with deflection and straightening of the link.

Clause 43. The probe of clause 1, wherein the elongate shaft comprises a first elongate drive tube to deflect the extension away from the elongate axis.

Clause 44. The probe of clause 43, wherein the elongate shaft comprises a second elongate drive tube to rotate and translate the energy source with the extension deflected from the elongate axis.

Clause 45. The probe of clause 44 wherein the first elongate drive tube and the second elongate drive tube are configured to rotate and translate together to move the energy source with rotation and translation with the extension deflected from the elongate axis.

Clause 46. The probe of clause 44, wherein the first elongate drive tube and the second elongate drive tube are configured to rotate and translate independently to move the energy source with rotation and translation.

Clause 47. The probe of clause 44, wherein the first elongate drive tube and the second elongate drive tube are arranged in a side-by-side configuration.

Clause 48. The probe of clause 44, wherein the first elongate drive tube and the second elongate drive tube are arranged with one drive tube over another.

Clause 49. The probe of clause 48, wherein the first elongate drive tube and the second elongate drive tube are arranged in a coaxial configuration.

Clause 50. The probe of clause 48, further comprising a sheath, the elongate shaft located within the sheath to allow rotation and translation of the energy source relative to the sheath with the extension deflected away from the elongate axis, wherein the first elongate drive tube and the second elongate drive tube are sized to receive a third drive tube coupled to a second energy source to rotate and translate the second energy source relative to the sheath.

Clause 51. The probe of clause 50, wherein the second energy source comprises one or more of an electrode, a loop electrode, a monopolar electrode, a bipolar electrode, a radiofrequency source, a microwave source, a plasma source, a heat source, a laser source, a mechanical energy source, a mechanical sheer source, a vibrational energy source, an ultrasound energy source, cavitating ultrasound source, a water jet, a fixed pressure water jet, a variable pressure water jet, a water jet evacuation source, an eductor pump, a steam source, a morcellator, photo-ablation energy source, an ionizing radiation energy source, a radioisotope, an ionized plasma source, or a cryogenic energy source.

Clause 52. The probe of clause 51, wherein the second energy source comprises the water jet.

Clause 53. The probe of clause 52, wherein a third elongate drive tube is coupled to a nozzle to generate the water jet.

Clause 54. The probe of clause 53, wherein the third elongate drive tube extends proximally from the nozzle within the first elongate drive tube and the second elongate drive tube to rotate and translate the water jet relative to the first elongate drive tube and the second elongate drive tube.

Clause 55. The probe of clause 1, wherein the energy source comprises an electrode, the electrode shaped to define a region through which resected tissue can pass while the electrode resects tissue with movement of the electrode.

Clause 56. The probe of clause 55, wherein the region defined by the electrode extends in a direction oblique to the elongate axis of the elongate shaft and a plane perpendicular to the elongate axis of the elongate shaft.

Clause 57. The probe of clause 55, wherein the region comprises an area defined by a non-linear shape of the electrode and wherein the area extends in a direction oblique to the elongate axis of the elongate shaft and the plane perpendicular to the elongate axis and optionally wherein the non-linear shape comprises a portion of a loop and the portion of the loop defines the area.

Clause 58. The probe of clause 55, wherein the region is defined by a curved electrode and wherein the curved electrode extends in a direction oblique to the elongate axis of the elongate shaft and the plane perpendicular to the elongate axis.

Clause 59. The probe of clause 58, wherein the direction extends at an angle to the elongate axis and the plane, and wherein the angle is within a range from about 15 degrees to about 75 degrees and further optionally within a range from about 30 degrees to about 60 degrees.

Clause 60. The probe of clause 1, further comprising an impedance sensor coupled to the energy source to measure impedance of tissue treated with energy from the energy source.

Clause 61. The probe of clause 60, wherein the energy source comprises an electrode and the electrode comprises an impedance sensor.

Clause 62. The probe of clause 1, further comprising a force sensor coupled to the extension to measure tissue resistance related to deflection of the extension.

Clause 63. The probe of clause 62, wherein the force sensor is coupled to the link to measure tissue resistance related to movement of the energy source away from the elongate axis.

Clause 64. The probe of clause 1, further comprising a force sensor coupled to the energy source to measure tissue resistance related to a positioning distance of the energy source from the elongate axis.

Clause 65. The probe of clause 64, wherein the force sensor is configured to measure tissue resistance related to an amount of energy delivery from the energy source.

Clause 66. The probe of clause 1, further comprising a linkage coupled to the link to control an amount of offset of the extension away from the elongate axis, the linkage comprising one or more of a screw link, a preloaded spring, a pull wire, a tube or a rod coupled to a proximal portion of the probe and optionally wherein the offset corresponds to an amount of deflection of the extension.

Clause 67. The probe of clause 1, wherein the link comprises one or more of a pivot, a hinge, a bendable link, a plurality of slits in a tube, or a plurality of non-planar slits in a tube.

Clause 68. The probe of clause 67, wherein the link comprises the plurality of slits defining a plurality of gaps and wherein one or more of a plurality of distances across the plurality of gaps is configured to decrease to deflect the extension and move the energy source away from the elongate axis.

Clause 69. The probe of clause 68, wherein the plurality of slits extends through a first side of the tube and only partially through a second side of the tube to allow the tube to bend along the second side with decreases of the plurality of distances along the first side.

Clause 70. The probe of clause 68, wherein the plurality of slits is configured to close at least partially along one or more of the plurality of slits to deflect the extension and move the energy source away from the elongate axis.

Clause 71. The probe of clause 68, wherein the plurality of slits comprises non-planar slits, the non-planar slits comprising corresponding opposing engagement structures to engage each other with at least partial closure of the plurality of slits.

Clause 72. The probe of clause 68, further comprising a retention sheath over the plurality of slits to control a deflection angle of the extension uncovering of one or more of the plurality of slits from the retention sheath.

Clause 73. The probe of clause 72, wherein the deflection angle is related to a number of slits uncovered from the retention sheath.

Clause 74. The probe of clause 72, wherein the deflection angle is related to a distance by which one or more of the plurality of slits extends beyond a distal end of the retention sheath.

Clause 75. The probe of clause 74, further comprising a linkage coupled to one or more of the retention sheath or the plurality of slits to move one or more of the slits or the elongate shaft and expose and cover the plurality of slits with the elongate shaft to control the deflection angle.

Clause 76. The probe of clause 75, wherein the linkage comprises one or more of a screw link, a preloaded spring, a pull wire, or a rod coupled to a proximal portion of the probe.

Clause 77. The probe of clause 72, wherein the retention sheath comprises sufficient stiffness to move the extension and the energy source toward the elongate axis after the extension has been deflected away from the elongate axis.

Clause 78. The probe of clause 77, wherein the retention sheath comprises sufficient stiffness to open one or more of the plurality of gaps after distances across the one or more of the plurality of gaps has decreased in order to move the energy source and the extension toward the elongate axis.

Clause 79. The probe of clause 1, wherein the elongate shaft extends proximally toward a handle to control a rotation angle of the energy source about the elongate axis.

Clause 80. The probe of clause 79, wherein the elongate shaft is coupled to the handle to rotate the energy source with rotation of the handle.

Clause 81. The probe of clause 79, further comprising a linkage extending proximally toward the handle to control an offset distance of the energy source from the elongate axis.

Clause 82. The probe of clause 81, wherein the linkage comprises a knob to control the offset distance with rotation of the knob.

Clause 83. The probe of clause 81, further comprising a slider to translate the energy source along the elongate axis.

Clause 84. The probe of clause 81, wherein the linkage comprises a slider to control the offset distance with proximal and distal movement of the slider.

Clause 85. The probe of clause 79 further comprising a stiff sheath extending from the handle to an opening proximal of the link to add rigidity, wherein the elongate shaft is configured to move within the stiff sheath to translate the energy source and wherein a linkage extends between the link and the handle to offset the energy source from the elongate axis with rotation of a knob and wherein the handle and the stiff sheath move together to rotate the energy source about the elongate axis with rotation of the elongate shaft and linkage.

Clause 86. The probe of clause 85, further comprising a finger engagement structure to engage a finger of a user and a thumb engagement structure to engage thumb of a user and wherein the thumb engagement structure is coupled to the elongate shaft to translate the energy source with translation of the thumb engagement structure relative to the elongate shaft.

Clause 87. The probe of clause 1, further comprising a follower coupled to the extension and the energy source to engage a tissue surface and follow the tissue surface when moved by the extension to resect tissue at a depth from the tissue surface.

Clause 88. The probe of clause 87, wherein the follower comprises a support with a curved surface to slide along the tissue surface.

Clause 89. The probe of clause 87, wherein the energy source is coupled to the follower to vary one or more of a distance or an angle between the follower and the energy source to resect tissue to the depth.

Clause 90. The probe of clause 89, wherein the follower comprises an elongate surface profile to engage and slide along the tissue surface and wherein the one or more of the distance or the angle varies with respect to the elongate surface profile to vary the depth.

Clause 91. The probe of clause 90, wherein the follower is configured to follow a tissue surface profile to resect tissue to the depth and optionally wherein the depth from the tissue surface profile remains substantially constant when a distance of the tissue surface profile to the elongate axis of the probe varies.

Clause 92. The probe of clause 90, further comprising one or more of a wire, a shaft, a lever, an extension, a rod, or a linkage extending along the extension to vary the one or more of the distance or the angle to vary the depth of resection from the tissue surface.

Clause 93. The probe of clause 90, wherein the follower is configured to pivot relative to the extension to vary the distance.

Clause 94. The probe of clause 93, wherein an angle between the elongate surface profile and the extension increases to increase the depth and decreases to decrease the depth.

Clause 95. The probe of clause 94, wherein the angle corresponds to an amount of deflection of the extension from the elongate axis and wherein increasing the deflection increases the angle between the follower and the energy source and the depth from the tissue surface.

Clause 96. The probe of clause 90, wherein an angle between the follower and the energy source is adjusted to vary a resection distance between the follower and the energy source while an amount of deflection of the extension remains substantially fixed.

Clause 97. The probe of clause 96, wherein advancement of an elongate structure between the follower and the energy source increases the distance and retraction of the elongate structure decreases the distance and, optionally, wherein the elongate structure comprises a wire.

Clause 98. The probe of clause 90, wherein the follower is coupled to the extension and the follower is coupled with a spring to provide a variable force to the tissue surface with the follower.

Clause 99. The probe of clause 90, wherein the follower is coupled to the energy source with a deflectable member to decrease the depth in response to tissue increased tissue resistance and to increase the depth in response to decreased tissue resistance.

Clause 100. The probe of clause 1, wherein the energy source comprises a mechanical energy source configured to resect tissue with shearing.

Clause 101. The probe of clause 100, wherein the mechanical energy source comprises a tissue stabilizing structure to receive tissue and a cutting edge to engage the tissue against the tissue stabilizing structure to resect the tissue with shearing.

Clause 102. The probe of clause 101, wherein the cutting edge is moved with one or more of translational or rotational motion to shear the tissue.

Clause 103. The probe of clause 101, wherein the tissue stabilizing structure comprises a recess to receive the tissue.

Clause 104. The probe of clause 100, wherein the mechanical energy source comprises a vitrector.

Clause 105. The probe of clause 100, wherein one or more elongate structures extend along the extension to transmit energy to the energy source with the extension deflected away from the elongate axis.

Clause 106. The probe of clause 1, further comprising a fluid removal channel coupled to the extension to move with the extension, the fluid removal channel extending to an opening to remove material generated with the energy source.

Clause 107. The probe of clause 106, wherein the energy source is directed toward the opening.

Clause 108. The probe of clause 107, wherein the energy source comprises a nozzle coupled to a jet supply tube to generate a water jet, the nozzle of the water jet oriented in a direction toward the opening to direct resected tissue toward the opening and optionally wherein the nozzle faces the opening.

Clause 109. The probe of clause 108, wherein the nozzle and the opening are separated by a gap defining a distance between the nozzle and the opening.

Clause 110. The probe of clause 109, wherein the gap is sized to entrain tissue toward the water jet for resection.

Clause 111. The probe of clause 109, wherein the opening, the nozzle, and the gap are arranged in an eductor pump configuration to draw tissue into the gap.

Clause 112. The probe of clause 109, wherein the distance is within a range from about 0.1 mm to about 5 mm and optionally within a range from about 0.25 mm to about 2.5 mm.

Clause 113. The probe of clause 109, wherein the extension comprises the jet supply tube and an evacuation tube, the evacuation tube comprising the fluid removal channel, wherein the jet supply tube and evacuation tube configured to move together to move the gap with deflection of the extension.

Clause 114. The probe of clause 113, wherein the jet supply tube and the evacuation tube are arranged in a side-by-side configuration.

Clause 115. The probe of clause 113, wherein the jet supply tube and the evacuation tube are arranged in an over-under configuration.

Clause 116. The probe of clause 108, wherein the nozzle is oriented toward the opening in a direction transverse to the elongate axis and the opening is oriented in a direction transverse to the elongate axis and optionally wherein the nozzle and the opening are oriented substantially perpendicular to the elongate axis.

Clause 117. The probe of clause 108, wherein the nozzle is oriented toward the opening in a direction toward the elongate axis and the opening is oriented away from the elongate axis.

Clause 118. The probe of clause 108, wherein the nozzle is oriented in a direction away from the elongate axis and the opening is oriented toward the elongate axis.

Clause 119. The probe of clause 1, further comprising a lumen to deliver one or more of a treatment compound, a photochemical treatment agent, a chemotherapeutic agent, or a hemostatic agent.

Clause 120. The probe of clause 1, further comprising a plurality of drive linkages to offset the energy source, translate the energy source, and rotate the energy source.

Clause 121. The probe of clause 120, wherein the plurality of drive linkages comprises drive linkages to rotate a second energy source and translate the second energy source.

Clause 122. The probe of clause 120, wherein the plurality of drive linkages comprises five or more drive linkages to offset the energy source, translate the energy source, rotate the energy source, rotate a second energy source and translate the second energy source.

Clause 123. The probe of clause 120, further comprising a first plurality of movable engagement structures coupled to the plurality of drive linkages configured to engage a second plurality of engagement structures on a robotic arm to drive the plurality of drive linkages and optionally wherein the first plurality of movable engagement structures and the second plurality of engagement structures comprise rotatable engagement structures.

Clause 124. The probe of clause 123, wherein the first plurality of movable engagement structures comprises five or more engagement structures configured to drive five or more linkages to offset the energy source, translate the energy source, rotate the energy source, rotate a second energy source and translate the second energy source.

Clause 125. A system, comprising: a processor operatively coupled to the probe of any one of the preceding clauses to move the energy source.

Clause 126. The system of clause 125, wherein the processor is coupled to the elongate shaft to rotate and translate the electrode with the extension deflected away from the elongate axis, the processor configured with instructions to rotate and translate the elongate shaft to move the electrode and pass tissue through a region defined by the electrode.

Clause 127. The system of clause 126, wherein a cutting edge of the electrode extends in a direction and the processor is configured with instructions to move the electrode transverse to the direction along which the cutting edge extends to promote movement of the resected tissue through the region and optionally to limit movement of the electrode in the direction along which the cutting edge extends.

Clause 128. The system of clause 126, wherein the movement of the electrode corresponds to synchronous rotational and translational movement of the electrode.

Clause 129. The system of clause 125, wherein the processor is configured to receive as input a tissue resection profile, and wherein the processor is configured to determine a plurality of offsets of the energy source corresponding to the tissue resection profile.

Clause 130. The system of clause 129, wherein the tissue resection profile corresponds to a three-dimensional tissue resection profile and wherein the processor is configured with instructions to determine a plurality of offsets, translations and rotations of the energy source about the elongate axis to position the energy source at a plurality of locations corresponding to the three-dimensional tissue resection profile.

Clause 131. The system of clause 129, wherein the processor is configured to determine a plurality of locations of the tissue resection profile with respect to the elongate axis of the probe and wherein the processor is configured to determine a plurality of corresponding offsets, rotations and translations of the energy source with respect to the elongate axis.

Clause 132. The system of clause 131, wherein the processor is configured with instructions to determine a corresponding offset, a corresponding rotation, and a corresponding location of the energy source with respect to the elongate axis for each of the plurality of locations of the tissue resection profile.

Clause 133. The system of clause 129, wherein the offset comprises a deflection of the energy source away from the elongate axis of the probe and wherein the processor is configured with instructions to determine a translation of a shaft coupled to the energy source in response to an angle of deflection of the energy source and a translational location of the three dimensional profile with respect to the elongate axis.

Clause 134. The system of clause 125, wherein the processor is configured with instructions to adjust an amount of energy from the energy source in response to an amount of impedance of the energy source.

Clause 135. The system of clause 125, wherein the processor is configured with instructions to adjust an offset of the energy source from the elongate axis in response to an amount of impedance.

Clause 136. The system of clause 125, wherein the processor is configured with instructions to adjust and amount of deflection of the extension and offset of the energy source from the elongate axis in response to an amount of impedance.

Clause 137. The system of clause 125, wherein the processor is configured with instructions to adjust an offset of the energy source from the elongate axis in response to an amount of force measured with a force sensor.

Clause 138. The system of clause 125, wherein the processor is configured with instructions to adjust an amount of energy from the energy source in response to an amount of force measured with a force sensor.

Clause 139. A method of treating tissue, the method comprising: inserting a probe into a patient; offsetting an energy source away from an elongate axis of the probe; and rotating and translating the energy source about the elongate axis of the probe with the energy source offset from the elongate axis.

Clause 140. The method of clause 139, wherein the probe comprises the probe of any one of the preceding clauses.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A probe for treating a subject, comprising:
   an energy source;
   a sheath
   an elongate shaft comprising an elongate axis, the elongate shaft configured to move the energy source with translation of the elongate shaft along the elongate axis relative to the sheath, the elongate shaft located within the sheath to allow rotation and translation of the energy source relative to the sheath with an extension deflected away from the elongate axis,
   wherein the extension is coupled to the elongate shaft with a link to rotate the extension about the link to move the energy source away from the elongate axis with movement of the extension away from the elongate axis to offset the energy source from the elongate axis; and
   a fluid supply channel and a fluid removal channel within the sheath, wherein the fluid supply channel comprises an irrigation channel and the fluid removal channel comprises an aspiration channel, wherein the fluid supply channel and the fluid removal channel are sized and shaped to engage each other within the sheath with one or more of the fluid supply channel or the fluid removal channel sized and shaped to receive the elongate shaft coupled to the energy source to allow rotation and translation of the energy source with the energy source deflected away from the elongate axis.

2. The probe of claim 1, wherein the energy source comprises a water jet evacuation source.

3. The probe of claim 1, wherein the fluid supply channel is sized and shaped to receive the elongate shaft to provide fluid supply to a surgical site along the fluid supply channel with the elongate shaft placed within the fluid supply channel.

4. The probe of claim 1, wherein the fluid removal channel is sized and shaped to receive the elongate shaft to remove fluid from a surgical site along the fluid removal channel with the elongate shaft placed within the fluid removal channel.

5. The probe of claim 1, wherein the fluid supply channel comprises a first tube and the fluid removal channel comprises a second tube and the first tube and the second tube are sized and shaped to engage each other to provide rotational stability while the elongate shaft rotates and translates.

6. The probe of claim 5, further comprising a resilient structure coupled to the sheath, the first tube, and the second tube to urge the first tube and the second tube toward each other and provide rotational stability.

7. The probe of claim 5, wherein the first tube comprises a first portion and the second tube comprises a second portion sized and shaped to engage the first portion with a nested configuration.

8. The probe of claim 5, wherein the first tube comprises a first portion with a first surface profile and the second tube comprises a second portion with a second surface profile sized and shaped to engage the first surface profile.

9. The probe of claim 8, wherein the first surface profile and the second surface profile comprise a curved protrusion and a curved recess to engage each other along an axially extending length of the curved protrusion and the curved recess.

10. The probe of claim 8, wherein the first portion and the second portion comprise a plurality of engagement structures sized and shaped to engage each other.

11. The probe of claim 10, wherein the plurality of engagement structures comprises a plurality of protrusions and a plurality of recesses sized and shaped to fit together in an interlocking configuration.

12. The probe of claim 11, wherein the plurality of engagement structures extends axially along the first tube and the second tube to provide torsional stability to the elongate shaft.

13. The probe of claim 8, wherein the first tube comprises a third surface profile sized and shaped to engage an interior of the sheath and the second tube comprises a fourth surface profile sized and shaped to engage the interior of the sheath.

14. The probe of claim 1, wherein the sheath comprises stiffness to add rigidity and stabilize the energy source with movement of the elongate shaft and movement of the energy source relative to the sheath.

15. The probe of claim 1 further comprising a spine coupled to the sheath to add stiffness to the probe.

16. The probe of claim 15, wherein the spine extends distally beyond the energy source.

17. The probe of claim 16, wherein the spine comprises a tube comprising one or more of the fluid supply channel or the fluid removal channel coupled to one or more openings distal to the energy source to provide a fluid or remove material generated by the energy source.

18. The probe of claim 1, wherein the energy source comprises one or more of an electrode, a loop electrode, a monopolar electrode, a bipolar electrode, a radiofrequency source, a microwave source, a plasma source, a heat source, a laser source, a mechanical energy source, a mechanical sheer source, a vibrational energy source, an ultrasound energy source, cavitating ultrasound source, a water jet, a fixed pressure water jet, a variable pressure water jet, a water jet evacuation source, an eductor pump, a steam source, a morcellator, photo-ablation energy source, an ionizing radiation energy source, a radioisotope, an ionized plasma source, or a cryogenic energy source.

* * * * *